US011976817B2

(12) United States Patent
Qiao et al.

(10) Patent No.: US 11,976,817 B2
(45) Date of Patent: May 7, 2024

(54) METHOD FOR DETECTING A DIOXIN EMISSION CONCENTRATION OF A MUNICIPAL SOLID WASTE INCINERATION PROCESS BASED ON MULTI-LEVEL FEATURE SELECTION

(71) Applicant: Beijing University of Technology, Beijing (CN)

(72) Inventors: Junfei Qiao, Beijing (CN); Zihao Guo, Beijing (CN); Jian Tang, Beijing (CN)

(73) Assignee: Beijing University of Technology, Beijing (CN)

( * ) Notice: Subject to any disclaimer, the term of this patent is extended or adjusted under 35 U.S.C. 154(b) by 821 days.

(21) Appl. No.: 17/038,723

(22) Filed: Oct. 26, 2020

(65) Prior Publication Data
US 2021/0033282 A1 Feb. 4, 2021

Related U.S. Application Data

(63) Continuation of application No. PCT/CN2019/107216, filed on Sep. 23, 2019.

(30) Foreign Application Priority Data

May 14, 2019 (CN) .......................... 201910397710.5

(51) Int. Cl.
*F23G 5/00* (2006.01)
*F23G 5/50* (2006.01)
*G01N 33/00* (2006.01)

(52) U.S. Cl.
CPC ........... *F23G 5/50* (2013.01); *G01N 33/0036* (2013.01); *F23G 2207/10* (2013.01); *F23G 2208/00* (2013.01)

(58) Field of Classification Search
CPC .... F23G 5/50; F23G 2207/10; F23G 2208/00; G01N 33/0036
See application file for complete search history.

(56) References Cited

U.S. PATENT DOCUMENTS 9,875,440 B1 1/2018 Commons
2015/0278703 A1 10/2015 Liu

FOREIGN PATENT DOCUMENTS

CN 103366100 A 10/2013
CN 107944173 A 4/2018
(Continued)

OTHER PUBLICATIONS

Hui Cao, Xingyu Yan, Yaojiang Li, Yanxia Wang, Yan Zho, Sanchun Yang, "A Component Prediction Method for Flue Gas of Natural Gas Combustion Based on Nonlinear Partial Least Squares Method," Mar. 19, 2014, Hindawi Publishing Corporation, The Scientific World Journal, vol. 2014, pp. 1-5. (Year: 2014).*

(Continued)

*Primary Examiner* — Mohamed Charioui
*Assistant Examiner* — Christine Y Liao

(57) ABSTRACT

A method for detecting a dioxin emission concentration of a municipal solid waste incineration process based on multi-level feature selection. A grate furnace-based MSWI process is divided into a plurality of sub-processes. A correlation coefficient value, a mutual information value and a comprehensive evaluation value between each of original input features of the sub-processes and the DXN emission concentration are obtained, thereby obtaining first-level features. The first-level features are selected and statistically processed by adopting a GAPLS-based feature selection algorithm and according to redundancy between different features, thereby obtaining second-level features. Third-level features are obtained according to the first-level features and statistical results of the second-level features. A (Continued)

PLS algorithm-based DXN detection model is established based on model prediction performance and the third-level features. The obtained PLS algorithm-based DXN detection model is applied to detect the DXN emission concentration of the MSWI process.

16 Claims, 15 Drawing Sheets

(56) References Cited

FOREIGN PATENT DOCUMENTS

| | | | |
|---|---|---|---|
| CN | 108062566 | A | 5/2018 |
| CN | 108090317 | A | 5/2018 |
| CN | 108549792 | A | 9/2018 |
| CN | 109190660 | A | 1/2019 |
| CN | 109492319 | A | 3/2019 |
| IN | 109583115 | A | 4/2019 |
| WO | 2005008572 | A1 | 1/2005 |

OTHER PUBLICATIONS

Zhenhao Tang, Haiyang Zhang "Modeling NOx emission of coal-fired boiler with differential evolution optimized least square support vector machine," 2018, Chinese Control And Decision Conference, pp. 3364-3367. (Year: 2018).*

Tang Jian et al. Soft Sensor method of Mill Load for Grinding Process based on GA-PLS from Spectral Data using Feature Selection, Jul. 2010.

Yujing Sun et al. Correlation Feature Selection and Mutual Information Theory Based Quantitative Research on Meteorological Impact Factors of Module Temperature for Solar Photovoltaic Systems, Dec. 2016, No. 1, vol. 10.

Hassan A. Arafat et al. Environmental performance and energy recovery potential of five processes for municipal solid waste treatment.

Hui Zhou et al. A review of dioxin-related substances during municipal solid waste incineration.

A. Mukherjee et al. A Review on Technologies of Removal of Dioxins and Furans from Incinerator Flue Gas.

Yuanan Hu et al. The growing importance of waste-to-energy (WTE) incineration in China's anthropogenic mercury emissions: Emission inventories and reduction strategies, 2018.

Tao Huang et al. Ultrasound-enhanced electrokinetic remediation for removal of Zn, Pb, Cu and Cd in municipal solid waste incineration fly ashes, 2018.

P. H.-Jonas et al. The Global Exposure of Man to Dioxins: A Perspective on Industrial Waste Incineration, 1993,No. 8, vol. 26.

Jing Bai et al. Mechanism and kinetics study on the ozonolysis reaction of 2,3,7,8-TCDD in the atmosphere, 2014.

Yu Mingfeng et al. The research of PCDD/Fs emission characteristics in flue gas from municipal solid waste incinerations, May 2018, No. 5, vol. 38.

T. Gouin et al. Variability of concentrations of polybrominated diphenyl ethers and polychlorinated biphenyls in air: implications for monitoring, modeling and control, 2005.

Hai-Jun Zhang et al. Influence of variation in the operating conditions on PCDD/F distribution in a full-scale MSW incinerator, 2008.

Qiao Junfei et al. Dioxin Emission Concentration Measurement Approaches for Municipal Solid Wastes Incineration Process:A Survey, Jun. 2020, No. 6, vol. 46.

Tang J, Qiao J F, Guo Z H. Soft Sensing of Dioxin Emission Concentration Based on Potential Characteristic Selective Integrated Modeling[J]. Acta Automatica Sinica, in trial.

Ni-Bin Chang et al. Statistical Modelling for the Prediction and Control of PCDDs and PCDFs Emissions From Municipal Solid Waste Incinerators, 1995.

Ni-Bin Chang et al.Prediction of PCDDs/PCDFs emissions from municipal incinerators by genetic programming and neural network modeling, 2000.

Tang Jian, Dioxin emission concentration soft measuring approach of municipal solid waste incineration based on selective ensemble kernel learning algorithm, 2019, No. 2, vol. 70.

Sond Bunsan et al. Modeling the dioxin emission of a municipal solid waste incinerator using neural networks, 2013.

Xiao Xiaodong et al. Prediction of dioxin emissions in flue gas from waste incineration based on support vector regression, Aug. 2017, No. 8, vol. 35.

Tang Jian et al. Dioxin emission concentration soft measurement based on multi-source latent feature selective ensemble modeling for municipal solid waste incineration process,Month, 201X, No. X, vol. X.

Abul Hasnat et al.Feature Selection in Cancer Microarray Data using Multi-Objective Genetic Algorithm combined with Correlation Coefficient, 2016.

Frederico Coelho et al.Multi-Objective Semi-Supervised Feature Selection and Model Selection Based on Pearson's Correlation Coefficient.

Roberto Battiti,Using Mutual Information for Selecting Features in Supervised Neural Net Learning, Jul. 1994, No. 4, vol. 5.

Jorge R. Vergara • Pablo A. Estevez, A review of feature selection methods based on mutual information,2014.

Anil K. Jain et al. Statistical Pattern Recognition: A Review, Jan. 2000, No. 1, vol. 22.

Francois Fleuret, Fast Binary Feature Selection with Conditional Mutual Information, 2004.

Pablo A. Estévez, Normalized Mutual Information Feature Selection,Feb. 2009, No. 2, vol. 20.

Fatemeh Amiri et al. Mutual information-based feature selection for intrusion detection systems, 2011.

Sara Mohammadi et al. Multivariate correlation coefficient and mutual information-based feature selection in intrusion detection,2017, No. 5, vol. 26.

Hanchuan Peng et al.Feature Selection Based on Mutual Information:Criteria of Max-Dependency, Max-Relevance, and Min-Redundancy, Aug. 2005, No. 8, vol. 27, p. 5 and 59.

Tihonov A N. О решении некорректно поставленных задач и методе регуляризации (Solution of incorrectly formulated problems and the regularization method), 1963.

S. Wold et al. The Collinearity Problem in Linear Regression. The Partial Least Squares (PLS) Approach to Generalized Inverses,Sep. 1984, No. 3, vol. 5.

R. Leardi et al. Genetic Algorithms as a Strategy for Feature Selection,1992, vol. 6.

Tang Jian et al. Soft sensing mill load in grinding process by time/frequency information fusion, May 2012, No. 5, vol. 29.

* cited by examiner

Table 1 Statistics of correlation measurement results of process variables of different sub-processes

| Serial number | Sub-processes | Correlation coefficient value | | | Mutual information value | | | Comprehensive evaluation value | | |
|---|---|---|---|---|---|---|---|---|---|---|
| | | Minimum values | Average values | Maximum values | Minimum values | Average values | Maximum values | Minimum values | Average values | Maximum values |
| 1 | Boiler operation | 0.06305 | 0.1743 | 0.3358 | 0.2596 | 0.5861 | 0.8025 | 0.09123 | 0.1250 | 0.1568 |
| 2 | Incineration treatment | 0.006888 | 0.2098 | 0.6760 | 0.4680 | 0.7254 | 0.8665 | 0.01771 | 0.02380 | 0.03661 |
| 3 | Stack emission | 0.001346 | 0.2816 | 0.4948 | 0.6811 | 0.7401 | 0.8103 | 0.2329 | 0.2500 | 0.2827 |
| 4 | Flue gas treatment | 0.03686 | 0.2448 | 0.4756 | 0.4885 | 0.7005 | 0.8103 | 0.05765 | 0.07142 | 0.09420 |
| 5 | Steam electric power generation | 0.01507 | 0.2011 | 0.4970 | 0.3003 | 0.6125 | 0.7856 | 0.02457 | 0.03448 | 0.04523 |
| 6 | Common resource supply | 0.8848e-4 | 0.1630 | 0.5628 | 0.1928 | 0.6014 | 0.8511 | 0.01296 | 0.01960 | 0.03331 |

FIG. 12

Table 2 Number of process variables selected based on comprehensive evaluation values

| Serial number | Statistics projects | | Boiler operation | Incineration treatment | Stack emission | Flue gas treatment | Steam electric power generation | Common resource supply | Total |
|---|---|---|---|---|---|---|---|---|---|
| 1 | Number of original features | | 14 | 79 | 6 | 20 | 53 | 115 | 287 |
| 2 | Correlation index | Correlation coefficient | 9 | 44 | 4 | 14 | 29 | 58 | 158 |
| | | Mutual information | 12 | 77 | 6 | 19 | 44 | 90 | 248 |
| | | Comprehensive evaluation value | 6 | 39 | 4 | 14 | 27 | 42 | 132 |
| 3 | Serial number | | 6 | 45 | 49 | 63 | 90 | 132 | -- |

FIG. 13

Table 3 Statistical RMSE results obtained by running the GAPLS algorithm 100 times

|  | Maximum values | Average values | Maximum values | Remarks |
|---|---|---|---|---|
| Training data | 0.005726 | 0.001359 | 4.3480e-8 |  |
| Testing data | 0.03110 | 0.02571 | 0.01853 |  |

FIG. 14

Table 4 Statistics number of times that process variables are selected based on multiple feature selection

| Serial number | Sub-processes | Number of times that variables are selected | Number of variables |
|---|---|---|---|
| 1 | Boiler operation | {12  7  12  7  22  8} | 6 |
| 2 | Incineration treatment | {13  9  13  13  9  7  18  14  9  13  23  21<br>3  3  10  21  33  9  0  10  7  11  29  3  11<br>4  8  12  5  5  7  16  11  6  9  9  12<br>28  6} | 39 |
| 3 | Stack emission | {2  6  0  5} | 4 |
| 4 | Flue gas treatment | {12  37  8  9  8  19  17  29  4  22  9  19<br>10  23} | 14 |
| 5 | Steam electric power generation | {37  10  11  17  18  27  26  23  20  16  8  20<br>11  11  15  13  11  11  18  18  14  23  13  32<br>18  44  10} | 27 |
| 6 | Common resource supply | {5  12  14  21  10  48  27  26  34  10  14  33<br>26  11  3  1  20  8  12  15  6  2  5  2<br>23  18  4  8  20  17  10  1  15  16  8  1<br>10  7  3  2  11  32} | 42 |

FIG. 15

| Table 5 Statistical process variables selected based on model prediction performance |||| 
|---|---|---|---|
| Serial number | Sub-processes | Number of times that variables are selected | Number of variables |
| 1 | Boiler operation | {'Oxygen concentration at a reactor inlet'} | 1/6 |
| 2 | Incineration treatment | {'Air flow at a right side of a combustion grate' 'Temperature of an outlet of a secondary air preheater' 'Air temperature of a drying grate inlet' 'Temperature at a side of an interior of a combustion grate 2-2' ' Temperature at the other side of an interior of a combustion grate 2-2' 'Air pressure at an outlet of a secondary fan' 'Speed at a side of a combustion grate'} | 7/39 |
| 3 | Stack emission | {--} | 0/4 |
| 4 | Steam electric power generation | {Water flow A in a mixer' 'Differential pressure A in a bag dust collector' 'Flue gas flow at a flue inlet' 'O2 concentration at an NID inlet' 'Feeding capacity of a lime storage bin' 'Supply flow of a urea solvent'} | 6/14 |
| 5 | Common resource supply | {'Pressure at an outlet of a coal economizer' 'Temperature of a circulating water inlet at a side A of a condenser' 'Temperature of a circulating water inlet at a side B of the condenser' 'Temperature of a circulating water outlet at the side B of the condenser' 'Temperature at an outlet of the condenser' '1# deaerator water level' 'Metal temperature of a thrust surface of a steam engine axial bearing pair' 'Temperature of a front bearing bush of an electric generator' 'Temperature of a rear bearing of a steam engine pinion gear' 'Vibration of the front bearing of a steam engine' 'Vibration of the rear bearing of the steam engine' 'Vibration of a front bearing of the electric generator'} | 13/27 |
| 6 | Common resource supply | {'Oil temperature 4 of a fuel tank' 'Pressure of a constant pressure water replenishing tank' 'Flow rate of compressed air in a main pipe of an instrument' '1# steam drum boiler water' '2# electric conductivity of the steam drum boiler water' 'Liquid level of a front pool of a rainwater sump pump' 'Liquid level of a water replenishing tank of a new integrated desulfurization (NID) system' 'Pressure of a first-stage steam extraction header' 'Pressure at an outlet of a temperature and pressure reducer in an air preheater' 'Temperature at an outlet of a bypass temperature and pressure reducer' '1# generator B phase current' '0# start/standby transformer 6kv side current'} | 12/42 |

FIG. 16

| Table 6 LV contribution rates of PLS models based on different input features |||||||||
|---|---|---|---|---|---|---|---|---|
| LV # | Process variables selected by data drive |||| Process variables selected by combining data drive and mechanism ||||
| | Input data || Output data || Input data || Output data ||
| | Single LV | Total | Single LV | Total | Single LV | Total | Single LV | Total |
| 1 | 29.62 | 29.62 | 55.18 | 55.18 | 29.23 | 29.23 | 56.00 | 56.00 |
| 2 | 26.96 | 56.58 | 21.95 | 77.13 | 28.15 | 57.38 | 11.55 | 67.54 |
| 3 | 9.97 | 66.55 | 15.90 | 93.04 | 9.68 | 67.05 | 14.26 | 81.81 |
| 4 | 7.15 | 73.70 | 3.92 | 96.96 | 7.31 | 74.36 | 6.48 | 88.29 |
| 5 | 2.60 | 76.31 | 2.06 | 99.01 | 7.50 | 81.86 | 2.37 | 90.65 |
| 6 | 7.47 | 83.78 | 0.26 | 99.27 | 4.40 | 86.26 | 1.80 | 92.45 |
| 7 | 3.70 | 87.48 | 0.22 | 99.49 | 5.14 | 91.39 | 0.59 | 93.04 |
| 8 | 2.94 | 90.42 | 0.16 | 99.65 | 3.14 | 94.53 | 0.86 | 93.90 |
| 9 | 1.51 | 91.93 | 0.20 | 99.85 | 1.65 | 96.18 | 1.85 | 95.75 |
| 10 | 2.96 | 94.89 | 0.06 | 99.90 | 1.22 | 97.40 | 1.34 | 97.09 |

FIG. 17

| Table 7 Statistical results of PLS models based on different input features ||||||||
|---|---|---|---|---|---|---|---|
| Serial number | Methods | Feature selection coefficient ($f_i^{corr}, f_i^{mi}, f_i^{corr\_mi}$), ($k_i^{corr}, k_i^{mi}$) | Input dimension | RMSE || Remarks Number of LV, data set ||
| | | | | Training | Testing | |
| 1 | PLS | -- | 287 | 0.01720 | 0.02004 | 2, Whole process |
| 2 | Correlation coefficient value-based PLS | (0.8,--,--),(1,--) | 153 | 0.01612 | 0.02015 | 2, Whole process |
| 3 | Mutual information value-based PLS | (--,0.8,--),(1,--) | 235 | 0.01764 | 0.02055 | 2, Whole process |
| 4 | Comprehensive evaluation value-based PLS | (0.8,0.8,0.8),(0.5,0.5) | 98 | 0.01649 | 0.02070 | 2, Data-drive, sub-processes |
| 5 | PLS in the present application | (0.8,0.8,0.8),(0.5,0.5) | 39 | 0.01375 | 0.01929 | 2, Data-drive + mechanism, sub-processes |
| | | (0.8,0.8,0.8),(0.5,0.5) | 18 | 0.01638 | 0.02048 | |

FIG. 18

METHOD FOR DETECTING A DIOXIN EMISSION CONCENTRATION OF A MUNICIPAL SOLID WASTE INCINERATION PROCESS BASED ON MULTI-LEVEL FEATURE SELECTION

CROSS-REFERENCE TO RELATED APPLICATIONS

This application is a continuation of International Patent Application No. PCT/CN2019/107216, filed on Sep. 23, 2019, which claims the benefit of priority from Chinese Patent Application No. 201910397710.5, filed on May 14, 2019. The content of the aforementioned applications, including any intervening amendments thereto, is incorporated herein by reference in its entirety.

TECHNICAL FIELD

The present application relates to complex industrial process parameter detection, and more particularly to a method for detecting a dioxin (DXN) emission concentration of a municipal solid waste incineration process based on multi-level feature selection.

BACKGROUND

Grate furnace-based municipal solid waste incineration (MSWI) is a widely used technique for household waste treatment and recycling[1-2]. As of 2017, there are 303 MSWI power plants in China, in which 220 MSWI power plants use the grate furnace. Most of the imported MSWI equipment is generally manually controlled during the operation, which causes unstable operation and failure to optimize the control[3]. In developing countries, there is an extremely urgent need to control pollutant emission caused by MSWI[4-5]. Dioxin (DXN) is a highly toxic pollutant[6] discharged from MSWI process and is the main cause of the "Not in my back yard" (NIMBY) effect. DXN, referred to as the most toxic pollutant in the century[7], is a general term for persistent organic pollutants composed of polychlorinated dibenzo-para-dioxins (PCDDs), polychlorinated dibenzofurans (PCDFs) and certain polychlorinated biphenyls with dioxin-like properties. DXN has a significant accumulation and amplification effect in organisms[8-9].

Currently, MSWI companies mainly focus on how to minimize DXN emissions by optimizing and controlling operating parameters[10], so it is necessary to realize online measurement of the DXN emission concentration so as to optimize the MSWI process. There are three typical detection methods for the DXN emission concentration: 1) an offline direct detection method, 2) an indicator/related substance online indirect detection method and 3) an online direct detection method. The first method requires a specialized laboratory and associated laboratory analysis equipment, having a lag time of month/week. The second method is performed through three steps. First, flue gas is collected online. Second, a concentration of the indicator/related substance is detected. Third, the DXN emission concentration is indirectly calculated based on a mapping model. In addition, the second method needs expensive and complicated online laboratory analysis equipment and has a lag time of day/hour. The third method does not require the laboratory analysis equipment and has a lag time of minute/second[11]. The present application mainly focuses the third method.

The online direct detection method of the DXN emission concentration is oriented toward input features selected based on mechanism and experience in the current research. Literatures[12-14] use small sample data of different types of incinerators and build models based on linear regression, artificial neural network (ANN), selective ensemble (SEN) least squares-support vector machine (LS-SVM), etc. Literature[15] uses data from more than four years of actual processes in an incineration plant in Taiwan, combines correlation analysis, principal component analysis (PCA) and artificial neural network (ANN), selects 13 variables from 23 readily detected process variables to establish a soft sensing DXN model, and concludes that the input features with a large contribution rate are injection frequency of activated carbon, a concentration of HCL gas emitted from a chimney and a temperature in a mixing chamber. Literature[16] adopts input variables, including a furnace temperature, a flue gas temperature at a boiler outlet, flue gas flow and concentrations of $SO_2$, HCL and particles, to establish a prediction model for the DXN emission concentration and toxicity equivalent based on support vector machine (SVM). Variables of the actual MSWI process have hundreds of dimensions, and are related to DXN generation, absorption and emission in different degrees[17]. However, none of the above processes performs feature selection by combining multi-phase characteristics of the MSWI process and the collinearity among these variables. In addition, labeled samples of DXN soft measurement are difficult to be obtained. Thus, feature selection of small sample high-dimensional data should be elevated to an important position during modeling.

The object of feature selection is to remove irrelevant and redundant features and retain only important features. In order to eliminate the irrelevant features, the degree of correlation between a single feature (independent variable) and the DXN emission concentration (dependent variable) in the MWSI process should be considered. Literature shortens the calculation time and simplifies the modeling by reducing the dimensionality of high-dimensional data via correlation coefficients. Literature[19] discloses a multi-objective semi-supervised feature selection method based on correlation coefficients. However, the linear method based on correlation coefficient proves to hardly describe the complex and arbitrary mapping relationship between the independent variable and the dependent variable[20]. Literature[21] points out that mutual information has good performance in characterizing the correlation between features. Literature[22] proposes a feature selection method based on individual optimal mutual information. Literature[23] proposes a feature selection method based on conditional mutual information, which can effectively evaluate previously selected features. It can be seen that both the correlation coefficient and the mutual information can characterize the correlation between the independent variable and the dependent variable[24-25]. The correlation coefficient focuses on linear relationships, while the mutual information focuses on nonlinear relationships[26-27]. For the actual complex industrial process, the mapping relationship between the independent variable and the dependent variable is difficulty characterized by only using a linear or non-linear relationship. Moreover, none of the above methods considers the approach of performing adaptive feature selection.

After obtaining a single input feature that has a good correlation with DXN, it is required to consider the redundancy among many process variables in the MSWI process, so as to eliminate the redundant features. Literature[28] expresses the redundancy between selected features and current features using the correlation coefficient. Literature[29] solves the problem of collinearity between variables by PCA, but the extracted latent variables can destroy the physical meaning of original features. Literature[30] solves multicollinearity by improving ridge regression. Literature[31] verifies that partial least squares (PLS) has good explanation and decomposition abilities for the multicollinearity between input features. Literature[32] proposes a feature selection method based on genetic algorithm-based partial least squares (GAPLS) algorithm. The feature selection method combines global optimization search capabilities of genetic algorithm (GA) and multicollinearity processing capabilities of PLS. Tang et al. disclose that GAPLS has good selectivity for high-dimensional spectral data[33], however, GA has randomness for small sample high-dimensional data, leading to different results for each feature selection. Therefore, it is necessary to perform statistics on the features selected multiple times to improve robustness and interpretability.

The above feature selection processes are performed based on data drive, and the limited sample size may produce deviations. Based on the existing research results and prior knowledge, there is need to augment the important features with clear mechanism meaning so as to make an online detection method more interpretable and in line with DXN emission characteristics of the MSWI process, thereby providing support for subsequent optimization control research.

FIG. 1 is a flow chart of a grate furnace-based MSWI process in a factory.

It can be seen from FIG. 1 that municipal solid waste (MSW) is collected by a specialized transport vehicle, transported to an unloading hall 1 and then dumped into a sealed storage tank 2. MSW is transferred to an incinerator feed hopper 4 by a manually controlled claw 3 and then is pushed into the grate furnace by a feeding machine. MSW in a grate 5 of the incinerator is subjected to drying, igniting, burning and afterflaming in sequence. Combustion residues fall into a water-cooled slag hopper and then are pushed into a slag tank 6 by a slag conveyor. After being collected, the combustion residues are sent to a landfill for treatment. The flue gas generated during incineration is converted to high-pressure steam by a waste-heat boiler to allow for power generation by a steam turbine set 7. The flue gas to be treated enters a reactor 8 from a boiler outlet for deacidification and neutralization reaction. Lime stored in a lime storage tank 9 and activated carbons stored in an activated carbon storage tank 10 are added into the reactor 8 for adsorbing DXN and heavy metals in the flue gas. In the reactor 8, flying ash falls on a bottom of the reactor 8, enters a flying ash storage bin 11 and then is taken away for harmless treatment. Flue gas enters a bag dust collector 12 for the removal of flue gas particles, neutralization reactants and activated carbon adsorbents. Partial ash mixture in the bag dust collector 12 enters a mixer 13 and then is mixed with water from a water tank 14 followed by re-entering the reactor 8. Exhaust gas at an end of the bag dust collector 12 is discharged into the atmosphere through a chimney 16 via a draft fan 15. The exhaust gas contains HCL, $SO_2$, $NO_x$, HF and DXN.

In the above process, DXN is present in incineration ash, the fly ash and the exhaust gas, where the amount of the incineration ash is largest. The amount of the fly ash is slightly smaller than that of the incineration ash. The DXN concentration of the incineration ash is relatively low. The DXN concentration of the fly ash is higher than that of the incineration ash. The DXN concentration of the exhaust gas is highest. The incineration ash and the fly ash require special treatment. The exhaust gas is of two types: incomplete garbage combustion-generated and synthesis reaction-generated[34]. In order to ensure that toxic organic matters are effectively decomposed, the flue gas temperature during the incineration should reach at least 850° C. and be kept fir at least 2 seconds. During the flue gas treatment, the lime and the activated carbon are injected into the reactor to remove acid gas and adsorb DXN and certain heavy metals, and then the flue gas is filtered by the bag dust collector and discharged into the chimney through the draft fan. In addition, a DXN memory effect in the flue gas treatment leads to an increase in the emission concentration. Generally, DXN generation and absorption-related process variables in the furnace incineration and flue gas treatment are stored in seconds by an on-site distributed control system. The concentration of readily detectable gases (CO, HCL, $SO_2$, $NO_x$, HF, etc.) in the exhaust gas is detected in real time by an online detection instrument. Incineration plants or environmental protection authorities usually perform the DXN concentration detection for the exhaust gas by an off-line direct detection method monthly or quarterly.

Accordingly, the DXN emission concentration online detection has the following difficulties. An original DXN content of MSW is unknown. The mechanism in the DXN generation and absorption stage is complicated and unclear. The DXN memory effect during the flue gas treatment leads to uncertainty in measurement. Therefore, it is very necessary to perform feature selection on input features for each sub-process of the MSWI process.

SUMMARY

In order to overcome the above-mentioned shortcomings in the prior art, the present application provides a method for detecting a dioxin (DXN) emission concentration in a MSWI process based on multi-level feature selection. Feature selection of input features is performed for each sub-process of the MSWI process, so as to detect the DXN emission concentration of the MSWI process. The method has good interpretability, conforms to DXN emission characteristics of the MSWI process and provides support for subsequent optimization control research.

The technical solutions of the present application are described as follows.

The present application provides a method for detecting a dioxin (DXN) emission concentration in a MSWI process based on multi-level feature selection, comprising:
1) dividing a grate furnace-based municipal solid waste incineration (MSWI) process into a plurality of sub-processes based on an incineration process; wherein the plurality of sub-processes comprise an incineration treatment sub-process, a boiler operation sub-process, a flue gas treatment sub-process, a steam electric power generation sub-process, a stack emission sub-process and a common resource supply sub-process;
2) obtaining a correlation coefficient value and a mutual information value between each of original input features of the sub-processes and the DXN emission concentration and obtaining a comprehensive evaluation value of candidate input features according to the obtained correlation coefficient value and the obtained mutual information value, thereby obtaining first-level features of all of the sub-processes;
3) selecting and statistically processing the first-level features by adopting a feature selection algorithm based on genetic algorithm-based partial least squares (GAPLS) and according to redundancy between different features, thereby obtaining second-level features of all of the sub-processes;

4) screening the first-level features and the second-level features based on statistical results within a preset threshold range, thereby obtaining the third-level features of all of the sub-processes; and 5) establishing a DXN detection model based on a partial least squares (PLS) algorithm according to model prediction performance and the third-level features; and detecting the DXN emission concentration by the obtained PLS algorithm-based DXN detection model.

In an embodiment, the method further comprises:
arranging the first-level features in series after the step of obtaining the first-level features of all of the sub-processes so as to obtain single feature correlation-based first-level features.

In an embodiment, the DXN detection model comprises input data and output data;
wherein the input data is expressed as $X \in R^{N \times P}$ and comprises N samples as row data and P variables as column data; the input data is derived from the sub-processes of the MSWI process; monitoring data of an i-th sub-process is obtained by using a programmable logic controller (PLC) device or a distributed control system (DCS) device installed on site and is expressed as $X_i \in R^{N \times P_i}$; and $X_i \in R^{N \times P_i}$ is input data from the i-th sub-process and satisfies Equations (1) and (2);

$$X = [X_1, \ldots, X_i, \ldots, X_I] = \{X_i\}_{i=1}^{I} \quad (1)$$

$$P = P_1 + \ldots + P_i + \ldots + P_I = \Sigma_{i=1}^{I} P_i \quad (2)$$

wherein I represents the number of the sub-processes, and $P_i$ represents the number of input features in the i-th sub-process;

$X_i$ is expressed as:

$$X_i = \left[ \{(x_n^1)_i\}_{n=1}^{N}, \ldots, \{(x_n^{p_i})_i\}_{n=1}^{N}, \ldots, \{(x_n^{P_i})_i\}_{n=1}^{N} \right] \quad (3)$$
$$= \left[ (x^1)_i, \ldots, (x^{p_i})_i, \ldots, (x^{P_i})_i \right]$$
$$= \{(x^{p_i})_i\}_{p_i=1}^{P_i}$$

wherein $(x^{p_i})_i$ represents a $p_i$-th input feature of the i-th sub-process; and $x^{p_i} = \{x_n^{p_i}\}_{n=1}^{N}$ represents a column vector; and wherein the output data is expressed as $y = \{y_n\}_{n=1}^{N} \in R^{N \times 1}$, and comprises N samples; and $\hat{y}$ represents a predicted value.

In an embodiment, the step of obtaining the correlation coefficient value comprises:

1.1) calculating an original correlation coefficient value between each of the original input features and the DXN emission concentration, wherein an original correlation coefficient value between a p-th input feature $(x^{p_i})_i = \{(x_n^{p_i})_i\}_{n=1}^{N}$ of the i-th sub-process and the DXN emission concentration is calculated according to $$(\xi_{corr\_ori}^{p_i})_i = \frac{\sum_{n=1}^{N} [((x_n^{p_i})_i - \bar{x}_{p_i})(y_n - \bar{y})]}{\sqrt{\sum_{n=1}^{N} ((x_n^{p_i})_i - \bar{x}_{p_i})^2} \sqrt{\sum_{n=1}^{N} (y_n - \bar{y})^2}} \quad (4)$$

wherein $\bar{x}_{p_i}$ represents an average value of the p-th input feature of the i-th sub-process; and $\bar{y}$ represents an average value of N modeling samples of the DXN emission concentration;

1.2) preprocessing the original correlation coefficient value as $(\xi_{corr\_ori}^{p_i})_i$ as follows:

$$(\xi_{corr}^{p_i})_i = |(\xi_{corr\_ori}^{p_i})_i| \quad (5)$$

wherein |•| represents an absolute value;

1.3) repeating steps (1.1)-(1.2) until correlation coefficient values of all of the original input features are obtained; and recording the obtained correlation coefficient values as $\{\xi_{corr}^{p_i}\}_{p_i=1}^{P_i}$;

1.4) setting a weight factor of the i-th sub-process as $f_i^{corr}$; calculating a threshold $\theta_i^{corr}$ configured to select input features based on the correlation coefficient values according to:

$$\theta_i^{corr} = f_i^{corr} \cdot \frac{1}{p_i} \sum_{p_i=1}^{P_i} (\xi_{corr}^{p_i})_i \quad (6)$$

wherein a maximum value $(f_i^{corr})_{max}$ and a minimum value $(f_i^{corr})_{min}$ of $f_i^{corr}$ are calculated according to Equation (7):

$$\begin{cases} (f_i^{corr})_{max} = \dfrac{\max((\xi_{corr}^{1})_i, \ldots, (\xi_{corr}^{p_i})_i, \ldots, (\xi_{corr}^{P_i})_i)}{\dfrac{1}{p_i} \sum_{p_i=1}^{P_i} (\xi_{corr}^{p_i})_i} \\[2ex] (f_i^{corr})_{min} = \dfrac{\min((\xi_{corr}^{1})_i, \ldots, (\xi_{corr}^{p_i})_i, \ldots, (\xi_{corr}^{P_i})_i)}{\dfrac{1}{p_i} \sum_{p_i=1}^{P_i} (\xi_{corr}^{p_i})_i} \end{cases} \quad (7)$$

wherein max (•) is a function for finding a maximum value; and min(•) is a function for finding a minimum value;

1.5) selecting the p-th input feature of the i-th sub-process according to rules as follows:

$$\alpha_i^{p_i} = \begin{cases} 1, & \text{if } (\xi_{corr}^{p_i})_i \geq \theta_i^{corr} \\ 0, & \text{else } (\xi_{corr}^{p_i})_i < \theta_i^{corr} \end{cases} \quad (8)$$

wherein $\theta_i^{corr}$ is taken as a threshold;

1.6) selecting a feature $(x^{p_i})_i$ in $\alpha_i^{p_i} = 1$ as a correlation coefficient-selected candidate feature; and recording the correlation coefficient-selected candidate feature as $$\left( x^{(p_i)sel}_{corr} \right)_i;$$

1.7) performing steps (1.1)-(1.6) for all of the original input features of the i-th sub-process; and recording the selected candidate features as:

$$(x_{corr}^{sel})_i = \left[ (x^1)_i, \ldots, \left( x^{(p_i)sel}_{corr} \right)_i, \ldots, \left( x^{(P_i)sel}_{corr} \right)_i \right] \quad (9)$$

wherein $(P_i)_{corr}^{sel}$ represents the number of correlation coefficient-selected process variables of the i-th sub-process; and $(X_{corr}^{sel})_i$ represents a correlation coefficient-selected candidate feature set selected from the input features of the i-th sub-process; and 1.8) repeating steps (1.1)-(1.7) for all the sub-processes; and recording correlation coefficient measurement-selected features as $\{(X_{corr}^{sel})_i\}_{i=1}^{I}$.

In an embodiment, the step of obtaining the mutual information value comprises:

2.1) calculating a mutual information value between each of the original input features and the DXN emission concentration, wherein a mutual information value between the p-th input feature $(x^{p_i})_t$ of the i-th sub-process and the DXN emission concentration is calculated according to $$(\xi_{mi}^{p_i})_i = \sum_{n=1}^{N}\sum_{n=1}^{N}\left\{p_{rob}((x_n^{p_i})_i, y_n)\log\left(\frac{p_{rob}((x_n^{p_i})_i, y_n)}{p_{rob}((x_n^{p_i})_i)P_{rob}(y_n)}\right)\right\} \quad (10)$$

wherein $p_{rob}((x_n^{p_i})_i, y_n)$ represents a joint probability density, and $P_{rob}((x_n^{p_i})_i)$ and $p_{rob}(y_n)$ each represent a marginal probability density;

2.2) repeating step (2.1) until mutual information values of all of the original input features are obtained; and recording the obtained mutual information values as $\{\xi_{mi}^{p_i}\}_{P_i=1}^{P_i}$;

2.3) setting a weight factor of the i-th sub-process as $f_i^{mi}$, and calculating a threshold $\theta_i^{mi}$ configured to select the input features based on the mutual information value according to $$\theta_i^{mi} = f_i^{mi} \cdot \frac{1}{p_i}\sum_{p_i=1}^{P_i}(\xi_{mi}^{p_i})_i \quad (11)$$

wherein a maximum value $(f_i^{mi})_{max}$ and a minimum value $(f_i^{mi})_{min}$ of $f_i^{mi}$ are calculated according to $$\begin{cases}(f_i^{mi})_{max} = \dfrac{\max\left((\xi_{mi}^1)_i, \ldots, (\xi_{mi}^{p_i})_i, \ldots, (\xi_{mi}^{P_i})_i\right)}{\frac{1}{p_i}\sum_{p_i=1}^{P_i}(\xi_{mi}^{p_i})_i} \\ (f_i^{mi})_{min} = \dfrac{\min\left((\xi_{mi}^1)_i, \ldots, (\xi_{mi}^{p_i})_i, \ldots, (\xi_{mi}^{P_i})_i\right)}{\frac{1}{p_i}\sum_{p_i=1}^{P_i}(\xi_{mi}^{p_i})_i}\end{cases} \quad (12)$$

wherein $\max(\cdot)$ is a function for finding a maximum value; and $\min(\cdot)$ is a function for finding a minimum value;

2.4) selecting the p-th input feature of the i-th sub-process according to rules as follows:

$$\beta_i^{p_i} = \begin{cases}1, & \text{if } (\xi_{mi}^{p_i})_i \geq \theta_i^{mi} \\ 0, & \text{else } (\xi_{mi}^{p_i})_i < \theta_i^{mi}\end{cases} \quad (13)$$

wherein $\theta_i^{mi}$ is taken as a threshold;

2.5) selecting a feature $(x^{p_i})_i$ of $\beta_i^{p_i}=1$ as a mutual information value-selected candidate feature; recording the mutual information value-selected candidate feature as $$\left(x^{(p_i)_{mi}^{sel}}\right)_i;$$

2.6) performing steps (2.1)-(2.5) for all of the input features of the i-th sub-process; and recording the selected candidate features as:

$$(x_{mi}^{sel})_i = \left[(x^1)_i, \ldots, \left(x^{(p_i)_{mi}^{sel}}\right)_i, \ldots, \left(x^{(P_i)_{mi}^{sel}}\right)_i\right] \quad (14)$$

wherein $(P_i)_{mi}^{sel}$ represents the number of mutual information value-selected features in the i-th sub-process; and $(X_{mi}^{sel})_i$ represents a candidate feature set selected using mutual information value measurement from the input features of the i-th sub-process; and 2.7) repeating steps (2.1)-(2.6) for all the sub-processes; and recording mutual information value measurement-selected features as $\{(X_{mi}^{sel})_t\}_{t=1}^{I}$.

In an embodiment, the step of obtaining the comprehensive evaluation value comprises:

3.1) for the i-th sub-process, taking the intersection of the mutual information-selected features $(X_{mi}^{sel})_t$ and the correlation coefficient-selected features $(X_{corr}^{sel})_i$ according to Equation (15), thereby obtaining a comprehensive evaluation value-selected candidate feature set, $$(X_{corr\_mi}^{sel})_i = \quad (15)$$
$$(X_{mi}^{sel})_i \cap (X_{corr}^{sel})_i = \left[(x^1)_i, \ldots, \left(x^{(p_i)_{corr\_mi}^{sel}}\right)_i, \ldots, \left(x^{(P_i)_{corr\_mi}^{sel}}\right)_i\right]$$

wherein $\cap$ represents the intersection;

$$x^{(p_i)_{corr\_mi}^{sel}}$$

represents a $(p_i)_{cor\_mi}^{sel}$-th candidate feature of the i-th sub-process; and a correlation coefficient value of the $(p_i)_{corr\_mi}^{sel}$-th candidate feature is $$\left(\xi_{corr}^{(p_i)_{corr\_mi}^{sel}}\right)_i;$$

and a mutual information value of the $(p_i)_{corr\_mi}^{sel}$-th candidate feature is $$\left(\xi_{mi}^{(p_i)_{corr\_mi}^{sel}}\right)_i;$$

3.2) performing normalization according to Equations (16) and (17) so as to eliminate size differences of the correlation coefficient value and mutual information value of the different input features;

$$\left(\zeta_{corr\_norm}^{(p_i)_{corr\_mi}^{sel}}\right)_i = \frac{\left(\zeta_{corr}^{(p_i)_{corr\_mi}^{sel}}\right)_i}{\sum_{(p_i)_{corr\_mi}^{sel}=1}^{(P_i)_{corr\_mi}^{sel}} \left(\zeta_{corr}^{(p_i)_{corr\_mi}^{sel}}\right)_i} \quad (16)$$

$$\left(\zeta_{mi\_norm}^{(p_i)_{corr\_mi}^{sel}}\right)_i = \frac{\left(\zeta_{mi}^{(p_i)_{corr\_mi}^{sel}}\right)_i}{\sum_{(p_i)_{corr\_mi}^{sel}=1}^{(P_i)_{corr\_mi}^{sel}} \left(\zeta_{mi}^{(p_i)_{corr\_mi}^{sel}}\right)_i} \quad (17)$$

wherein $$\left(\zeta_{corr\_norm}^{p_{corr\_mi}^{sel}}\right)_i$$

represents a standardized correlation coefficient value of the $p_{corr\_mi}^{sel}$-th candidate feature of the i-th sub-process; and $$\left(\zeta_{mi\_norm}^{p_{corr\_mi}^{sel}}\right)_i$$

represents a standardized mutual information value of the $p_{corr\_mi}^{sel}$-th candidate feature of the i-th sub-process;

3.3) defining a comprehensive evaluation value of the candidate input features as $$\zeta_i^{(p_i)_{corr\_mi}^{sel}},$$

expressing $$\zeta_i^{(p_i)_{corr\_mi}^{sel}}$$

as $$\zeta_{corr\_mi}^{(p_i)_{corr\_mi}^{sel}} = k_i^{corr} \cdot \zeta_{corr\_norm}^{(p_i)_{corr\_mi}^{sel}} + k_i^{mi} \cdot \zeta_{mi\_norm}^{(p_i)_{corr\_mi}^{sel}} \quad (18)$$

wherein $k_i^{corr}$ and $k_i^{mi}$ each represent a proportional coefficient; and $k_i^{corr}+k_i^{mi}=1$; and 3.4) repeating steps (3.1)-(3.3) until comprehensive evaluation values of all of the candidate input features are obtained; and recording the obtained comprehensive evaluation values as $$\left\{\zeta_{corr\_mi}^{(p_i)_{corr\_mi}^{sel}}\right\}_{(p_i)_{corr\_mi}^{sel}=1}^{(P_i)_{corr\_mi}^{sel}}.$$

In an embodiment, $k_i^{corr}$ is equal to 0.5; and $k_i^{mi}$ is equal to 0.5.

In an embodiment, the step of obtaining the comprehensive evaluation value of the candidate input features according to the correlation coefficient value and the mutual information value comprises:

4.1) setting a weight factor of the i-th sub-process as $f_i^{corr\_mi}$; calculating a threshold $\theta_i^{1stsel}$ configured to select the input features based on the comprehensive evaluation value according to $$\theta_i^{1stsel} = f_i^{corr\_mi} \frac{1}{(P_i)_{corr\_mi}^{sel}} \sum_{(p_i)_{corr\_mi}^{sel}=1}^{(P_i)_{corr\_mi}^{sel}} \left(\zeta_{corr\_mi}^{(p_i)_{corr\_mi}^{sel}}\right)_i \quad (19)$$

wherein a maximum value $(f_t^{corr\_mi})_{max}$ and a minimum value $(f_t^{corr\_mi})_{min}$ of $f_i^{corr\_mi}$ are calculated according to $$\begin{cases} (f_i^{corr\_mi})_{max} = \dfrac{\max\left((\zeta_{corr\_mi}^1)_i, \ldots, (\zeta_{corr\_mi}^{(p_i)_{corr\_mi}^{sel}})_i, \ldots, (\zeta_{corr\_mi}^{(p_i)_{corr\_mi}^{sel}})_i\right)}{\dfrac{1}{(P_i)_{corr\_mi}^{sel}} \sum_{(p_i)_{corr\_mi}^{sel}=1}^{(P_i)_{corr\_mi}^{sel}} \left(\zeta_{corr\_mi}^{(p_i)_{corr\_mi}^{sel}}\right)_i} \\ (f_i^{corr\_mi})_{min} = \dfrac{\min\left((\zeta_{corr\_mi}^1)_i, \ldots, (\zeta_{corr\_mi}^{(p_i)_{corr\_mi}^{sel}})_i, \ldots, (\zeta_{corr\_mi}^{(p_i)_{corr\_mi}^{sel}})_i\right)}{\dfrac{1}{(P_i)_{corr\_mi}^{sel}} \sum_{(p_i)_{corr\_mi}^{sel}=1}^{(P_i)_{corr\_mi}^{sel}} \left(\zeta_{corr\_mi}^{(p_i)_{corr\_mi}^{sel}}\right)_i} \end{cases} \quad (20)$$

4.2) selecting a $(p_i)_{corr\_mi}^{sel}$-th candidate input feature of the i-th sub-process according to rules as follows:

$$\gamma^{(p_i)_{corr\_mi}^{sel}} = \begin{cases} 1, & \text{if } \zeta_{corr\_mi}^{(p_i)_{corr\_mi}^{sel}} \geq \theta_i^{1stsel} \\ 0, & \text{if } \zeta_{corr\_mi}^{(p_i)_{corr\_mi}^{sel}} < \theta_i^{1stsel} \end{cases} \quad (21)$$

wherein $\theta_i^{1stsel}$ is taken as a threshold;

4.3) performing steps (4.1)-(4.2) for all the original candidate input features; selecting variables of $$\gamma^{(p_i)_{corr\_mi}^{sel}} = 1$$

as comprehensive evaluation value-selected input feature; and expressing the variables as:

$$(X_{1st}^{sel})_i = \left[(x^1)_i, \ldots, (x^{p_i^{sel}})_i, \ldots, (x^{p_i^{sel}})_i\right] \quad (22)$$

wherein $(X_{1st}^{sel})_i$ represents first-level features of the i-th sub-process selected using a comprehensive evaluation value measurement from the candidate feature set selected by a correlation coefficient method and a mutual information method; and 4.4) repeating steps (4.1)-(4.3) until the first-level features of all the sub-processes is obtained.

In an embodiment, the step of arranging the first-level features in series comprises:
arranging the first-level features in series to obtain the first-level features $X_{1st}^{sel}$ based on the single feature correlation;

$$X_{1st}^{sel} = [(X_{1st}^{sel})_1, \ldots, (X_{1st}^{sel})_i, \ldots, (X_{1st}^{sel})_I] = [x^{1_{st}^{sel}}, \ldots, x^{p_{1st}^{sel}}, \ldots, x^{P_{1st}^{sel}}] \quad (23)$$

wherein $$x^{p_{1st}^{sel}}$$

represents a $p_{1st}^{sel}$-th feature in a first-level feature selection set;

$$P_{1st}^{sel}1 = \sum_{i=1}^{I} P_i^{sel}$$

represents the number of all of the first-level features; and $X_{1st}^{sel}$ represents single feature correlation-based first-level feature obtained by serially combining the first-level features of all of the sub-processes.

In an embodiment, a strategy of selecting the second-level features comprises:
inputting the first-level features $X_{1st}^{sel}$; running the GAPLS algorithm J times; outputting the second-level features $(X_{2nd}^{sel})_j$ and then outputting the number of times that the respective first-level input features are selected; and statistically processing the second-level features that are selected $J_{sel}$ times, wherein when a GAPLS model prediction error is smaller than a prediction error average obtained by running the GAPLS algorithm J times, a second-level feature is selected; recording the number of times that a $p_{1st}^{sel}$-th feature is selected as $$f_{num}^{p_{1st}^{sel}};$$

accordingly, recording all $p_{1st}^{sel}$-th features of the first-level features as $$\left\{ f_{num}^{p_{jel}^{sel}} \right\}_{p_{1st}^{sel}=1}^{P_{1st}^{sel}};$$

wherein J is the number of times that the GAPLS algorithm runs; $J_{sel}$ is the number of GAPLS models, prediction errors of which are smaller than a prediction error average; and $(X_{2nd}^{sel})_j$ represents multiple feature redundancy-based second-level features selected by jth run the GAPLS algorithm.

In an embodiment, the step of selecting the second-level features comprises:
5.1) setting the number of times that the GAPLS algorithm runs as J; setting GAPLS algorithm parameters; initializing a population size, maximum genetic algebra, mutation probability, a crossover method and a number of latent variables of the PLS algorithm; and setting j=1 and starting the selection of the second-level features;
5.2) determining whether the GAPLS algorithm J times; if yes, proceeding to step (5.11); if no, proceeding to step (5.3);
5.3) performing binary encoding for features, wherein a length of a chromosome is the number of input features; 1 implies that a feature is selected; and 0 implies that no feature is selected;
5.4) performing random initialization on population;
5.5) evaluating the fitness of the population; and calculating a root mean square error of cross-validation (RMSECV) using a leave-one-out cross-validation method;
5.6) determining whether a termination condition of the maximum genetic algebra is reached, if no, proceeding to step (5.7); if yes, proceeding to step (5.9);
5.7) performing genetic operations comprising selection, crossover and variation, wherein the selection is performed through an elite substitution strategy, that is, individuals with poor fitness are replaced with individuals with good fitness; the crossover is performed through single point crossover; and the genetic variation is performed through single point mutation;
5.8) obtaining a new population and proceeding to step (5.5);
5.9) obtaining an optimal individual after running the GAITS algorithm J times; and performing decoding to obtain selected second-level features and recording the selected second-level features as $(X_{2nd}^{sel})_j$;
5.10) setting j=j+1; and proceeding to step (5.2);
5.11) calculating an average value of root mean square errors (RMSE) of a prediction model obtained by running the GAPLS algorithm J times; recording the number of the root mean square errors of the GAPLS model that are larger than the average value as $J_{sel}$; processing the second-level features that are selected $J_{sel}$ times by counting the number of times that the $P_{1st}^{sel}$-th feature in the first-level features is selected, $$\left\{ (X_{2nd}^{sel})_j \right\}_{j=1}^{J_{sel}} \Rightarrow \left\{ f_{num}^{1_{st}^{sel}}, \ldots, f_{num}^{p_{1st}^{sel}}, \ldots, f_{num}^{P_{1st}^{sel}} \right\} = \left\{ f_{num}^{p_{1st}^{sel}} \right\}_{p_{1st}^{sel}=1}^{P_{1st}^{sel}}, \quad (24)$$

$$1 \leq f_{num}^{p_{1st}^{sel}} \leq J_{sel}$$

wherein $$f_{num}^{p_{1st}^{sel}}$$

is the number of times that the $p_{1st}^{sel}$-th feature in the first-level features is selected.

In an embodiment, the population size is 20; the maximum genetic algebra is 40; a maximum number of latent variables of the PLS algorithm is 6; and the mutation probability is 0.005.

In an embodiment, the step of selecting the third-level features comprises:
according to the number of times $$\left\{ f_{num}^{p_{1st}^{sel}} \right\}_{p_{1st}^{sel}=1}^{P_{1st}^{sel}}$$

that all the $p_{1st}^{sel}$-th features in the first-level features are selected, setting a scale factor as $f_{DXN}^{RMSE}$; determining a lower limit of a threshold configured to select the third-level features as $\theta_{DXN}^{downlimit}$; calculating $\theta_{DXN}^{downlink}$ according to:

$$\theta_{DXN}^{downlimit} = \text{floor}\left(f_{DXN}^{RMSE} \cdot \frac{1}{P_{1st}^{sel}} \sum_{p_{1st}^{sel}=1}^{P_{1st}^{sel}} f_{num}^{p_{1st}^{sel}}\right) \quad (25)$$

wherein floor(•) represents a function that returns integers;

calculating a maximum value $(f_{DXN}^{RMSE})_{max}$ and a minimum value $(f_{DXN}^{RMSE})_{min}$ of $f_{DXN}^{RMSE}$ according to $$\begin{cases} (f_{DXN}^{RMSE})_{max} = \dfrac{\max\left(f_{num}^{1_{st}^{sel}}, \ldots, f_{num}^{p_{1st}^{sel}}, \ldots, f_{num}^{P_{1st}^{sel}}\right)}{\dfrac{1}{P_{1st}^{sel}} \sum_{p_{1st}^{sel}=1}^{P_{1st}^{sel}} f_{num}^{p_{1st}^{sel}}} \\ (f_{DXN}^{RMSE})_{min} = \dfrac{\min\left(f_{num}^{1_{st}^{sel}}, \ldots, f_{num}^{p_{1st}^{sel}}, \ldots, f_{num}^{P_{1st}^{sel}}\right)}{\dfrac{1}{P_{1st}^{sel}} \sum_{p_{1st}^{sel}=1}^{P_{1st}^{sel}} f_{num}^{p_{1st}^{sel}}} \end{cases} \quad (26)$$

finding a maximum value of the number of times that all the $p_{1st}^{sel}$-th features in the first-level features are selected based on an upper limit $\theta_{DXN}^{uplimit}$ of the threshold, $$\theta_{DXN}^{uplimit} = \max\left(f_{num}^{1_{st}^{sel}}, \ldots, f_{num}^{p_{1st}^{sel}}, \ldots, f_{num}^{P_{1st}^{sel}}\right) \quad (27)$$

recording the threshold configured to select the third-level features as $\theta_{DXN}^{3rd}$, wherein the threshold $\theta_{DXN}^{3rd}$ is between $\theta_{DXN}^{downlimit}$ and $\theta_{DXN}^{uplimit}$; and obtaining the third-level features according to $$\mu^p = \begin{cases} 1, & \text{if } f_{num}^{p_{1st}^{sel}} \geq \theta_{DXN}^{3rd} \\ 0, & \text{else } f_{num}^{p_{1st}^{sel}} < \theta_{DXN}^{3rd} \end{cases} \quad (28)$$

wherein $f_{num}^{p_{1st}^{sel}}$ represents the number of times that the $p_{1st}^{sel}$-th feature in the first-level features is selected by running the GAPLS algorithm J times; $\mu^p$ represents a threshold selection criterion for selecting the third-level features;

sequentially storing feature variables of $\mu^p=1$ in $X_{3rd}^{sel\_temp}$, and calculating the RMSE, wherein $X_{3rd}^{sel\_temp}$ serves as input variables in the establishment of the PLS algorithm-based DXN detection model; and $X_{3rd}^{sel}$ represents the third-level features selected from $X_{1st}^{sel}$ based on a feature selection threshold $\theta_{3rd}$ and prior knowledge.

In an embodiment, the step of establishing the PLS algorithm-based DXN detection model comprises;

increasing values of the threshold $\theta_{DXN}^{3rd}$ between $\theta_{DXN}^{downlimit}$ and $\theta_{DXN}^{uplimit}$ one by one; so as to establish a plurality of first temporary PLS algorithm-based DXN detection models;

selecting a second temporary PLS algorithm-based DXN detection model from the plurality of first temporary PLS algorithm-based DXN detection models, wherein the second temporary PLS algorithm-based DXN detection model has a minimum value of RMSE;

checking the input features of the DXN emission concentration detection model to determine whether the input features comprise concentrations of CO, HCL, $O_2$ and $NO_x$ emitted from a chimney; and removing features in the common resource supply sub-process; if the input features do not include concentrations of CO, HCL, $O_2$ and $NO_x$, additionally selecting the third-level features to obtain selected three-level features $x_{rd}^{sel}$, thereby varying the number of features that are selected and establishing the PLS algorithm-based DXN detection model based on prior knowledge.

In an embodiment, variables of the PLS algorithm-based DXN detection model have 287 dimensions.

In an embodiment, weight factors $f_i^{corr}$, $f_i^{mi}$ and $f_i^{corr\_mi}$ of feature selection of the correlation coefficient value and the mutual information value of the first-level features are 0.8.

In an embodiment, there are 132 feature variables selected by the comprehensive evaluation value; for the selected 132 process variables based on the single feature correlation, an optimal process variable combination is determined using the GAPLS algorithm so as to remove redundant features.

The present application has the following beneficial effects.

In the method of the present application, feature selection of input features is performed for each sub-process of the MSWI process, so as to detect the DXN emission concentration of the MSWI process based on multi-level feature selection. The method has good interpretability, conforms to DXN emission characteristics of the MSWI process and provides support for subsequent optimization control research.

BRIEF DESCRIPTION OF THE DRAWINGS

The present application will be further described below with reference to the accompanying drawings, so that the present application is more understandable. The accompanying drawings disclosed herein are merely illustrative and not intended to limit the present application.

FIG. 12 is a table showing correlation measurement results of process variables of different sub-processes according to an embodiment of the present application.

FIG. 13 is a table showing the number of process variables selected based on the comprehensive evaluation values according to an embodiment of the present application.

FIG. 14 is a table of statistical RMSE results obtained by running the GAPLS algorithm J times according to an embodiment of the present application.

FIG. 15 is a table showing the number of times that process variables are selected based on multiple feature selection according to an embodiment of the present application.

FIG. 16 is a table showing process variable selected based on model prediction performance according to an embodiment of the present application.

FIG. 17 is a table showing LV contribution rates of PLS models based on different input features according to an embodiment of the present application.

FIG. 18 is a table showing statistical results of the PLS models based on different input features according to an embodiment of the present application.

Figure 1:
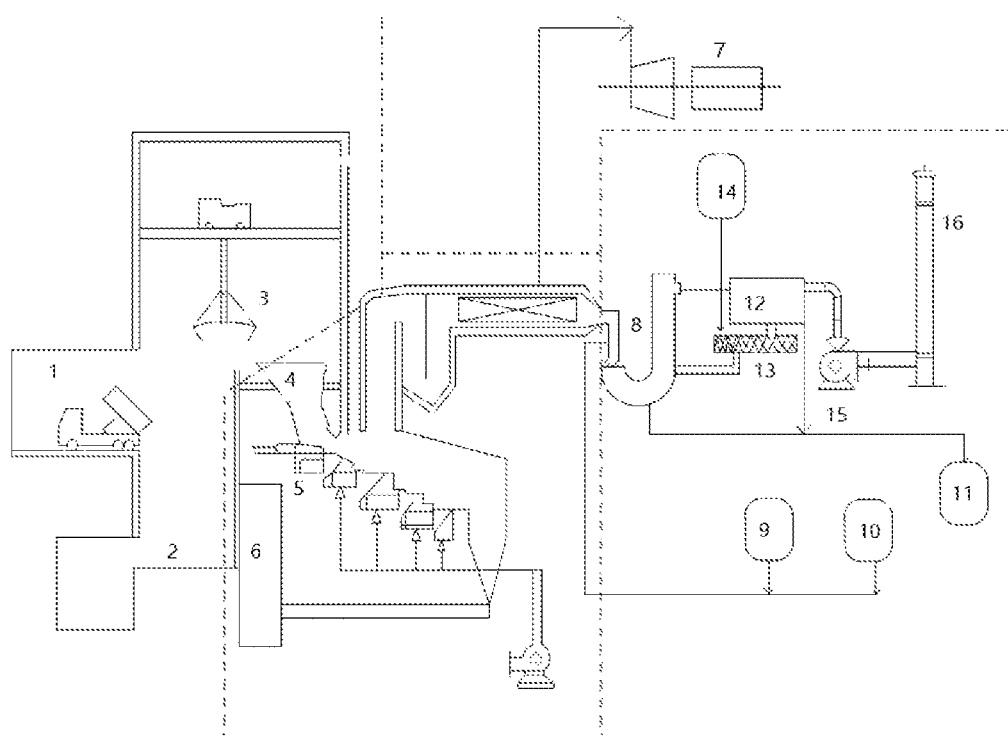
FIG. 1 is a flowchart illustrating a grate furnace-based MSWI process.

In the drawings: 1, unloading hall; 2, storage tank; 3, claw; 4, incinerator feed hopper; 5, grate; 6, slag tank; 7, steam turbine set; 8, reactor; 9, lime storage tank; 10, activated carbon storage tank; 11, fly ash storage bin; 12, bag dust collector; 13, mixer; 14, water tank; 15, draft fan; and 16, chimney.

DETAILED DESCRIPTION OF EMBODIMENTS

The present application will be further described below with reference to the accompanying drawings to clearly and completely illustrate the technical solutions of the embodiments. It is apparent that the embodiments below are merely preferred embodiments of the present application and are not intended to limit the invention. Any other embodiments made by those skilled in the art based on the embodiments disclosed herein without sparing any creative efforts should fall within the scope of the invention.

Figure 2:
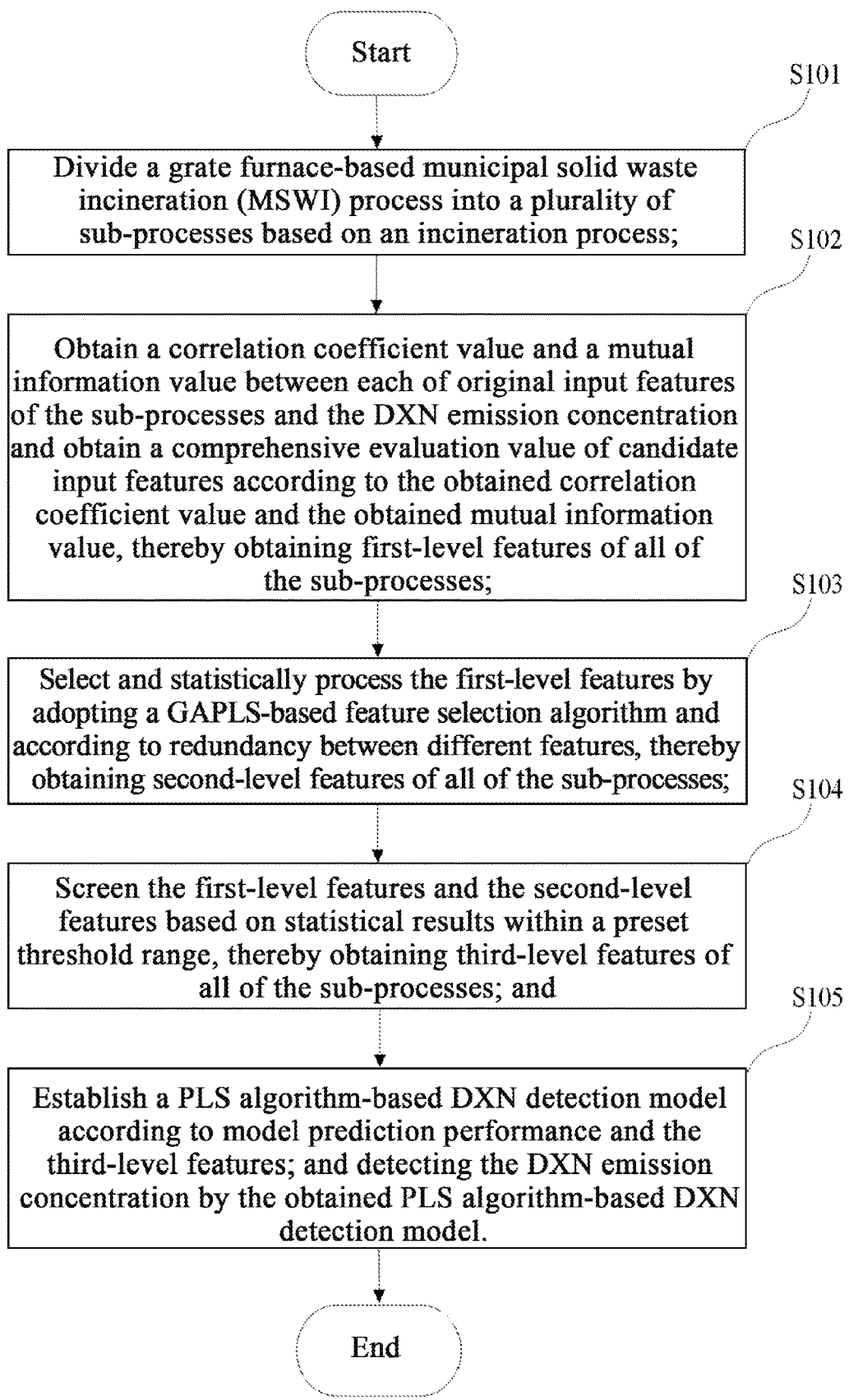
FIG. 2 is a flowchart of a method for detecting a DXN emission concentration in a MSWI process based on multi-level feature selection according to an embodiment of the present application.

FIG. 2 shows a flowchart illustrating a method for detecting a DXN emission concentration in a MSWI process based on multi-level feature selection according to an embodiment of the present application.

The method includes the following steps.

S101) A grate furnace-based municipal solid waste incineration (MSWI) process is divided into a plurality of sub-processes based on incineration process. The plurality of sub-processes include an incineration treatment sub-process, a boiler operation sub-process, a flue gas treatment sub-process, a steam electric power generation sub-process, a stack emission sub-process and a common resource supply sub-process.

S102) A correlation coefficient value and a mutual information value between each of original input features of the sub-process and the DXN emission concentration are obtained. Then a comprehensive evaluation value of candidate input features is obtained according to the obtained correlation coefficient value and the obtained mutual information value, thereby obtaining first-level features of all of the sub-processes.

S103) The first-level features are selected and statistically processed by adopting a GAPLS-based feature selection algorithm and according to redundancy between different features, thereby obtaining second-level features of all of the sub-processes.

S104) The first-level features and the second-level features are screened based on statistical results within a preset threshold range, thereby obtaining the third-level features of all of the sub-processes S105) A DXN detection model based on a partial least squares (PLS) algorithm is obtained according to model prediction performance and the third-level features. The DXN emission concentration is detected by the obtained PLS algorithm-based DXN detection model.

Specifically, the goal of feature selection in the present application is to improve the prediction performance and interpretability of a soft sensing model. The concentration detection method of the present application belongs to environmental protection fields, particularly to complex industrial process parameter detection. In the present embodiment, a method for detecting a dioxin (DXN) emission concentration in a MSWI process based on multi-level feature selection is provided. Firstly, from the perspective of the correlation between a single input feature and the DXN emission concentration, a comprehensive evaluation value index is constructed by combining the correlation coefficient and the mutual information, so as to realize the first-level feature selection of process variables of a monitored sub-process in the MSWI process. Secondly, from the perspective of multiple feature redundancy and feature selection robustness, running the GAPLS-based feature selection algorithm multiple times is performed to achieve the second-level feature selection based on the selected first-level features. Finally, by the combination of the number of times that previously selected features are selected, the model prediction performance and mechanism, the third-level feature selection is achieved based on the selected second-level features. The DXN emission concentration detection model can be established based on the obtained features. The method provided herein is verified to be effective by multi-year DXN monitoring data of an incineration plant.

Compared to the prior art, in the method of the present embodiment, feature selection of input features is performed for each sub-process of the MSWI process, so as to detect the DXN emission concentration of the MSWI process. The method has good interpretability, conforms to DXN emission characteristics of the MSWI process and provides support for subsequent optimization control research.

Specifically, the method further includes a step of arranging the first-level features in series after obtaining the first-level features of a 1 of the sub-processes, so as to obtain the first-level features based on single feature correlation.

Specifically, the DXN detection model includes input data and output data.

The input data is expressed as $X \in R^{N \times P}$ and includes N samples as row data and P variables as column data. The input data is derived from respective sub-processes of the MSWI process. Monitoring data of an i-th sub-process is obtained by using a programmable logic controller (PLC) device or a distributed control system (DCS) device installed on site and is expressed as $X_i \in R^{N \times P_i}$. $X_i \in R^{N \times P_i}$ is input data from the i-th sub-process and satisfies Equations (1) and (2):

$$X = [X_1, \ldots, X_p, \ldots, X_I] = \{X_i\}_{i=1}^{I} \tag{1}$$

$$P = P_1 + \ldots + P_i + \ldots + P_I = \Sigma_{i=1}^{I} P_i \tag{2}$$

where I represents the number of the sub-processes, and $P_i$ represents the number of the input features in the i-th sub-process;

$X_i$ is expressed as:

$$X_i = \left[ \{(x_n^1)_i\}_{n=1}^N, \ldots, \{(x_n^{p_i})_i\}_{n=1}^N, \ldots, \{(x_n^{P_i})_i\}_{n=1}^N \right] \tag{3}$$

$$= [(x^1)_i, \ldots, (x^{p_i})_i, \ldots, (x^{P_i})_i]$$

$$= \{(x^{p_i})_i\}_{p_i=1}^{P_i}$$

where $(x^{p_i})_i$ represents a $p_i$-th input feature of the i-th sub-process; and $x^{p_i} = \{x_n^{p_i}\}_{n=1}^N$ represents a column vector.

The output data is expressed as $y = \{y_n\}_{n=1}^N \in R^{N \times 1}$ and includes N samples; and $\hat{y}$ represents a predicted value.

Specifically, the step of obtaining the correlation coefficient value is performed through the following steps.

1.1) An original correlation coefficient value between each of the original input features and the DXN emission concentration is calculated. For example, an original correlation coefficient value between a p-th input feature $(x^{p_i})_i = \{(x_n^{p_i})_i\}_{n=1}^N$ of the i-th sub-process and the DXN emission concentration is calculated according to $$(\xi_{corr\_ori}^{p_i})_i = \frac{\sum_{n=1}^{N} [((x_n^{p_i})_i - \bar{x}_{p_i})(y_n - \bar{y})]}{\sqrt{\sum_{n=1}^{N} ((x_n^{p_i})_i - \bar{x}_{p_i})^2} \sqrt{\sum_{n=1}^{N} (y_n - \bar{y})^2}} \tag{4}$$

where $\bar{x}_{p_i}$ represents an average value of the p-th input feature of the i-th sub-process; and $\bar{y}$ represents an average value of N modeling samples of the DXN emission concentration.

1.2) The original correlation coefficient value $(\xi_{corr\_ori}^{p_i})_i$ is preprocessed as follows:

$$(\xi_{corr}^{p_i})_i = |(\xi_{corr\_ori}^{p_i})_i| \tag{5}$$

where |•| represents an absolute value.

1.3) Steps (1.1)-(1.2) are repeated until correlation coefficients of all of the original input features are obtained. The obtained correlation coefficients are recorded as $\{\xi_{corr}^{p_i}\}_{p_i=1}^{P_i}$.

1.4) A weight factor of the i-th sub-process is set as $f_i^{corr}$. A threshold $\theta_i^{corr}$ configured to select input features based on the correlation coefficients is calculated according to $$\theta_i^{corr} = f_i^{corr} \cdot \frac{1}{p_i} \sum_{p_i=1}^{P_i} (\xi_{corr}^{p_i})_i, \tag{6}$$

where a maximum value $(f_i^{corr})_{max}$ and a minimum value $(f_i^{corr})_{min}$ of $f_i^{corr}$ are calculated according to Equation (7):

$$\begin{cases} (f_i^{corr})_{max} = \dfrac{\max((\xi_{corr}^1)_i, \ldots, (\xi_{corr}^{p_i})_i, \ldots, (\xi_{corr}^{P_i})_i)}{\dfrac{1}{p_i} \sum_{p_i=1}^{P_i} (\xi_{corr}^{p_i})_i} \\[2ex] (f_i^{corr})_{min} = \dfrac{\min((\xi_{corr}^1)_i, \ldots, (\xi_{corr}^{p_i})_i, \ldots, (\xi_{corr}^{P_i})_i)}{\dfrac{1}{p_i} \sum_{p_i=1}^{P_i} (\xi_{corr}^{p_i})_i} \end{cases} \tag{7}$$

where max(•) is a function for finding a maximum value; and min(•) is a function for finding a minimum value.

1.5) The p-th input feature of the i-th sub-process is selected according to rules as follows:

$$\alpha_i^{p_i} = \begin{cases} 1, & \text{if } (\xi_{corr}^{p_i})_i \geq \theta_i^{corr} \\ 0, & \text{else } (\xi_{corr}^{p_i})_i < \theta_i^{corr} \end{cases} \tag{8}$$

where $\theta_i^{corr}$ is taken as a threshold.

1.6) A feature in $(x^{p_i})_i$ in $\alpha_t^{p_i} = 1$ is selected as a correlation coefficient-selected candidate feature. The correlation coefficient-selected candidate feature is recorded as $$\left(x^{(p_i)_{corr}^{sel}}\right)_i.$$

1.7) Steps (1.1)-(1.6) are performed for all of the original input features of the i-th sub-process. The selected candidate features are recorded as:

$$(X_{corr}^{sel})_i = \left[(x^1)_i, \ldots, (x^{(p_i)_{corr}^{sel}})_i, \ldots, (x^{(P_i)_{corr}^{sel}})_i\right] \tag{9}$$

where $(P_i)_{corr}^{sel}$ represents the number of correlation coefficient-selected process variables of the i-th sub-process; and $(X_{corr}^{sel})_i$ represents a correlation coefficient-selected candidate feature set from the input features of the i-th sub-process.

1.8) Steps (1.1)-(1.7) are repeated for all the sub-processes. Correlation coefficient measurement-selected features are recorded as $\{(X_{corr}^{sel})_i\}_{i=1}^{I}$.

Specifically, the step of obtaining the mutual information value includes the following steps.

2.1) A mutual information value between each of the original input features and the DXN emission concentration is calculated. For example, a mutual information value between the p-th input feature $(x^{p_i})_i$ of the i-th sub-process and the DXN emission concentration is calculated according to $$\left(\xi_{mi}^{p_i}\right)_i = \sum_{n=1}^{N}\sum_{n=1}^{N}\left\{p_{rob}\left(\left(x_n^{p_i}\right)_i, y_n\right)\log\left(\frac{p_{rob}\left(\left(x_n^{p_i}\right)_i, y_n\right)}{p_{rob}\left(\left(x_n^{p_i}\right)_i\right)p_{rob}(y_n)}\right)\right\} \quad (10)$$

where $p_{rob}((x_n^{p_i})_i, y_n)$ represents a joint probability density; and $p_{rob}((x_n^{p_i}))$ and $p_{rob}(y_n)$ each represent a marginal probability density.

2.2) Step (2.1) is repeated for all of the original input features until mutual information values of all of the original input features are obtained. The obtained mutual information values are recorded as $\{\xi_{mi}^{p_i}\}_{p_i=1}^{P_i}$.

2.3) A weight factor of the i-th sub-process is set as $f_i^{mi}$. A threshold $\theta_i^{mi}$ configured to select the input features based on the mutual information value is calculated according to $$\theta_i^{mi} = f_i^{mi} \cdot \frac{1}{p_i}\sum_{p_i=1}^{P_i}\left(\xi_{mi}^{p_i}\right)_i \quad (11)$$

where a maximum value $(f_i^{mi})_{max}$ and a minimum value $(f_i^{mi})_{min}$ of $f_i^{mi}$ are calculated according to Equation (12):

$$\begin{cases}\left(f_i^{mi}\right)_{max} = \dfrac{\max\left(\left(\xi_{mi}^{1}\right)_i, \ldots, \left(\xi_{mi}^{p_i}\right)_i, \ldots, \left(\xi_{mi}^{P_i}\right)_i\right)}{\dfrac{1}{p_i}\sum_{p_i=1}^{P_i}\left(\xi_{mi}^{p_i}\right)_i} \\ \left(f_i^{mi}\right)_{min} = \dfrac{\min\left(\left(\xi_{mi}^{1}\right)_i, \ldots, \left(\xi_{mi}^{p_i}\right)_i, \ldots, \left(\xi_{mi}^{P_i}\right)_i\right)}{\dfrac{1}{p_i}\sum_{p_i=1}^{P_i}\left(\xi_{mi}^{p_i}\right)_i}\end{cases} \quad (12)$$

wherein max(•) is a function for finding a maximum value; and min(•) is a function for finding a minimum value.

2.4) The p-th input feature of the i-th sub-process is selected according to rules as follows:

$$\beta_i^{p_i} = \begin{cases}1, & \text{if } \left(\xi_{mi}^{p_i}\right)_i \geq \theta_i^{mi} \\ 0, & \text{else } \left(\xi_{mi}^{p_i}\right)_i < \theta_i^{mi}\end{cases} \quad (13)$$

where $\theta_i^{mi}$ is taken as a threshold.

2.5) A feature $(x^{p_i})_i$ of $\beta_i^{p_i}=1$ is selected as a mutual information value-selected candidate feature. The mutual information value-selected candidate feature is recorded as $$\left(x^{(p_i)_{mi}^{sel}}\right)_i.$$

2.6) Steps (2.1)-(2.5) are performed for all of the input features of the i-th sub-process. The selected candidate features are recorded as:

$$\left(X_{mi}^{sel}\right)_i = \left[\left(x^1\right)_i, \ldots, \left(x^{(p_i)_{mi}^{sel}}\right)_i, \ldots, \left(x^{(P_i)_{mi}^{sel}}\right)_i\right] \quad (14)$$

where $(P_i)_{mi}^{sel}$ represents the number of mutual information value-selected features in the i-th sub-process; and $(X_{mi}^{sel})_i$ represents a candidate feature set selected based on a mutual information value measurement from the input features of the i-th sub-process.

2.7) Steps (2.1)-(2.6) are repeated for all the sub-processes. Mutual information value measurement-selected features are recorded as $\{(X_{mi}^{sel})_i\}_{i=1}^{I}$.

Specifically, the step of obtaining the comprehensive evaluation value is performed through the following steps.

3.1) For the i-th sub-process, the intersection of the mutual information-selected features $(X_{mi}^{sel})_i$ and the correlation coefficient-selected features $(X_{corr}^{sel})_i$ is performed according to Equation (15), thereby obtaining a comprehensive evaluation value-selected candidate feature set $$\left(X_{corr\_mi}^{sel}\right)_i = \left(X_{mi}^{sel}\right)_i \cap \left(X_{corr}^{sel}\right)_i = \left[\left(x^1\right)_i, \ldots, \left(x^{(p_i)_{corr\_mi}^{sel}}\right)_i, \ldots, \left(x^{(P_i)_{corr\_mi}^{sel}}\right)_i\right]. \quad (15)$$

where ∩ represents the intersection;

$$x_i^{(p_i)_{corr\_mi}^{sel}}$$

represents a $(p_i)_{corr\_mi}^{sel}$-th candidate feature of the i-th sub-process; and a correlation coefficient value of the $(p_i)_{corr\_mi}^{sel}$-th candidate feature is $$\left(\xi_{corr}^{(p_i)_{corr\_mi}^{sel}}\right)_i;$$

and a mutual information value of the $(p_i)_{corr\_mi}^{sel}$-th candidate feature is $$\left(\xi_{mi}^{(p_i)_{corr\_mi}^{sel}}\right)_i.$$

3.2) Normalization is performed according to Equations (16) and (17) so as to eliminate size differences of the correlation coefficient value and mutual information value of the different input features;

$$\left(\zeta_{corr\_norm}^{(p_i)_{corr\_mi}^{sel}}\right)_i = \frac{\left(\zeta_{corr}^{(p_i)_{corr\_mi}^{sel}}\right)_i}{\sum_{(p_i)_{corr\_mi}^{sel}=1}^{(P_i)_{corr\_mi}^{sel}}\left(\zeta_{corr}^{(p_i)_{corr\_mi}^{sel}}\right)_i} \quad (16)$$

$$\left(\zeta_{mi\_norm}^{(p_i)_{corr\_mi}^{sel}}\right)_i = \frac{\left(\zeta_{mi}^{(p_i)_{corr\_mi}^{sel}}\right)_i}{\sum_{(p_i)_{corr\_mi}^{sel}=1}^{(P_i)_{corr\_mi}^{sel}} \left(\zeta_{mi}^{(p_i)_{corr\_mi}^{sel}}\right)_i} \quad (17)$$

where $$\left(\zeta_{corr\_norm}^{(p_i)_{corr\_mi}^{sel}}\right)_i$$

represents a standardized correlation coefficient value of the $p_{corr\_mi}^{sel}$-th candidate feature of the i-th sub-process; and $$\left(\zeta_{mi\_norm}^{(p_i)_{corr\_mi}^{sel}}\right)_i$$

represents a standardized mutual information value of the $p_{corr\_mi}^{sel}$-th candidate feature of the i-th sub-process.

3.3) The comprehensive evaluation value of the candidate input features are defined as $$\zeta_i^{(p_i)_{corr\_mi}^{sel}},$$

and are expressed as follows:

$$\zeta_{corr\_mi}^{(p_i)_{corr\_mi}^{sel}} = k_i^{corr} \cdot \zeta_{corr\_norm}^{(p_i)_{corr\_mi}^{sel}} + k_i^{mi} \cdot \zeta_{mi\_norm}^{(p_i)_{corr\_mi}^{sel}} \quad (18)$$

where $k_i^{corr}$ and $k_i^{mi}$ each represent a proportional coefficient; and $k_i^{corr} + k_i^{mi} = 1$.

3.4) Steps (3.1)-(3.3) are repeated for the respective candidate input features until comprehensive evaluation values of all of the candidate input features are obtained. The obtained comprehensive evaluation values are recorded as $$\left\{\zeta_{corr\_mi}^{(p_i)_{corr\_mi}^{sel}}\right\}_{(p_i)_{corr\_mi}^{sel}=1}^{(P_i)_{corr\_mi}^{sel}}.$$

Specifically, $k_i^{corr}$ is equal to 0.5; and $k_i^{mi}$ is equal to 0.5.

Specifically, the step of obtaining the comprehensive evaluation value of the candidate input features according to the correlation coefficient value and the mutual information value is performed through the following steps.

4.1) A weight factor of the i-th sub-process is set as $f_i^{corr\_mi}$. A threshold $\theta_i^{1stsel}$ configured to select the input features based on the comprehensive evaluation value is calculated as follows:

$$\theta_i^{1stsel} = f_i^{corr\_mi} \cdot \frac{1}{(P_i)_{corr\_mi}^{sel}} \sum_{(p_i)_{corr\_mi}^{sel}=1}^{(P_i)_{corr\_mi}^{sel}} \left(\zeta_{corr\_mi}^{(p_i)_{corr\_mi}^{sel}}\right)_i \quad (19)$$

where a maximum value $(f_i^{corr\_mi})_{max}$ and a minimum value $(f_i^{corr\_mi})_{min}$ of $f_t^{corr\_mi}$ are calculated according to Equation (20):

$$\begin{cases} (f_i^{corr\_mi})_{max} = \dfrac{\max\left((\zeta_{corr\_mi}^1)_i, \ldots, (\zeta_{corr\_mi}^{(p_i)_{corr\_mi}^{sel}})_i, \ldots\right)}{\dfrac{1}{(P_i)_{corr\_mi}^{sel}} \sum_{(p_i)_{corr\_mi}^{sel}=1}^{(P_i)_{corr\_mi}^{sel}} \left(\zeta_{corr\_mi}^{(p_i)_{corr\_mi}^{sel}}\right)_i} \\ \\ (f_i^{corr\_mi})_{min} = \dfrac{\min\left((\zeta_{corr\_mi}^1)_i, \ldots, (\zeta_{corr\_mi}^{(p_i)_{corr\_mi}^{sel}})_i, \ldots\right)}{\dfrac{1}{(P_i)_{corr\_mi}^{sel}} \sum_{(p_i)_{corr\_mi}^{sel}=1}^{(P_i)_{corr\_mi}^{sel}} \left(\zeta_{corr\_mi}^{(p_i)_{corr\_mi}^{sel}}\right)_i} \end{cases} \quad (20)$$

4.2) A $(p_i)_{corr\_mi}^{sel}$-th candidate input feature of the i-th sub-process is selected according to rules as follows:

$$\gamma^{(p_i)_{corr\_mi}^{sel}} = \begin{cases} 1, & \text{if } \zeta_{corr\_mi}^{(p_i)_{corr\_mi}^{sel}} \geq \theta_i^{1stsel} \\ 0, & \text{else } \zeta_{corr\_mi}^{(p_i)_{corr\_mi}^{sel}} < \theta_i^{1stsel} \end{cases} \quad (21)$$

where $\theta_t^{1stsel}$ is taken as a threshold.

4.3) Steps (4.1)-(4.2) are performed for all the original candidate input features. Variables of $$\gamma^{(p_i)_{corr\_mi}^{sel}} = 1$$

are selected as comprehensive evaluation value-selected input features, and recorded as:

$$(X_{1st}^{sel})_i = \left[(x^1)_i, \ldots, (x^{p_i^{sel}})_i, \ldots, (x^{P_i^{sel}})_i\right] \quad (22)$$

where $(X_{1st}^{sel})_i$ represents first-level features of the i-th sub-process selected by a comprehensive evaluation value measurement from the candidate feature set selected by a correlation coefficient method and a mutual information method.

4.4) Steps (4.1)-(4.3) are repeated until the first-level features of all the sub-processes are obtained.

Specifically, the step of arranging the first-level features in series is performed through the following steps.

The first-level features are arranged in series to obtain the first-level features $X_{1st}^{sel}$ based on the single feature correlation;

$$X_{1st}^{sel} = \left[(X_{1st}^{sel})_1, \ldots, (X_{1st}^{sel})_i, \ldots, (X_{1st}^{sel})_I\right] = \left[x^{1sel}_{1st}, \ldots, x^{p_{sel}^{sel}}_{1st}, \ldots, x^{p_{sel}^{sel}}_{1st}\right] \quad (23)$$

where $$x^{p_{1st}^{sel}}$$

represents a $p_{1st}^{sel}$-th feature in a first-level feature selection set;

$$P_{1st}^{sel} \sum_{i=1}^{I} P_i^{sel}$$

represents the number of all of the first-level features; and $X_{1st}^{sel}$ represents single feature correlation-based first-level feature obtained by serially combining the first-level features of all of the sub-processes.

Specifically, a strategy of selecting the second-level features is described as follows.

The first-level features $X_{1st}^{sel}$ are inputted into a GAPLS algorithm. After running the GAPLS algorithm J times, the second-level features $(X_{2nd}^{sel})_j$ are outputted. Then the number of times that the respective inputted first-level features are selected is outputted. The second-level features that are selected $J_{sel}$ times are statistically processed. When a GAPLS model prediction error is smaller than a prediction error average obtained by running the GAPLS algorithm J times, a second-level feature is selected.

The number of times that a $p_{1st}^{sel}$-th feature is selected is recorded as $$f_{num}^{p_{1st}^{sel}};$$

accordingly, all $P_{1st}^{sel}$-th features of the first-level features are recorded as $$\left\{ f_{num}^{p_{jst}^{sel}} \right\}_{p_{1st}^{sel}=1}^{P_{1st}^{sel}}.$$

J is the number of times that the GAPLS algorithm runs. $J_{sel}$ is the number of GAPLS models prediction errors of which are smaller than a prediction error average. $(X_{2nd}^{sel})_j$ represents multiple feature redundancy-based second-level features selected by jth run of the GAPLS algorithm.

Specifically, the step of selecting the second-level features is performed through the following steps.

5.1) The number of times that the GAPLS algorithm runs is set as J. GAPLS algorithm parameters are set. Population size, maximum genetic algebra, mutation probability, a crossover method and a number of latent variables of the PLS algorithm are initialized. j=1 is set and the selection of the second-level features is started.

5.2) Whether the GAPLS algorithm runs J times is determined. If yes, step (5.11) continues; if no, step (5.3) continues.

5.3) Binary encoding for features is performed. A length of a chromosome is the number of input features. 1 implies that a feature is selected; and 0 implies that no feature is selected.

5.4) Random initialization on population is performed.

5.5) The fitness of the population is evaluated. A root mean square error of cross-validation (RMSECV) is calculated using a leave-one-out cross-validation method.

5.6) Whether a termination condition of the maximum genetic algebra is reached is determined. If no, step (5.7) continues. If yes, step (5.9) continues.

5.7) Genetic operations including selection, crossover and variation are performed. The selection is performed through an elite substitution strategy, that is, individuals with poor fitness are replaced with individuals with good fitness. The crossover is performed through single point crossover. The genetic variation is performed through single point mutation;

5.8) A new population is obtained and step (5.5) continues.

5.9) An optimal individual is obtained by running the GAPLS algorithm J times. Decoding is performed to obtain selected second-level features. The selected second-level features are recorded as $(X_{2nd}^{sel})_j$.

5.10) Let j=j+1, and step (5.2) continues.

5.11) An average value of root mean square errors (RMSE) of a prediction model is calculated by running the GAPLS algorithm J times. The number of the root mean square errors of the GAPLS model that are larger than the average value is recorded as $J_{sel}$. The second-level features that are selected $J_{sel}$ so times are processed by counting the number of times that the $P_{1st}^{sel}$-th feature in the first-level features is selected, $$\left\{ (X_{2nd}^{sel}) \right\}_{j=1}^{J} \Rightarrow \left\{ f_{num}^{1_{1st}^{sel}}, \ldots, f_{num}^{p_{1st}^{sel}}, \ldots, f_{num}^{P_{1st}^{sel}} \right\} = \left\{ f_{num}^{p_{jst}^{sel}} \right\}_{p_{1st}^{sel}=1}^{P_{1st}^{sel}}, \quad (24)$$

$$1 \leq f_{num}^{p_{1st}^{sel}} \leq J_{sel}$$

where $$f_{num}^{p_{1st}^{sel}}$$

is the number of times that the $p_{1st}^{sel}$-th feature in the first-level features is selected.

Specifically, the population size is 20. The maximum genetic algebra is 40. A maximum number of latent variables of the PLS algorithm is 6. The mutation probability is 0.005.

Specifically, the step of selecting the third-level features is performed through the following steps.

According to the number of times $$\left\{ f_{num}^{p_{1st}^{sel}} \right\}_{p_{1st}^{sel}=1}^{P_{1st}^{sel}}$$

that all the $p_{1st}^{sel}$-th features in the first-level features are selected, a scale factor is set as $f_{DXN}^{RMSE}$. A lower limit of a threshold configured to select the third-level features recorded as $\theta_{DXN}^{downlimit}$ and calculated according to:

$$\theta_{DXN}^{downlimit} = \text{floor}\left( f_{DXN}^{RMSE} \cdot \frac{1}{P_{1st}^{sel}} \sum_{p_{1st}^{sel}=1}^{P_{1st}^{sel}} f_{num}^{p_{1st}^{sel}} \right) \quad (25)$$

where floor(•) indicates a function that returns integers. A maximum value $(f_{DXN}^{RMSE})_{max}$ and a minimum value $(f_{DXN}^{RMSE})_{min}$ of $f_{DXN}^{RMSE}$ are calculated according to $$\begin{cases} (f_{DXN}^{RMSE})_{max} = \dfrac{\max\left(f_{num}^{1_{st}^{sel}}, \ldots, f_{num}^{p_{1st}^{sel}}, \ldots, f_{num}^{P_{1st}^{sel}}\right)}{\dfrac{1}{P_{1st}^{sel}} \sum\limits_{p_{1st}^{sel}=1}^{P_{1st}^{sel}} f_{num}^{p_{1st}^{sel}}} \\ (f_{DXN}^{RMSE})_{min} = \dfrac{\min\left(f_{num}^{1_{st}^{sel}}, \ldots, f_{num}^{p_{1st}^{sel}}, \ldots, f_{num}^{P_{1st}^{sel}}\right)}{\dfrac{1}{P_{1st}^{sel}} \sum\limits_{p_{1st}^{sel}=1}^{P_{1st}^{sel}} f_{num}^{p_{1st}^{sel}}} \end{cases} \quad (26)$$

A maximum value of the number of times that all the $p_{1st}^{sel}$-th features in the first-level features are selected is found based on an upper limit $\theta_{DXN}^{uplimit}$ of the threshold configured to select the third-level features, $$\theta_{DXN}^{uplimit} = \max\left(f_{num}^{1_{st}^{sel}}, \ldots, f_{num}^{p_{1st}^{sel}}, \ldots, f_{num}^{P_{1st}^{sel}}\right) \quad (27)$$

The threshold is recorded as $\theta_{DXN}^{3rd}$ and is between $\theta_{DXN}^{downlimit}$ and $\theta_{DXN}^{uplimit}$. The third-level features are obtained according to $$\mu^p = \begin{cases} 1, & \text{if } f_{num}^{p_{1st}^{sel}} \geq \theta_{DXN}^{3rd} \\ 0, & \text{else } f_{num}^{p_{1st}^{sel}} < \theta_{DXN}^{3rd} \end{cases}, \quad (28)$$

where $$f_{num}^{p_{1st}^{sel}}$$

represents the number of times that the $p_{1st}^{sel}$-th feature in the first-level features is selected by running the GAPLS algorithm J times; $\mu^p$ represents a threshold selection criterion for selecting the third-level features.

Feature variables of $\mu^p = 1$ are sequentially stored in $X_{3rd}^{sel\_temp}$. The RMSE is calculated. $X_{3rd}^{sel\_temp}$ serves as input variables in the establishment of the PLS algorithm-based DXN detection model. $X_{3rd}^{sel}$ represents the third-level features selected from $X_{1st}^{sel}$ based on a feature selection threshold $\theta_{3rd}$ and prior knowledge.

Specifically, the step of establishing the DXN detection model based on the PLS algorithm is implemented through the following steps.

Values of the threshold $\theta_{DXN}^{3rd}$ between $\theta_{DXN}^{downlimit}$ and $\theta_{DXN}^{uplimit}$ are increased one by one so as to establish a plurality of first temporary PLS algorithm-based DXN detection model.

A second temporary PLS algorithm-based DXN detection model is selected from the plurality of first temporary PLS algorithm-based DXN detection models. The second temporary PLS algorithm-based DXN detection model has a minimum value of RMSE.

Checking the input features of the DXN emission concentration detection model is performed to determine whether the input features comprises concentrations of CO, HCL, $O_2$ and $NO_x$ emitted from a chimney. At the same time, features in the common resource supply Rib-process are removed. If the input features do not include concentrations of CO, HCL, $O_2$ and $NO_x$, the third-level features are additionally selected to obtain selected three-level features $X_{3rd}^{sel}$, thereby varying the number of features that are selected and establishing the PLS algorithm-based DXN detection model based on prior knowledge.

Specifically, variables of the PLS algorithm-based DXN detection model have 287 dimensions.

Specifically, weight factors $f_i^{corr}$, $f_i^{mi}$ and $f_i^{corr\_mi}$ of feature selection of the correlation coefficient value and the mutual information value of the first-level features are 0.8.

Specifically, there are 132 feature variables selected by the comprehensive evaluation value. For the selected 132 process variables based on the single feature correlation, an optimal combination of the process variables is determined using the GAPLS algorithm so as to remove redundant features.

The present embodiment provides a method for detecting a dioxin (DXN) emission concentration in a MSWI process based on multi-level feature selection, which is implemented through the following specific steps.

Figure 3:
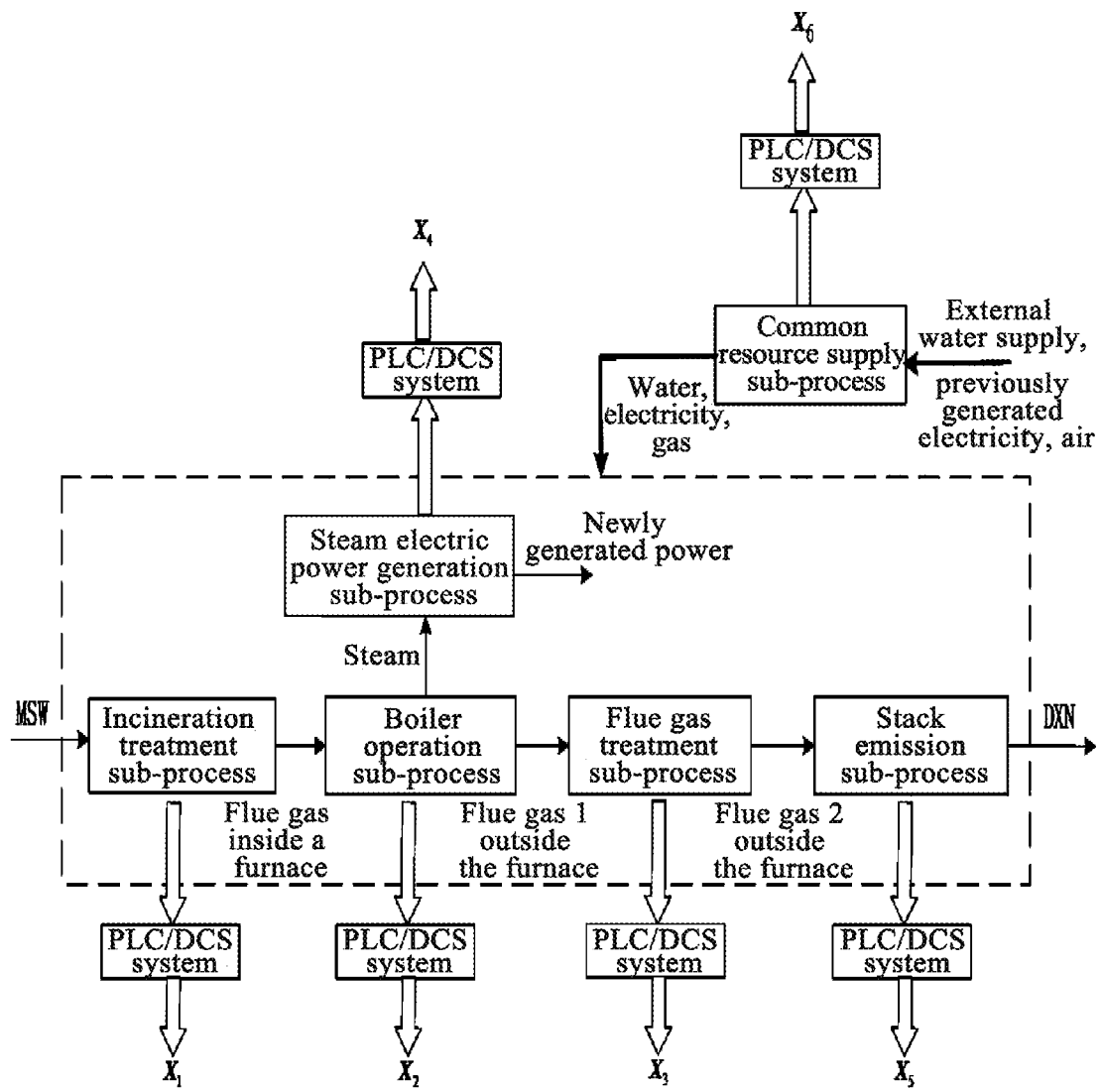
FIG. 3 schematically shows a strategy for detecting the DXN emission concentration according to an embodiment of the present application.

A municipal solid waste incineration (MSWI) process is divided into six sub-processes based on an incineration process. The six sub-processes include an incineration treatment sub-process, a boiler operation sub-process, a flue gas treatment sub-process, a steam electric power generation sub-process, a stack emission sub-process and a common resource supply sub-process. FIG. 3 schematically shows a DXN emission concentration detection strategy according to an embodiment of the present application.

In the present application, the input data of the DXN detection model is expressed as $X \in R^{N \times P}$ and includes N samples as row data and P variables as column data. The input data is derived from respective sub-processes of the MSWI process. Monitoring data of an i-th sub-process is obtained by using a programmable logic controller (PLC) device or a distributed control system (DCS) device installed on site and is expressed as $X_i \in R^{N \times P_i}$, which is input data from the i-th Rib-process and satisfies Equations (1) and (2);

$$X = [X_1, \ldots, X_i, \ldots, X_I] = \{X_i\}_{i=1}^I \quad (1)$$

$$P = P_1 + \ldots + P_i + \ldots + P_I = \Sigma_{i=1}^I P_i \quad (2).$$

I represents the number of the sub-processes. $P_i$ represents the number of input features in the i-th sub-process, and the input features are variables derived from the monitoring data.

Accordingly, output data of the DXN detection model is expressed as $y = \{y_n\}_{n=1}^N \in R^{N \times 1}$ and includes N samples as row data.

Obviously, the input/output data of the model is quite different in a time scale, and thus $N << P$.

In order to make the following description understandable, $X_i$ is modified as:

$$\begin{aligned} X_i &= \left[ \{(x_n^1)_i\}_{n=1}^N, \ldots, \{(x_n^{p_i})_i\}_{n=1}^N, \ldots, \{(x_n^{P_i})_i\}_{n=1}^N \right] \\ &= [(x^1)_i, \ldots, (x^{p_i})_i, \ldots, (x^{P_i})_i] \\ &= \{(x^{p_i})_i\}_{p_i=1}^{P_i}, \end{aligned} \quad (3)$$

where $(x^{p_i})_i$ represents the $p_i$-th input feature of the i-th sub-process, and $x^{p_i} = \{x_n^{p_i}\}_{n=1}^N$ represents a column vector.

Figure 4:
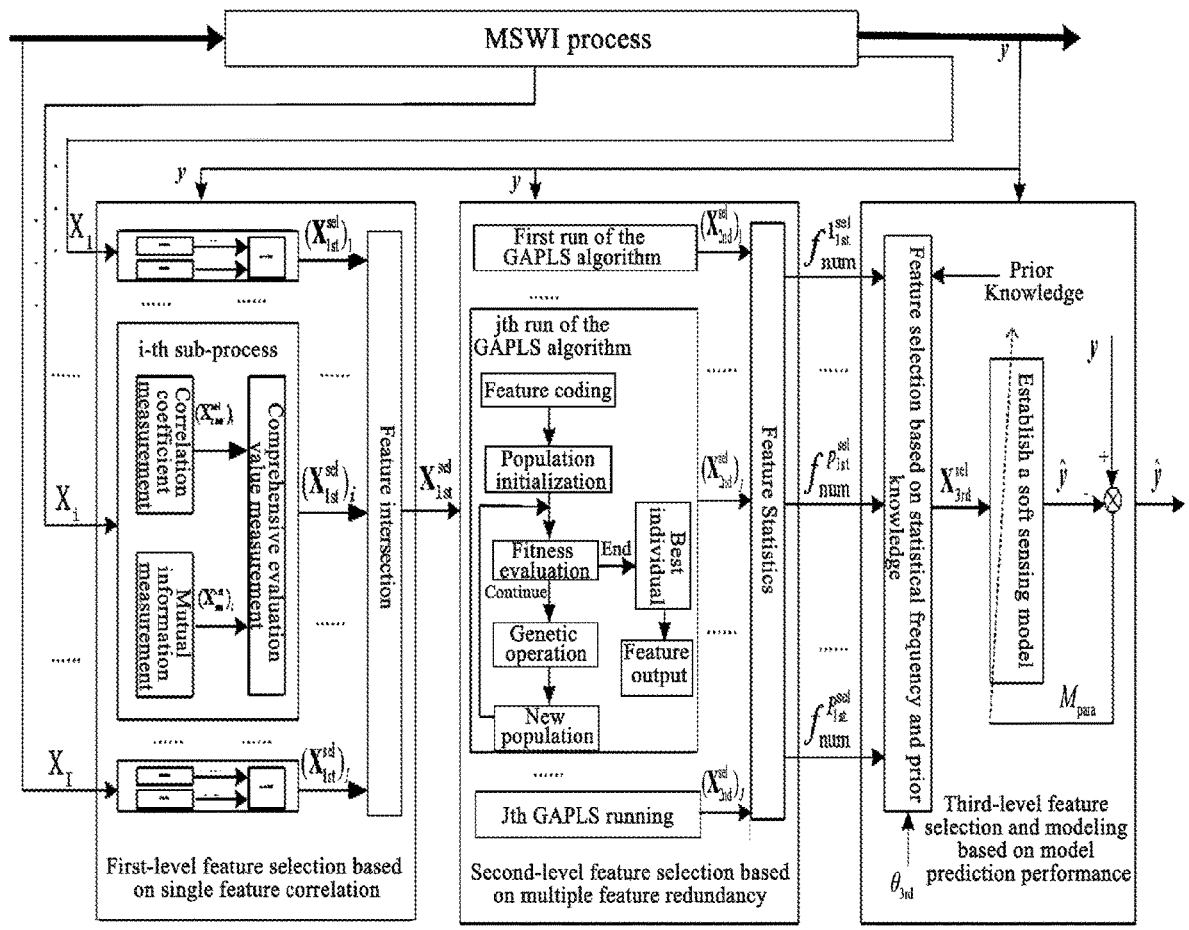
FIG. 4 shows a relationship between sub-processes of MSWI as well as detection data acquisition according to an embodiment of the present application.

The present application provides a DXN emission concentration detection strategy for a MSWI process based on multi-level feature selection. FIG. 4 shows a relationship between the sub-processes of MSWI as well as detection data acquisition according to an embodiment of the present application.

As shown in FIG. 4, $(X_{corr}^{sel})_i$ represents a correlation coefficient-selected candidate feature set selected from the input features of the i-th sub-process. $(X_{mi}^{sel})_t$ represents a mutual information measurement-selected candidate feature set for the input features of the i-th sub-process. $(X_{1st}^{sel})_t$ represents a candidate feature set selected based on a mutual information value measurement from the selected first-level features of the i-th sub-process. $X_{1st}^{sel}$ represents the single feature correlation-based first-level features obtained by serially combining the first-level features of all the sub-processes. $(X_{2nd}^{sel})_j$ represents the multi-feature redundancy-based second-level features selected by running the GAPLS algorithm J times.

$$f_{num}^{p_{1st}^{sel}}$$

represents the number of times that the $p_{1st}^{sel}$-th feature in the first-level features is selected. $X_{3rd}^{sel}$ represents a third-level feature selected from $X_{1st}^{sel}$ in the light of a feature selection threshold $\theta_{3rd}$ and prior knowledge. $M_{parx}$ represents parameters of the detection model. $\hat{y}$ represents a predicted value.

In the method of the present embodiment, the algorithm is realized through the following steps.

1. First-Level Feature Selection Based on Single Feature Correlation 1.1 Single Feature Correlation Measurement Based on Correlation Coefficient Step 1.1) An original correlation coefficient value between each of the original input features and the DXN emission concentration is calculated. For example, an original correlation coefficient value between a p-th input feature $(x^{p_i})_i = \{(x_n^{p_i})_i\}_{n=1}^N$ of the i-th sub-process and the DXN emission concentration is calculated according to $$\left(\xi_{corr\_ori}^{p_i}\right)_i = \frac{\sum_{n=1}^{N}\left[\left((x_n^{p_i})_i - \bar{x}_{p_i}\right)(y_n - \bar{y})\right]}{\sqrt{\sum_{n=1}^{N}\left((x_n^{p_i})_i - \bar{x}_{p_i}\right)^2}\sqrt{\sum_{n=1}^{N}(y_n - \bar{y})^2}} \quad (4)$$

where $\bar{x}_{p_i}$ represents an average value of the p-th input feature of the i-th sub-process; and $\bar{y}$ represents an average value of N modeling samples of the DXN emission concentration.

Step 1.2) The original correlation coefficient value $(\xi_{corr\_ori}^{p_i})_i$ is preprocessed as follows:

$$(\xi_{corr}^{p_i})_i = |(\xi_{corr\_ori}^{p_i})_i| \quad (5)$$

where $|\cdot|$ represents an absolute value.

Step 1.3) Steps (1.1)-(1.2) are repeated for respective original input features until correlation coefficients for all of the original input features are obtained and recorded as $\{\xi_{corr}^{p_i}\}_{p_i=1}^{P_i}$.

Step 1.4) A weight factor of the i-th sub-process is set as $f_i^{corr}$. A threshold $\theta_i^{corr}$ configured to select input features based on the correlation coefficients is calculated according to:

$$\theta_i^{corr} = f_i^{corr} \cdot \frac{1}{p_i}\sum_{p_i=1}^{p_i}\left(\xi_{corr}^{p_i}\right)_i, \quad (6)$$

where a maximum value $(f_i^{corr})_{max}$ and a minimum value $(f_i^{corr})_{min}$ of $f_i^{corr}$ are calculated according to Equation (7):

$$\begin{cases} (f_i^{corr})_{max} = \dfrac{\max\left(\left(\xi_{corr}^1\right)_i, \ldots, \left(\xi_{corr}^{p_i}\right)_i, \ldots, \left(\xi_{corr}^{P_i}\right)_i\right)}{\dfrac{1}{p_i}\sum_{p_i=1}^{P_i}\left(\xi_{corr}^{p_i}\right)_i} \\ (f_i^{corr})_{min} = \dfrac{\min\left(\left(\xi_{corr}^1\right)_i, \ldots, \left(\xi_{corr}^{p_i}\right)_i, \ldots, \left(\xi_{corr}^{P_i}\right)_i\right)}{\dfrac{1}{p_i}\sum_{p_i=1}^{P_i}\left(\xi_{corr}^{p_i}\right)_i} \end{cases}, \quad (7)$$

where $\max(\bullet)$ represents a function for finding a maximum value; and $\min(\bullet)$ represents a function for finding a minimum value.

Step 1.5) The p-th input feature of the i-th sub-process is selected according to rules as follows:

$$\alpha_i^{p_i} = \begin{cases} 1, & \text{if } \left(\xi_{corr}^{p_i}\right)_i \geq \theta_i^{corr} \\ 0, & \text{else } \left(\xi_{corr}^{p_i}\right)_i < \theta_i^{corr} \end{cases} \quad (8)$$

where $\theta_i^{corr}$ is taken as a threshold.

Step 1.6) A feature $(x^{p_i})_i$ in $\alpha_i^{p_i}=1$ is selected as a correlation coefficient-selected candidate feature. The correlation coefficient-related candidate feature is recorded as $$\left(x^{(p_i)_{corr}^{sel}}\right)_i.$$

Step 1.7) Steps (1.1)-(1.6) are performed for all of the original input features of the i-th sub-process; and the selected candidate features are recorded as:

$$\left(X_{corr}^{sel}\right)_i = \left[(x^1)_i, \ldots, \left(x^{(p_i)_{corr}^{sel}}\right)_i, \ldots, \left(x^{(P_i)_{corr}^{sel}}\right)_i\right], \quad (9)$$

wherein $(P_i)_{corr}^{sel}$ represents the number of correlation coefficient-selected process variables of the i-th sub-process.

Step 1.8) Steps (1.1)-(1.7) are repeated for all the sub-processes; and correlation coefficient measurement-selected features are recorded as $\{(X_{corr}^{sel})_i\}_{t=1}^J$.

1.2 Single Feature Correlation Measurement Based on Mutual Information

Step 2.1) A mutual information value between each of the original input features and the DXN emission concentration is calculated. For example, a mutual information value between the p-th input feature $(x^{p_i})_i$ of the i-th sub-process and the DXN emission concentration is calculated according to $$\left(\xi_{mi}^{p_i}\right)_i = \sum_{n=1}^{N}\sum_{n=1}^{N}\left\{p_{rob}\left(\left(x_n^{p_i}\right)_i, y_n\right)\log\left(\frac{p_{rob}\left(\left(x_n^{p_i}\right)_i, y_n\right)}{p_{rob}\left(\left(x_n^{p_i}\right)_i\right)p_{rob}(y_n)}\right)\right\} \quad (10)$$

where $p_{rob}((x_n^{p_i})_i, y_n)$ represents a joint probability density; and $p_{rob}(((x_n^{p_i})_i)$ and $p_{rob}(y_n)$ each represent a marginal probability density.

Step 2.2) Step (2.1) is repeated for the respective original input features until mutual information values of all of the original input features are obtained. The obtained mutual information values are recorded as $\{\xi_{mi}^{p_i}\}_{p_i=1}^{P_i}$.

Step 2.3) A weight factor of the i-th sub-process is set as $f_i^{mi}$. A mutual information-related threshold $\theta_i^{mi}$ is calculated according to:

$$\theta_i^{mi} = f_i^{mi} \cdot \frac{1}{p_i}\sum_{p_i=1}^{P_i}\left(\xi_{mi}^{p_i}\right)_i \quad (11)$$

where a maximum value $(f_i^{mi})_{max}$ and a minimum value $(f_i^{mi})_{min}$ of $f_i^{mi}$ are calculated according to:

$$\begin{cases} \left(f_i^{mi}\right)_{max} = \dfrac{\max\left(\left(\xi_{mi}^{1}\right)_i, \ldots, \left(\xi_{mi}^{p_i}\right)_i, \ldots, \left(\xi_{mi}^{P_i}\right)_i\right)}{\dfrac{1}{p_i}\sum_{p_i=1}^{P_i}\left(\xi_{corr}^{p_i}\right)_i} \\ \left(f_i^{mi}\right)_{min} = \dfrac{\min\left(\left(\xi_{mi}^{1}\right)_i, \ldots, \left(\xi_{mi}^{p_i}\right)_i, \ldots, \left(\xi_{mi}^{P_i}\right)_i\right)}{\dfrac{1}{p_i}\sum_{p_i=1}^{P_i}\left(\xi_{mi}^{p_i}\right)_i} \end{cases} \quad (12)$$

Step 2.4) The p-th input feature of the i-th sub-process is selected according to rules as follows:

$$\beta_i^{p_i} = \begin{cases} 1, & \text{if } \left(\xi_{mi}^{p_i}\right)_i \geq \theta_i^{mi} \\ 0, & \text{else } \left(\xi_{mi}^{p_i}\right)_i < \theta_i^{mi} \end{cases}, \quad (13)$$

where $\theta_i^{mi}$ is taken as a threshold.

Step 2.5) A feature $(x^{p_i})_i$ of $\beta_i^{p_i}=1$ is selected as a mutual information-selected candidate feature. The mutual information-selected candidate feature is recorded as $$\left(x^{(p_i)_{mi}^{sel}}\right)_i.$$

Step 2.6) Steps (2.1)-(2.5) are repeated for all of the input features of the i-th sub-process. The selected candidate features are recorded as:

$$\left(X_{mi}^{sel}\right)_i = \left[\left(x^1\right)_i, \ldots, \left(x^{(p_i)_{mi}^{sel}}\right)_i, \ldots, \left(x^{(P_i)_{mi}^{sel}}\right)_i\right] \quad (14)$$

where $(P_i)_{mi}^{sel}$ represents the number of mutual information-selected features of the i-th sub-process.

Step 2.7) Steps (2.1)-(2.6) are repeated for all the sub-processes. Mutual information measurement-selected features are recorded as $\{(X_{mi}^{sel})_i\}_{i=1}^{I}$.

1.3 Single Feature Correlation Measurement Based on a Comprehensive Evaluation Value Step 3.1) For the i-th sub-process, the intersection of the mutual information-selected features $(X_{mi}^{sel})_i$ and the correlation coefficient-selected features $(X_{corr}^{sel})_i$ is performed according to Equation (15), thereby obtaining a comprehensive evaluation value-selected candidate feature set $$\left(X_{corr\_mi}^{sel}\right)_i = \quad (15)$$

$$\left(X_{mi}^{sel}\right)_i \cap \left(X_{corr}^{sel}\right)_i = \left[\left(x^1\right)_i, \ldots, \left(x^{(p_i)_{corr\_mi}^{sel}}\right)_i, \ldots, \left(x^{(P_i)_{corr\_mi}^{sel}}\right)_i\right],$$

where $\cap$ represents the intersection;

$$x^{(p_i)_{corr\_mi}^{sel}}$$

represents a $(p_i)_{corr\_mi}^{sel}$-th candidate feature of the i-th sub-process; and a correlation coefficient value of the $(p_i)_{corr\_mi}^{sel}$-th candidate feature is $$\left(\xi_{corr}^{(p_i)_{corr\_mi}^{sel}}\right)_i;$$

and a mutual information value of the $(p_i)_{corr\_mi}^{sel}$-th candidate feature is $$\left(\xi_{mi}^{(p_i)_{corr\_mi}^{sel}}\right)_i.$$

Step 3.2) Normalization is performed according to Equations (16) and (17) so as to eliminate size differences of the correlation coefficient value and mutual information value of the different input features;

$$\left(\zeta_{corr\_norm}^{(p_i)_{corr\_mi}^{sel}}\right)_i = \frac{\left(\zeta_{corr}^{(p_i)_{corr\_mi}^{sel}}\right)_i}{\sum_{(p_i)_{corr\_mi}^{sel}=1}^{(P_i)_{corr\_mi}^{sel}}\left(\zeta_{corr}^{(p_i)_{corr\_mi}^{sel}}\right)_i} \quad (16)$$

$$\left(\zeta_{mi\_norm}^{(p_i)_{corr\_mi}^{sel}}\right)_i = \frac{\left(\zeta_{mi}^{(p_i)_{corr\_mi}^{sel}}\right)_i}{\sum_{(p_i)_{corr\_mi}^{sel}=1}^{(P_i)_{corr\_mi}^{sel}}\left(\zeta_{mi}^{(p_i)_{corr\_mi}^{sel}}\right)_i} \quad (17)$$

where $$\left(\zeta_{corr\_norm}^{sel}\right)_i$$

represents a standardized correlation coefficient value of the $p_{corr\_mi}^{sel}$-th candidate feature of the i-th sub-process; and $$\left(\zeta_{mi\_norm}^{p_{corr\_mi}^{sel}}\right)_i$$

represents a standardized mutual information value of the $p_{corr\_mi}^{sel}$-th candidate feature of the i-th sub-process.

$$\zeta_i^{(p_i)_{corr\_mi}^{sel}}$$

Step 3.3) A comprehensive evaluation value of the candidate input features is defined as $$\zeta_i^{(P_i)_{corr\_mi}^{sel}}$$

and can be expressed as $$\zeta_{corr\_mi}^{(p_i)_{corr\_mi}^{sel}} = k_i^{corr} \cdot \zeta_{corr\_norm}^{(p_i)_{corr\_mi}^{sel}} + k_i^{mi} \cdot \zeta_{mi\_norm}^{(p_i)_{corr\_mi}^{sel}} \quad (18)$$

where $k_i^{corr}$ and $k_i^{mi}$ each represent a proportional coefficient having a default value of 0.5, and $k_i^{corr} + k_i^{mi} = 1$.

Step 3.4) Steps (3.1)-(3.3) are repeated until comprehensive evaluation values of all of the candidate input features are obtained and recorded as $$\left\{\zeta_{corr\_norm}^{(p_i)_{corr\_mi}^{sel}}\right\}_{(p_i)_{corr\_mi}^{sel}=1}^{(P_i)_{corr\_mi}^{sel}}.$$

Step 3.5) A weight factor of the i-th sub-process is set as $f_i^{corr\_mi}$. A comprehensive evaluation value-related threshold $\theta_i^{1stsel}$ is calculated according to $$\theta_i^{1stsel} = f_i^{corr\_mi} \cdot \frac{1}{(P_i)_{corr\_mi}^{sel}} \sum_{(p_i)_{corr\_mi}^{sel}=1}^{(P_i)_{corr\_mi}^{sel}} \left(\zeta_{corr\_mi}^{(p_i)_{corr\_mi}^{sel}}\right)_i \quad (19)$$

where a maximum value $(f_i^{corr\_mi})_{max}$ and a minimum value $(f_i^{corr\_mi})_{min}$ of $f_i^{corr\_mi}$ are calculated according to $$\begin{cases} (f_i^{corr\_mi})_{max} = \dfrac{\max\left((\zeta_{corr\_mi}^1)_i, \ldots, \left(\zeta_{corr\_mi}^{(p_i)_{corr\_mi}^{sel}}\right)_i, \ldots, \left(\zeta_{corr\_mi}^{(P_i)_{corr\_mi}^{sel}}\right)_i\right)}{\dfrac{1}{(P_i)_{corr\_mi}^{sel}} \sum\limits_{(p_i)_{corr\_mi}^{sel}=1}^{(P_i)_{corr\_mi}^{sel}} \left(\zeta_{corr\_mi}^{(p_i)_{corr\_mi}^{sel}}\right)_i} \\[2ex] (f_i^{corr\_mi})_{min} = \dfrac{\min\left((\zeta_{corr\_mi}^1)_i, \ldots, \left(\zeta_{corr\_mi}^{(p_i)_{corr\_mi}^{sel}}\right)_i, \ldots, \left(\zeta_{corr\_mi}^{(P_i)_{corr\_mi}^{sel}}\right)_i\right)}{\dfrac{1}{(P_i)_{corr\_mi}^{sel}} \sum\limits_{(p_i)_{corr\_mi}^{sel}=1}^{(P_i)_{corr\_mi}^{sel}} \left(\zeta_{corr\_mi}^{(p_i)_{corr\_mi}^{sel}}\right)_i} \end{cases} \quad (20)$$

Step 3.6) A $(p_i)_{corr\_mi}^{sel}$-th candidate input feature of the i-th sub-process is selected according to rules as follows:

$$\gamma^{(p_i)_{corr\_mi}^{sel}} = \begin{cases} 1, & \text{if } \zeta_{corr\_mi}^{(p_i)_{corr\_mi}^{sel}} \geq \theta_i^{1stsel} \\ 0, & \text{else } \zeta_{corr\_mi}^{(p_i)_{corr\_mi}^{sel}} < \theta_i^{1stsel} \end{cases} \quad (21)$$

where $\theta_t^{1stsel}$ is taken as a threshold.

Step 3.7) Steps (3.5)(3.6) are performed for all the original candidate input features. Variables of $$\gamma^{(p_i)_{corr\_mi}^{sel}} = 1$$

are selected as comprehensive evaluation value-related input feature and expressed as:

$$(X_{1st}^{sel})_i = [(x^1)_i, \ldots, (x^{p_i^{sel}})_i, \ldots, (x^{p_i^{sel}})_i] \quad (22).$$

Step 3.8) Steps (3.5)-(3.7) are repeated until the selection of the first-level features of all the sub-processes is completed.

Step 3.9) The first-level features are arranged in series to obtain the first-level features $X_{1st}^{sel}$ based on the single feature correlation;

$$X_{1st}^{sel} = [(X_{1st}^{sel})_1, \ldots, (X_{1st}^{sel})_i, \ldots, (X_{1st}^{sel})_I] = [x^{1sel}_{1st}, \ldots, x^{p_{1st}^{sel}}, \ldots, x^{p_{1st}^{sel}}] \quad (23)$$

where $$x^{p_{1st}^{sel}}$$

represents a $p_{1st}^{sel}$-th feature in a first-level feature selection set; and $$P_{1st}^{sel} = \sum_{i=1}^{I} P_i^{sel}$$

represents the number of all of the first-level features.

2. Second-Level Feature Selection Based on Multiple Feature Redundancy

In the first-level feature selection, only the correlation between a single input feature and the DXN emission concentration is considered, and the redundancy between multiple features is not considered. For the second-level feature selection, GAPLS-based feature selection algorithm is used and the redundancy between multiple features is considered. In the consideration that DXN emission concentration modeling has small sample size and the genetic algorithm (GA) has randomness, provided herein is a second-level feature selection strategy based on multiple feature redundancy according an embodiment of the present application, as shown in FIG. 5.

Figure 5:
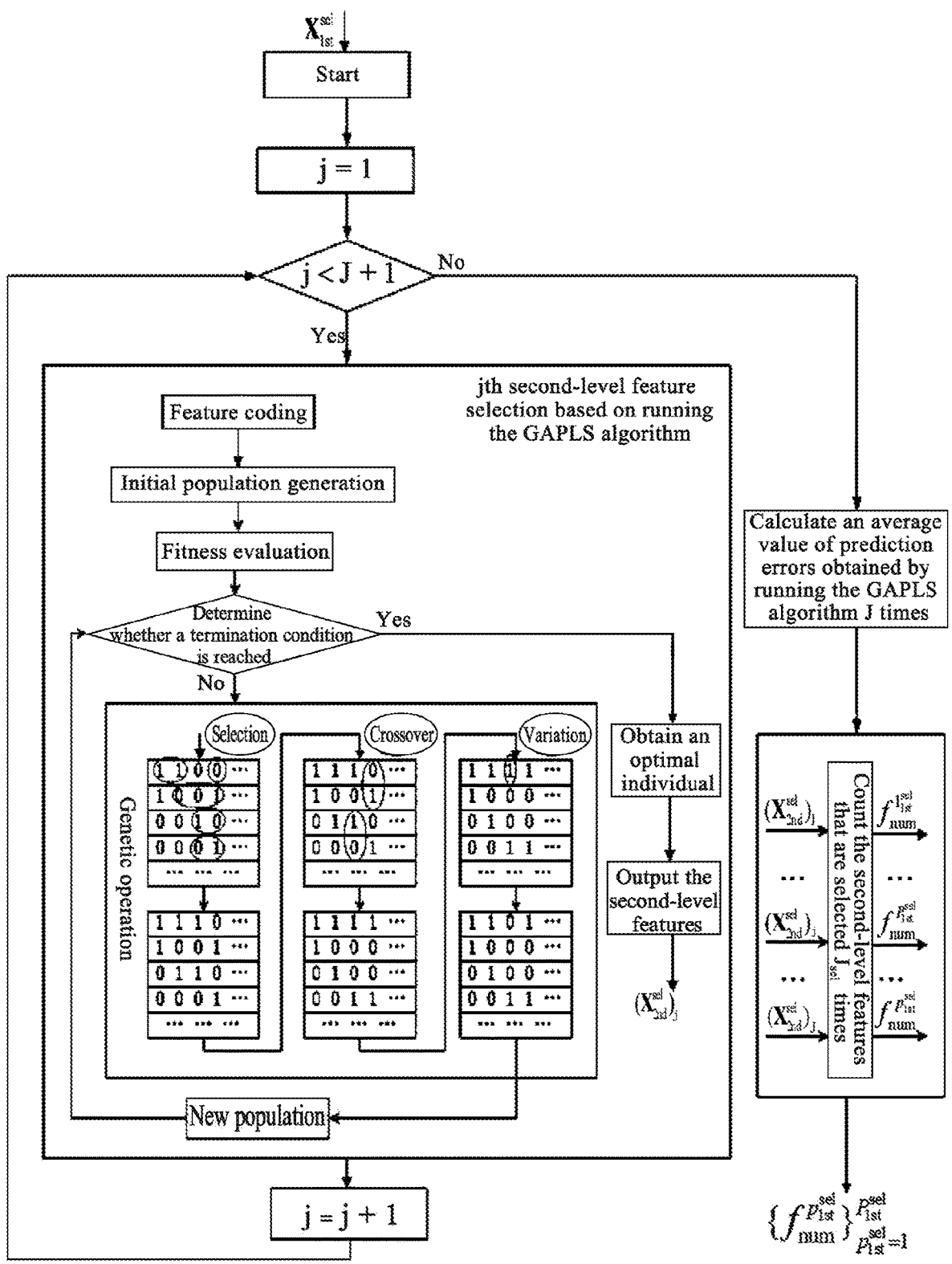
FIG. 5 is a schematic diagram of a second-level feature selection strategy based on multi-feature redundancy according to an embodiment of the present application.

It can be seen from FIG. 5, the first-level features $X_{1st}^{sel}$ are inputted. After running the GAPLS algorithm J times, the second-level features $(X_{2nd}^{sel})_j$ are outputted. Then the number of times that the respective first-level input features are selected is outputted. The second-level features that are selected $J_{sel}$ times are statistically processed. The number of times that a $p_{1st}^{sel}$-th feature is selected is recorded as $$f_{num}^{p_{1st}^{sel}},$$

and accordingly, all $P_{1st}^{sel}$-th features of the first-level features are recorded as $$\left\{ f_{num}^{p_{1st}^{sel}} \right\}_{p_{1st}^{sel}=1}^{P_{1st}^{sel}}.$$

J is the number of times that the GAPLS algorithm runs, and the GAPLS algorithm generally runs more than 100 times. $J_{sel}$ is the number of GAPLS model J prediction errors smaller than a prediction error average obtained by running the GAPLS algorithm J times.

The second-level feature selection is performed through the following steps.

Step 1) The number of times that the GAPLS algorithm runs is set as J. GAPLS algorithm parameters are set. A population size, maximum genetic algebra, mutation probability, a crossover method and a number of latent variables of the PLS algorithm are initialized and generally set to 6. Let j=1 and the selection of the second-level features is started.

Step 2) Whether the GAPLS algorithm runs J times is determined. If yes, step (11) continues. If no, step (3) continues.

Step 3) Binary encoding for features is performed, where a length of a chromosome is the number of input features. 1 implies that a feature is selected. 0 implies that no feature is selected.

Step 4) Random initialization is performed on population.

Step 5) The fitness of the population is evaluated. A root mean square error of cross-validation (RMSECV) is calculated using a leave-one-out cross-validation method. The smaller the RMSECV, the better the fitness.

Step 6) Whether a termination condition of the maximum genetic algebra is reached is determined. If no, step (7) continues. If yes, step (9) continues.

Step 7) Genetic operations including selection, crossover and variation are performed through an elite substitution strategy, that is, individuals with poor fitness are replaced with individuals with good fitness. The crossover is performed through single point crossover. The genetic variation is performed through single point mutation.

Step 8) A new population is obtained and step (5) continues.

Step 9) An optimal individual is obtained by running the GAPLS algorithm J times. Further, decoding is performed to obtain selected second-level features $(X_{2nd}^{sel})_j$.

Step 10) Let j=j+1, and step (2) continues.

Step 11) An average value of root mean square errors (RMSE) of a prediction model is calculated by running the GAPLS algorithm J times. The number of the root mean square errors of the GAPLS model that are larger than the average value is recorded as $J_{sel}$. The second-level features that are selected $J_{sel}$ times is processed by counting the number of times that the $P_{1st}^{sel}$-th feature in the first-level features is selected $$\left\{ (X_{2nd}^{sel})_j \right\}_{j=1}^{J_{sel}} \Rightarrow \left\{ f_{num}^{1_{1st}^{sel}}, \ldots, f_{num}^{p_{1st}^{sel}}, \ldots, f_{num}^{P_{1st}^{sel}} \right\} = \left\{ f_{num}^{p_{1st}^{sel}} \right\}_{p_{1st}^{sel}=1}^{P_{1st}^{sel}}, \quad (24)$$

$$1 \leq f_{num}^{p_{1st}^{sel}} \leq J_{sel},$$

where $$f_{num}^{p_{1st}^{sel}}$$

is the number of times that the $p_{1st}^{sel}$-th feature in the first-level features is selected.

3. Third-level feature selection and modeling based on model prediction performance According to the number of times $$\left\{ f_{num}^{p_{1st}^{sel}} \right\}_{p_{1st}^{sel}=1}^{P_{1st}^{sel}}$$

that all the $p_{1st}^{sel}$-th features in the first-level features are selected and a scale factor $f_{DXN}^{RMSE}$ that has a default value of 1, a lower limit of a threshold configured to select the third-level features is set as $\theta_{DXN}^{downlimit}$ and calculated according to:

$$\theta_{DXN}^{downlink} = \text{floor}\left( f_{DXN}^{RMSE} \cdot \frac{1}{P_{1st}^{sel}} \sum_{p_{1st}^{sel}=1}^{P_{1st}^{sel}} f_{num}^{p_{1st}^{sel}} \right) \quad (25)$$

where floor(•) represents a function that returns integers. When $f_{DXN}^{RMSE}$ is 1, it means that the lower limit of the threshold is an average value of the numbers of times that all the first-level features are selected.

A maximum value $(f_{DXN}^{RMSE})_{max}$ and a minimum value $(f_{DXN}^{RMSE})_{min}$ of $f_{DXN}^{RMSE}$ are calculated according to $$\begin{cases} (f_{DXN}^{RMSE})_{max} = \dfrac{\max\left( f_{num}^{1_{1st}^{sel}}, \ldots, f_{num}^{p_{1st}^{sel}}, \ldots, f_{num}^{P_{1st}^{sel}} \right)}{\dfrac{1}{P_{1st}^{sel}} \sum_{p_{1st}^{sel}=1}^{P_{1st}^{sel}} f_{num}^{p_{1st}^{sel}}} \\ \\ (f_{DXN}^{RMSE})_{min} = \dfrac{\min\left( f_{num}^{1_{1st}^{sel}}, \ldots, f_{num}^{p_{1st}^{sel}}, \ldots, f_{num}^{P_{1st}^{sel}} \right)}{\dfrac{1}{P_{1st}^{sel}} \sum_{p_{1st}^{sel}=1}^{P_{1st}^{sel}} f_{num}^{p_{1st}^{sel}}} \end{cases} \quad (26)$$

A maximum value of the number of times at all the $p_{1st}^{sel}$-th features in the first-level features are selected is found based on an upper limit $\theta_{DXN}^{uplimit}$ of the threshold configured to select the third-level features, $$\theta_{DXN}^{uplimit} = \max\left( f_{num}^{1_{1st}^{sel}}, \ldots, f_{num}^{p_{1st}^{sel}}, \ldots, f_{num}^{P_{1st}^{sel}} \right). \quad (27)$$

The threshold is recorded as $\theta_{DXN}^{3rd}$ and is between $\theta_{DXN}^{downlimit}$ and $\theta_{DXN}^{uplimit}$. The third-level feature selection is performed according to $$\mu^p = \begin{cases} 1, & \text{if } f_{num}^{p_{1st}^{sel}} \geq \theta_{DXN}^{3rd} \\ 0, & \text{else } f_{num}^{p_{1st}^{sel}} < \theta_{DXN}^{3rd} \end{cases}, \quad (28)$$

where $$f_{num}^{p_{1st}^{sel}}$$

represents the number of times that the $p_{1st}^{sel}$-th feature in the first-level features is selected by running the GAPLS algorithm J times. $\mu^p$ represents a threshold selection criterion for selecting the third-level features. Feature variables of $\mu^p=1$ are sequentially stored in $X_{3rd}^{sel\_temp}$. The RMSE is calculated. $X_{3rd}^{sel\_temp}$ serves as input variables in the establishment of the PLS algorithm-based DXN detection model. $X_{3rd}^{sel}$ represents the third-level features selected from $X_{1st}^{sel}$ based on a feature selection threshold $\theta_{3rd}$ and empirical knowledge.

Values of the threshold $\theta_{DXN}^{3rd}$ between $\theta_{DXN}^{downlimit}$ and $\theta_{DXN}^{uplimit}$ are increased one by one so as to establish a plurality of first temporary PLS algorithm-based DXN detection model.

A second temporary PLS algorithm-based DXN detection model is selected from the plurality of first temporary PLS algorithm-based DXN detection models. The selected second temporary PLS algorithm-based DXN detection model has a minimum value of RMSE.

The input features of the WONT emission concentration detection model are checked to determine whether the input features include concentrations of CO, HCL, O₂ and NOₓ emitted from a chimney. Features in the common resource supply sub-process are removed. If the input features do not include concentrations of CO, HCL, O₂ and NOₓ, the third-level features are additionally selected to obtain features $X_{3rd}^{sel}$ selected from the third-level features, thereby varying the number of features that are selected and establishing the PLS algorithm-based DXN detection model based on prior knowledge.

In summary, the multi-level feature selection provided in the present application has the following process.

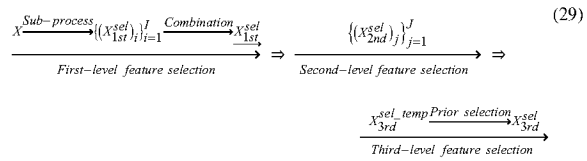

(29)

The principle of the method of the present embodiment will be described below in combination with implementation data.

1. Modeling Data Description

The method provided in the embodiment of the present application is implemented in a grate furnace-based MSWI plant in Beijing. The method includes 34 DXN emission concentration detection samples, and variables that include all process variables of the MSWI process has 287 dimensions. It can be seen that the number of input features far exceeds the number of modeling samples, and thus it is very necessary to reduce dimensionality of the variables. In the present embodiment, six sub-processes includes an incineration treatment sub-process, a boiler operation sub-process, a flue gas treatment sub-process, a steam electric power generation sub-process, a stack emission sub-process and a common resource supply sub-process, which are respectively marked as incineration, boiler, flue gas, steam, stack and common.

Figure 6:
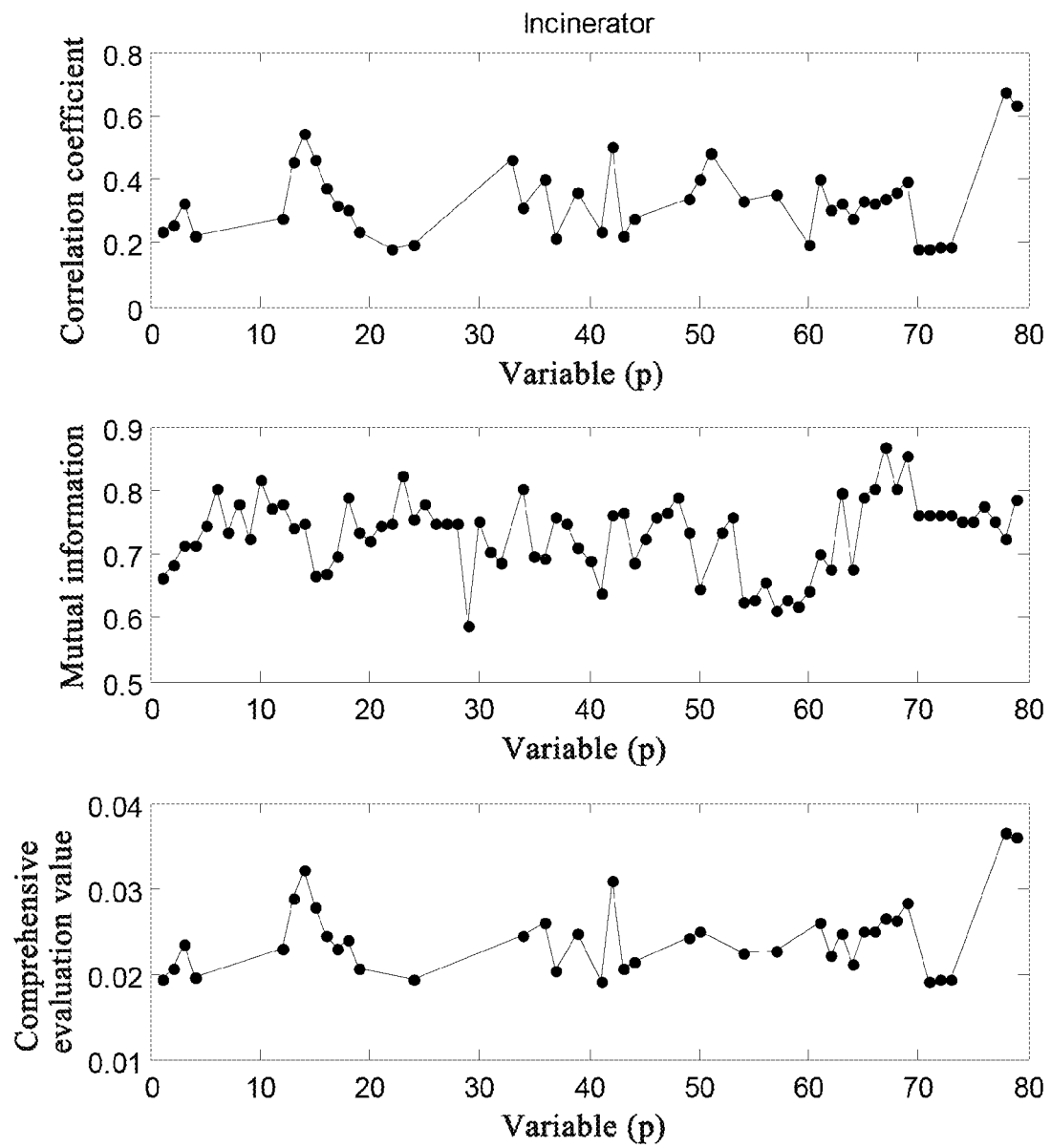
FIG. 6 shows correlation coefficient values, mutual information values and comprehensive evaluation values of process variables selected in an incineration treatment sub-process according to an embodiment of the present application.
Figure 7:
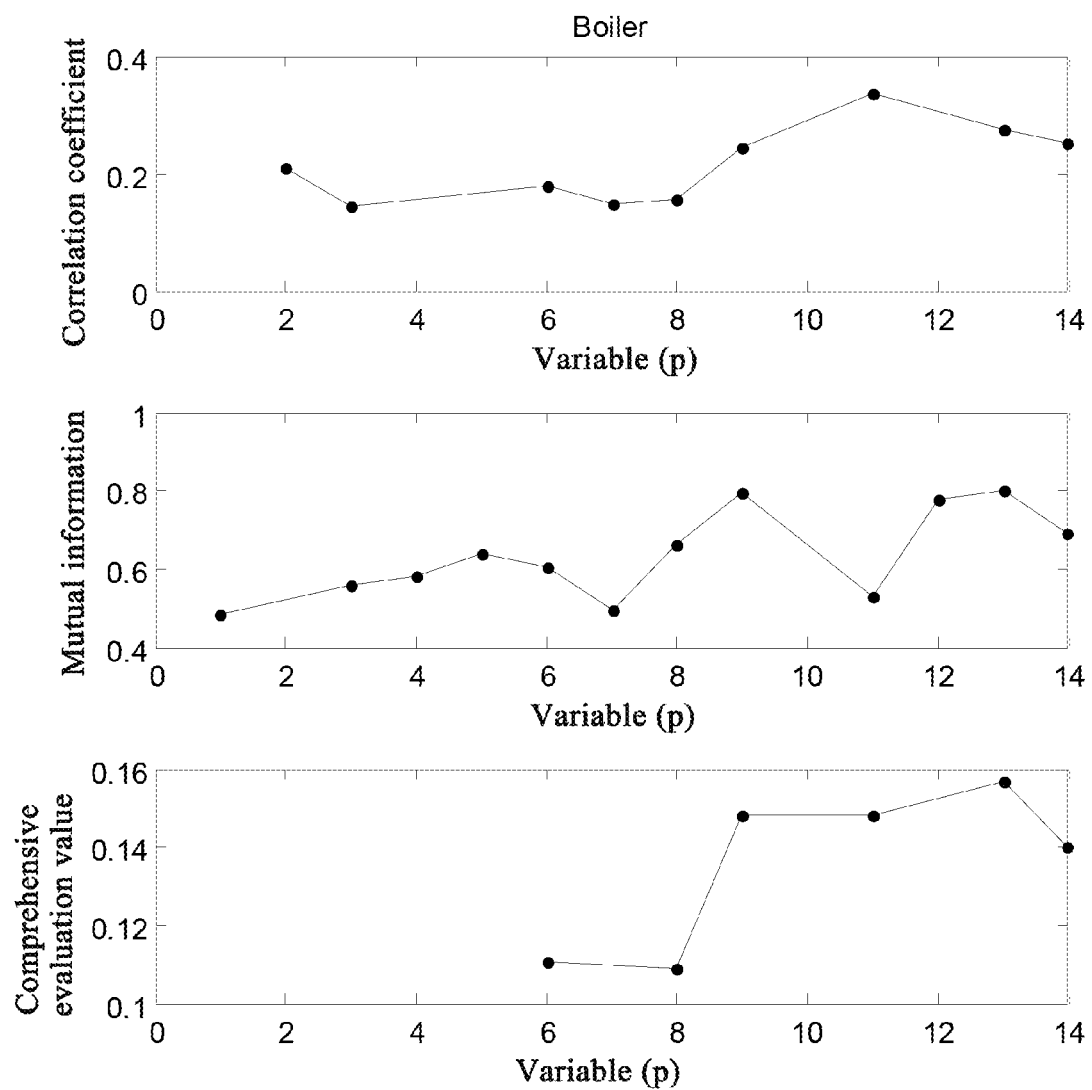
FIG. 7 shows correlation coefficient values, mutual information values and comprehensive evaluation values of process variables selected in a boiler operation sub-process according to an embodiment of the present application.
Figure 8:
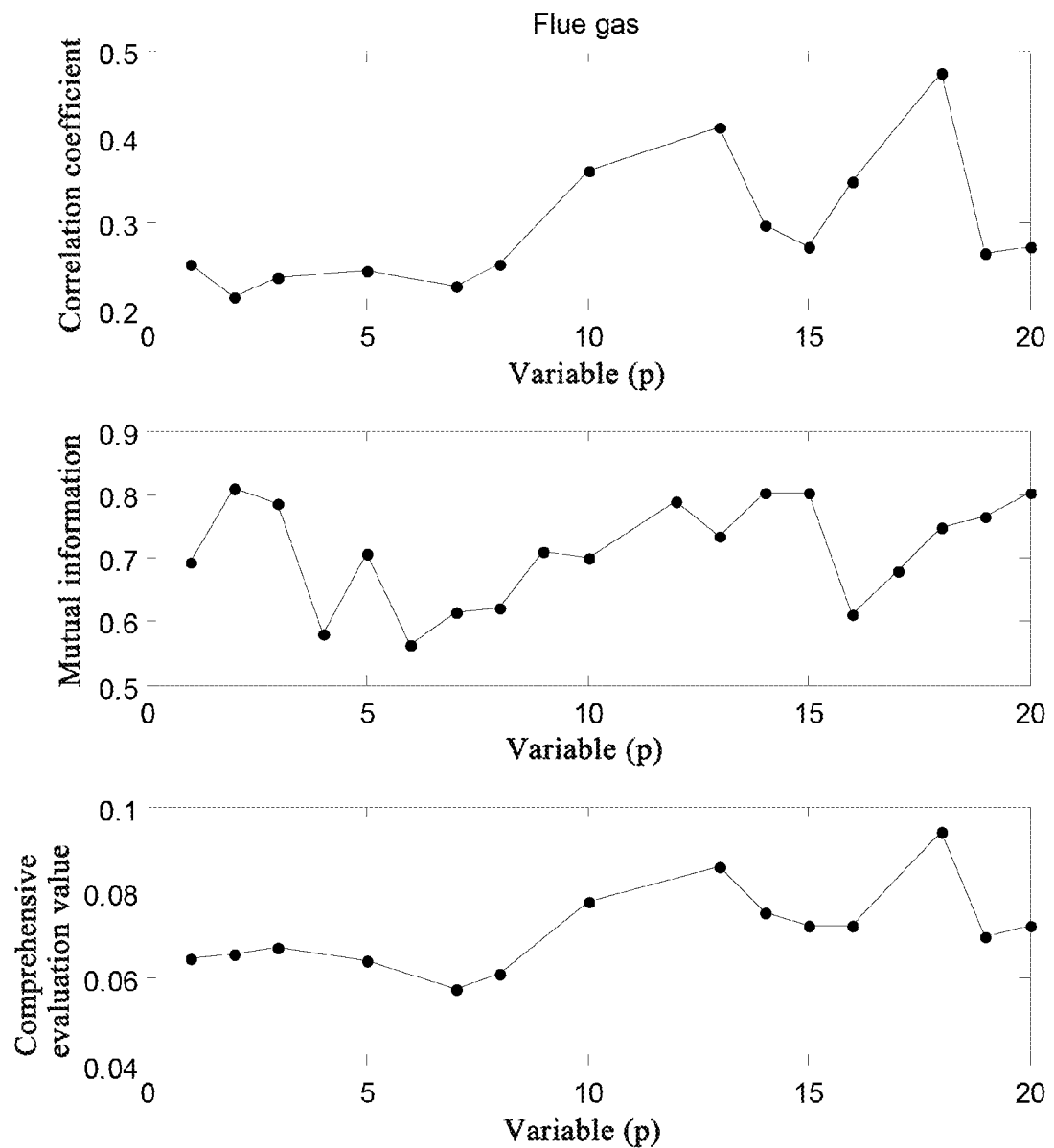
FIG. 8 shows correlation coefficient values, mutual information values and comprehensive evaluation values of process variables selected in a flue gas treatment sub-process according to an embodiment of the present application.
Figure 9:
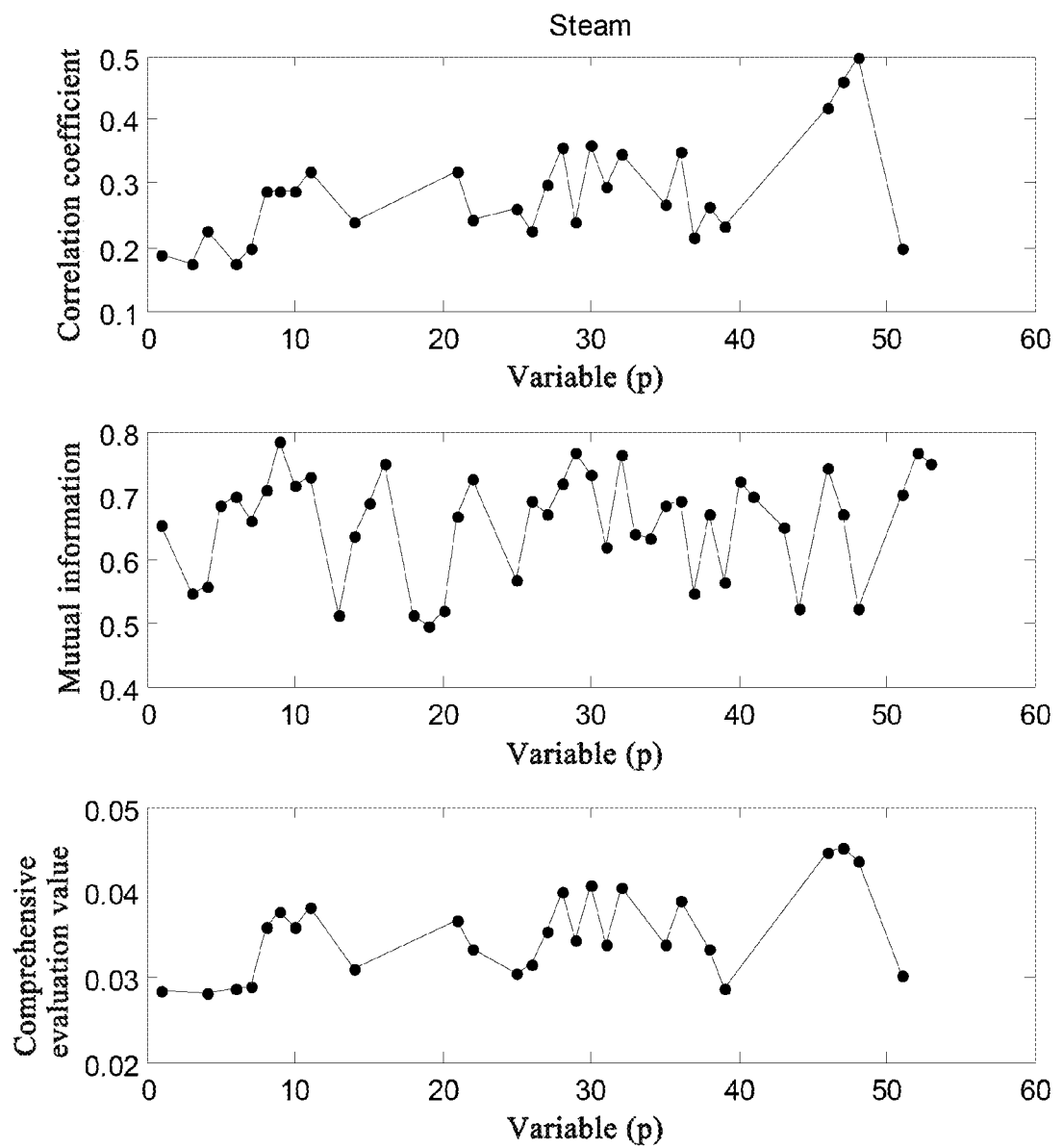
FIG. 9 shows correlation coefficient values, mutual information values and comprehensive evaluation values of process variables selected in a steam electric power generation sub-process according to an embodiment of the present application.
Figure 10:
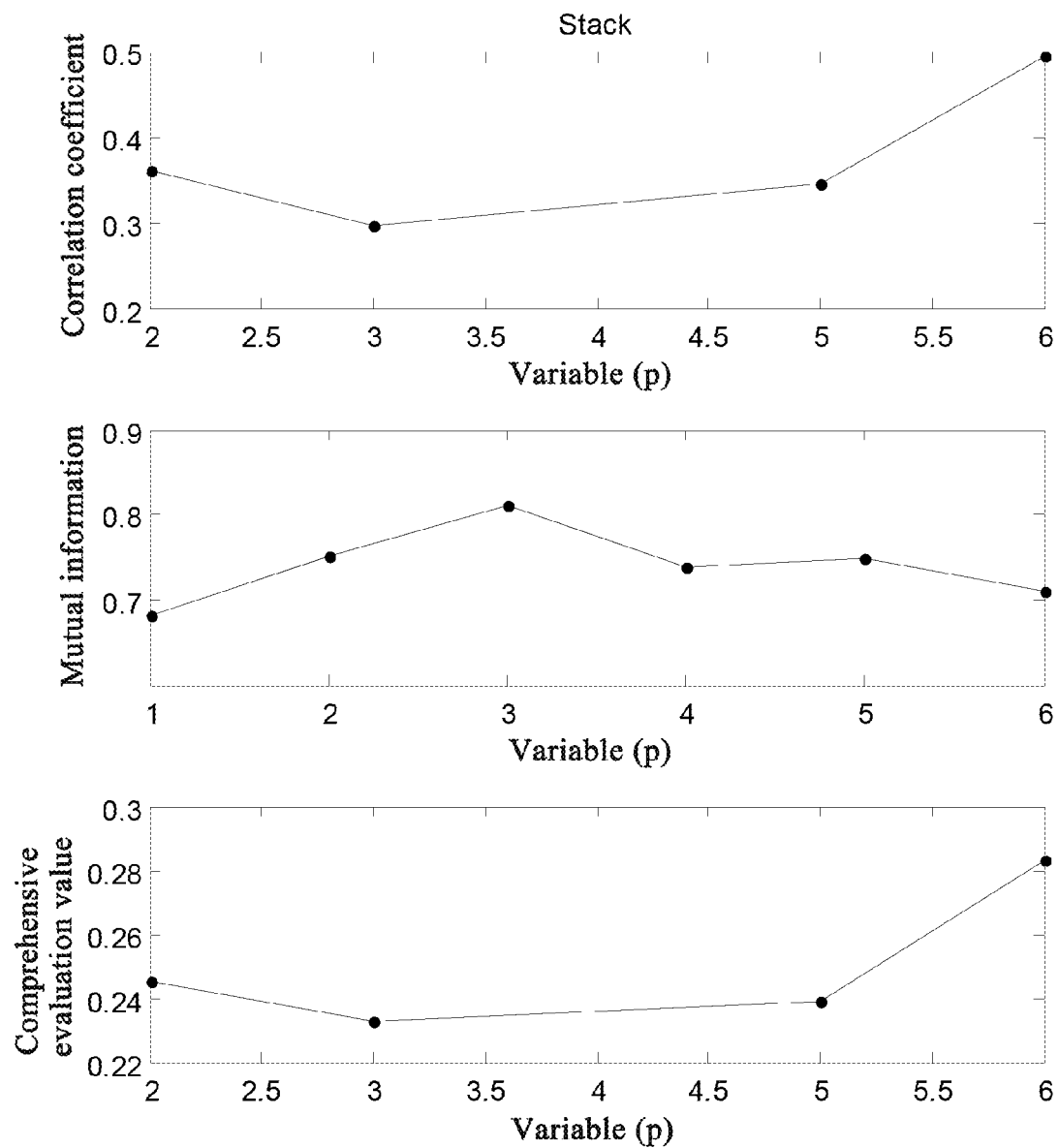
FIG. 10 shows correlation coefficient values, mutual information values and comprehensive evaluation values of process variables selected in a stack emission sub-process according to an embodiment of the present application.
Figure 11:
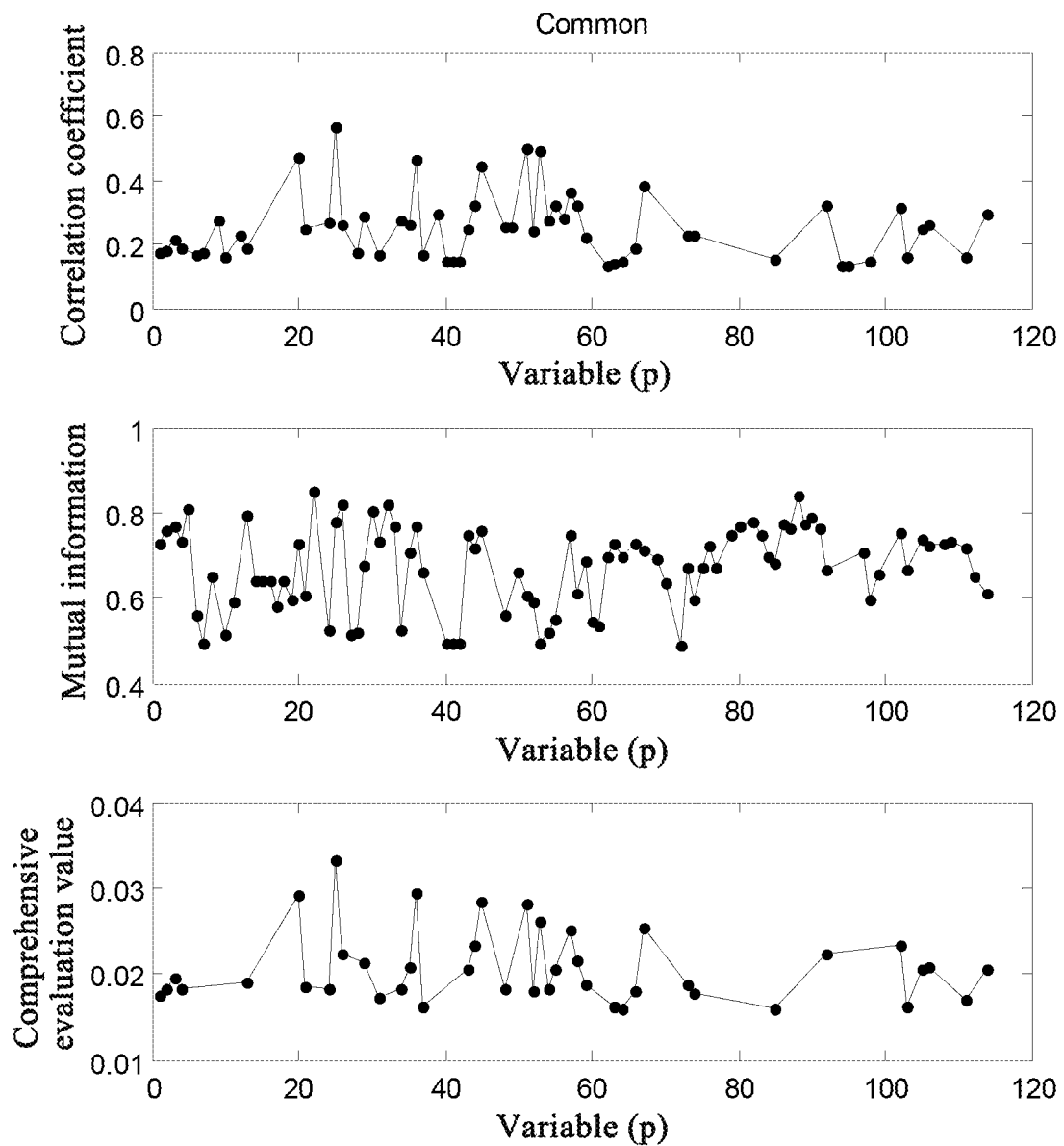
FIG. 11 shows correlation coefficient values, mutual information values and comprehensive evaluation values of process variables selected in a common resource supply sub-process according to an embodiment of the present application.

2. Modeling Results 2.1 Feature Selection Results Based on Single Feature Correlation For different sub-processes, feature selection weight factors $f_i^{corr}$, $f_i^{sel}$ and $f_t^{corr\_mi}$ of the correlation coefficient and the mutual information are 0.8. $k_i^{corr}$ is equal to 0.5. $k_i^{mi}$ is equal to 0.5. Correlation coefficient values, mutual information values and comprehensive evaluation values of process variables selected by the incineration treatment sub-process are shown in FIG. 6. Correlation coefficient values, mutual information values and comprehensive evaluation values of process variables selected by the boiler operation sub-process are shown in FIG. 7. Correlation coefficient values, mutual information values and comprehensive evaluation values of process variables selected by the flue gas treatment sub-process are shown in FIG. 8. Correlation coefficient values, mutual information values and comprehensive evaluation values of process variables selected by the steam electric power generation sub-process are shown in FIG. 9. Correlation coefficient values, mutual information values and comprehensive evaluation values of process variables selected by the stack emission sub-process are shown in FIG. 10. Correlation coefficient values, mutual information values and comprehensive evaluation values of process variables selected by the common resource supply sub-process are shown in FIG. 11.

It can be seen from FIGS. 6-11 that the correlation coefficient values, the mutual information values and the comprehensive evaluation values of the process variables are different for respective sub-processes. As shown in FIG. 12, minimum, mean and maximum values of the correlation coefficient values are calculated; minimum, mean and maximum values of the mutual information values are calculated; minimum, mean and maximum values of the comprehensive evaluation values are calculated. FIG. 12 is a statistical table of correlation measurement results of the process variables of the respective sub-processes according to an embodiment of the present application.

Four conclusions can be obtained from FIG. 12.

(1) The stack emission sub-process has mean values of 0.2816, 0.7401 and 0.2500 for the correlation coefficient values, the mutual information values and the comprehensive evaluation values, and these mean values of the stack emission sub-process are higher than those of other sub-processes. In the stack emission sub-process, concentrations of gases such as HCL, O₂, NOₓ and CO emitted with DXN from the chimney are measured, which is consistent with DXN generation mechanism and DXN emission detection disclosed in literatures.

(2) For the incineration treatment sub-process, its correlation coefficient values have a maximum value of 0.6760, which is higher than that of other sub-processes. For the incineration treatment sub-process, its mutual information values have a maximum value of 0.8665, which is higher than that of other sub-process. For the stack emission sub-process, its comprehensive evaluation values have a maximum value of 0.2877, which is higher than other sub-processes. Therefore, the incineration treatment sub-process, the stack emission sub-process are related to the DXN generation process.

(3) For the common resource supply sub-process, its correlation coefficient values, mutual information values and comprehensive evaluation values each have a minimum value that is smallest among different sub-processes. In terms of mechanism, the common resource supply sub-process is not directly related to the material flow produced by DXN. However, it can be seen from measurement results of single feature correlation that the correlation coefficient value and the mutual information value between some process variables of the common resource supply sub-process and DXN are relatively large.

(4) The above statistics show that DXN emission industrial data has a certain degree of reliability. From the perspective of single feature correlation, the top three systems are related to DXN generation, adsorption and emission. However, some process variables of other sub-processes are also highly correlated with the DXN emission concentration from the data perspective, and thus the final feature selection should be performed by combining mechanism knowledge.

FIG. 13 is a table of the number of process variables selected based on the comprehensive evaluation value according to an embodiment of the present application.

With reference to FIGS. 6-11 and FIG. 13, it can be seen that the number of features selected based on correlation coefficient and the number of features selected based on mutual information are different. The number of feature variables selected based on the comprehensive evaluation value is 132. Among the 132 feature variables, 39 feature variables are from the incineration treatment sub-process and 42 feature variables are from the common resource supply sub-process. Therefore, most feature variables are from the incineration treatment sub-process and the common resource supply sub-process. Moreover, all the sub-process provide process variables, that is, each sub-process contributes features for subsequent variable selection, thereby helping subsequent independent analysis of the different sub-processes.

2.2 Feature Selection Results Based on Multiple Feature Redundancy

For the 132 process variables based on single feature correlation, an optimal process variable combination is determined using the GAPLS algorithm for the redundant feature removal.

The GAPLS algorithm adopts the operating parameters of a population size 20, a maximum genetic algebra 40, a maximum number of latent variables (LV) 6, a genetic variation rate 0.005, a window width 1, a convergence percentage 98% and a variable initialization percentage 30%.

After the GAPLS algorithm runs 100 times with the above parameters, RMSE statistical results of the prediction model are obtained and shown in FIG. 14.

It can be seen from the statistical results of FIG. 14, GAPLS operating results have a relatively greater fluctuation, which is related to small sample size of modeling and the randomness of the genetic algorithm (GA). The number of the prediction model obtained by the GAPLS algorithm that is greater than a prediction average value is counted to be 49.

Further, the number of times that the 132 process variables are calculated. Statistical results of the number of times that the multi-feature related process variables are selected are shown in FIG. 15. Three conclusions can be obtained from FIG. 15.

(1) The average number of times that all 132 process variables are selected is 13. A process variable that has the largest selection times is from the common resource supply sub-process.

(2) The stack emission sub-process has four process variables, and these four process variables have largest single feature correlation. The maximum number of times that respective four process variables are selected is only 6, so it can be concluded that there is a difference between the selection results based on multiple feature redundancy and the single feature correlation. It also can be concluded that the GAPLS algorithm has randomness.

(3) The data-driven feature variable selection is flawed, and it is required to supplement mechanism knowledge.

2.3 Feature Selection Results Based on Model Prediction Performance

Based on the above GAPLS running results, a feature selection threshold is set to be in a range of 13-48.

According to the relationship between the feature selection threshold and the prediction performance, the threshold is set to be 18, and the number of selected process variables is 39. The process variables selected based on the model prediction performance in the respective sub-processes are shown in FIG. 16.

It can be seen from FIG. 16 that the input feature dimension is reduced to 39. There are 14 features related to the DXN generation mechanism, in which seven features belong to combustion treatment; six features belong to exhaust gas treatment and one feature belongs to boiler operation. The above-mentioned process variables based on data-driven selection were used to establish a PLS model.

According to a relationship between the number of LVs and the RMSE of the prediction performance, when the number of LVs is 2, the training RMSE is 0.01375 and the testing RMSE is 0.01929. Latent variable contribution rates are extracted from different latent variables (LV). FIG. 17 is a table showing LV contribution rates of PLS models based on different input features according to an embodiment of the present application.

According to DXN generation mechanism, the steam electric power generation sub-process and the common resource supply sub-process are weakly correlated to the DXN emission concentration. The stack emission sub-process is related to DXN. By combining the mechanism, four process variables of the stack emission sub-process are added as input features. The four process variables are concentrations of HCL, $O_2$, $NO_x$ and CO emitted from the chimney.

The above-mentioned 18 process variables selected based on the combination of data drive and mechanism are used to establish the PLS model.

According to a relationship between the number of LVs and the RMSE of the prediction performance, when the number of LVs is 2, the training RMSE is 0.01638 and the testing RMSE is 0.02048. Variables extracted by different LVs and LV contribution rates are shown in FIG. 17.

It can be seen from FIG. 17 that after adding the process variables determined based on the mechanism knowledge, the contribution rate of LV in the input data increases by 2%, and the contribution rate of LV in the output data decreases by 2%. It can be seen that the removal and addition of the process variables have a limited impact on the prediction performance. DXN modeling data preprocessing is performed by equalizing 24-hour data, and the corresponding DXN detection value is obtained by continuously sampling for 4-6 hours followed by offline testing for one week, and thus uncertainties are inevitably introduced during the treatment process. At the same time, it is appropriate to introduce some process variables related to the mechanism at the cost of introducing smaller prediction errors. Specific and more in-depth mechanism analysis needs to be carried out in depth combined with the numerical simulation study of the DXN emission process. Mechanism analysis requires to be combined with numerical simulation study of the DXN emission process to reach a more profound level.

3. Comparison and Discussion

It can be seen from the above that the method provided herein can reasonably consider the contribution of correlation coefficients and mutual information measures. A soft-sensing model based on the different input features is established using the PLS algorithm. FIG. 18 is a table showing statistical results of PLS models based on the different input features according to an embodiment of the present application.

From the above results, it can be seen that, with the same number of LV, PLS modeling methods based on the different input features have similar prediction performance for testing data, but have a significant gap in the dimensionality reduction of the input features. Dimensions of the input features are listed in descending order. The original features have 287 dimensions. The input features based on mutual information have 235 dimensions. The input features based on correlation coefficients have 153 dimensions. The input features based on comprehensive evaluation values have 98 dimensions. The input features based on both of mechanism and the data drive in this application have 18 dimensions. It can be seen that the number of features in the method provided herein has been reduced by 16 times. Therefore, the method in the present application can effectively establish an interpretable soft-sensing model with clear physical meaning. It also shows that the analysis of industrial process data needs to be combined with mechanism knowledge for the implementation.

Multiple feature selection coefficients are involved in the feature selection of the present application. The influence of these coefficients on the feature selection results and model prediction performance requires to be profoundly analyzed. In addition, the modeling method used in this application is a simple linear model, and the selected features are linear and nonlinear mixed features. Therefore, a more reasonable modeling strategy remains to be studied. It is also needed to further explore the approach of measuring the reliability of the industrial process data. In view of the input features with clear mechanism knowledge, it is necessary to consider the use of prior knowledge in the initialization of the genetic algorithm, so as to select process variables with strong mechanism correlation, such as the concentration of CO emitted from the chimney.

In order to address the problems that DXN, as a highly toxic by-product of the MSWI process, has complicated and unclear generation and emission mechanism and is hardly detected online in real time, and high-dimensional input features used for DXN detection fail to be effectively selected, and there are a limited modeling sample size. The present application provides a method for detecting the DXN emission concentration in the MSWI process based on multi-level feature selection, which has the following advantages.

(1) Comprehensive evaluation value indicators are defined to perform single feature selection and measurement based on correlation.

(2) A feature selection method by running GAPLS multiple times for multiple feature redundancy is provided.

(3) Based on the model prediction performance, data drive and mechanism knowledge are combined to select the final input features, so as to establish a detection model. The method provided in the present application is verified to be effective by an incineration plant.

References cited in the specification are listed as follows:

[ ] Arafat A, Jijakli K, Ahsan A. Environmental performance and energy recovery potential of five processes for municipal solid waste treatment[J]. Journal of Cleaner Production, 2015, 105: 233-240.

[2] Zhou H, Meng A, Long Y Q, Li Q H, and Zhang Y G. A review of dioxin-related substances during municipal solid waste incineration[J]. Waste Management, 36: 106-118, 2015.

[3] Mukheijee A, Debnath B, Ghosh S K. A Review on Technologies of Removal of Dioxins and Furans from Incinerator Flue Gas[J]. Procedia Environmental Sciences, 2016, 35:528-540.

[4] Yuanan H, Hefa C, Shu T. The growing importance of waste-to-energy (WTE) incineration in China's anthropogenic mercury emissions: Emission inventories and reduction strategies[J]. Renewable and Sustainable Energy Reviews, 2018, 97:119-137.

[5] Huang T, Zhou L, Liu L, Xia M. Ultrasound-enhanced electrokinetic remediation for removal of Zn, Pb, Cu and Cd in municipal solid waste incineration fly ashes[J]. Waste Management, 2018, 75: 226-235.

[6] Jones P H, Degerlache J, Marti E, Mischer G, Scheirer M C, Bontinck M J, Niessen H J, The global exposure of man to dioxins—a perspective on industrial-waste incineration [J]. Chemo sphere, 26 (1993) 1491-1497.

[7] Bai j, Sun X, Zhang C, Gong C, Hu J, Zhang J. Mechanism and kinetics study on the ozonolysis reaction of 2, 3, 7, 8-TCDD in the atmosphere[J]. Journal of Environmental Sciences, 2014, 26(1): 181-188.

[8] Yu Ming Feng, Fu Ran Ying, Zhan Ming Xiu. The research of PCDD/Fs emission characteristics in flue gas from municipal solid waste incinerations[J]. Acta Scientiae Circumstantiae, 2018, 38(05): 1983-1988.

[9] Gouin. T, Daly T H L, Wania F, Mackay D, Jones K C. Variability of concentrations of polybrominated diphenyl ethers and polychlorinated biphenyls in air: implications for monitoring, modeling and control[J]. Atmospheric Environment, 2005, 39(1):151-166.

[0] Zhang H J, Ni Y W, Chen J P, Zhang Q. Influence of variation in the operating conditions on PCDD/F distribution in a full-scale MSW incinerator[J]. Chemosphere, 2008, 70(4):721-730.

[1] Qiao J F, Guo Z H, Tang J. Dioxin Emission Concentration Measurement Approaches for Municipal Solid Wastes Incineration Process: A Survey[J]. Acta Automatica Sinica, 2020, 46(6):1063-1089.

[2] Chang N B, Huang S H. Statistical modelling for the prediction and control of PCDDs and PCDFs emissions from municipal solid waste incinerators[J]. Waste Management & Research, 1995, 13, 379-400.

[3] Chang N B, Chen W C. Prediction of PCDDs/PCDFs emissions from municipal incinerators by genetic programming and neural network modeling[J]. Waste Management & Research, 2000, 18(4) 41-351.

[4] Tang J, Qiao J. F. Dioxin emission concentration soft measuring approach of municipal solid waste incineration based on selective ensemble kernel learning algorithm[J], Journal of Chemical Industry and Engineering (China), 2019, 70(02):696-706.

[5] Bunsan S, Chen W Y, Chen H W, Chuang Y H, Grisdanurak N. Modeling the dioxin emission of a municipal solid waste incinerator using neural networks [J] Chemosphere, 2013, 92: 258-264.

[6] Xiao X D, Lu J W, Hai J. Prediction of dioxin emissions in flue gas from waste incineration based on support vector regression[J], Renewable Energy Resources, 2017, 35(8):1107-1114.

[7] Tang J, Qiao J F, Guo Z H. Soft Sensing of Dioxin Emission Concentration Based on Potential Characteristic Selective Integrated Modeling[J]. Acta Automatica Sinica, in trial.

[8] Hasnat A, Molla. A U. Feature selection in cancer microarray data using multi-objective genetic algorithm combined with correlation coefficient[A]. 2016 International Conference on Emerging Technological Trends (ICETT)[C]. 2016: 1-6.

[9] Coelho F, Braga A P, Verleysen. M. Multi-Objective Semi-Supervised Feature Selection and Model Selection Based on Pearson's Correlation Coefficient[A]. Iberoamerican Congress on Pattern Recognition. Springer [C], Berlin, Heidelberg, 2010: 509-516.

[20] Battiti R. Using mutual information for selecting features in supervised neural net learning[J]. IEEE Transactions on. Neural Networks, 1994, 5(4):537-550.

[2] Vergara J R, Estévez P A. A review of feature selection methods based on mutual information[J]. Neural computing and applications, 2014, 24(1): 175-186.

[22] Jain A K, Duin R P W, Mao J. Statistical pattern recognition: A review[J] IEEE Transactions on pattern analysis and machine intelligence, 2000, 22(1): 4-37.

[23] Fleuret F. Fast binary feature selection with conditional mutual information[J]. Journal of Machine Learning Research, 2004, 5: 1531-1555.

[24] Coelho F, Braga A P, Verleysen M. Multi-Objective Semi-Supervised Feature Selection and Model Selection Based on Pearson's Correlation Coefficient[J]. Lecture Notes in Computer Science, 2010, 6419:509-516.

[25] Estévez P A, Tesmer M, Perez C A, Zurada J M. Normalized mutual information feature selection [J]. IEEE Transactions on Neural Networks, 2009, 20(2):189-201.

[26] Amiri F, Yousefi M M R, Lucas C, Shakery A, Yazdani N. Mutual information-based feature selection for intrusion detection systems[J]. Journal of Network and Computer Applications, 34 (2011) 1184-1199.

[27] Mohammadi S, Mirvaziri H, Ghazizadehahsaee M. Multivariate correlation coefficient and mutual information-based feature selection in intrusion detection[J]. Information Security Journal A Global Perspective, 2017, 26(5):229-239.

[28] Peng H, Long F, Ding C. Feature selection based on mutual information criteria of max-dependency, max-relevance, and min-redundancy[J]. IEEE Transactions on pattern analysis and machine intelligence, 2005, 27(8): 1226-1238.

[29] Tang J, Tian F Q, Jia M Y. Soft Measurement of Rotating Machinery Equipment Load Based on Spectrum Data Drive[M]. Beijing: National Defense Industry Press, 2015.

[30] Tihonov A N. Solution of incorrectly formulated problems and the regularization method[J]. Soviet Math, 1963, 4: 1035-1038.

[30] Wold S, Ruhe A, Wold H, Dunn III W J. The collinearity problem in linear regression. The partial least squares (PLS) approach to generalized inverses[J]. SIAM Journal on Scientific and Statistical Computing, 1984, 5(3): 735-743.

[32] Leardi R, Boggia R, Terrile M. Genetic algorithms as a strategy for feature selection[J]. Journal of chemometrics, 1992, 6(5): 267-281.

[33] TANG J, CHAI T Y, ZHAO L J, YUE H, ZHENG X P. Soft sensing mill load in grinding process by time/frequency information fusion[J]. Control Theory and Applications, 2012, 29(5): 564-570.

[34] Bunsan S, Chen W Y, Chen H W, Chuang Y H, Grisdanurak N. Modeling the dioxin emission of a municipal solid waste incinerator using neural networks [J]. Chemosphere, 2013, 92: 258-264.

It can be understood by those skilled in the art that, all or part of steps of the method disclosed in the present application can be completed by relevant hardware under the instructions of a program. The program is stored on a storage medium which includes several instructions to cause a computing device (such as a single-chip microcomputer, a chip, etc), or a processor to execute all or part of the steps of the method in the embodiments of the present application. The storage media is selected from various media that can store program codes consisting of a USB flash disk, a mobile hard disk, a Read-Only Memory (ROM), a Random-Access Memory (RAM), a diskette and an optical disc.

It should be understood by those skilled in the art that, in actual applications, various changes can be made without departing from the spirit and scope of the disclosure as claimed.

It should be noted that terms used herein are only for the purpose of description and are not intended to limit the present application. Unless otherwise specified, terms of a singular form also include a plural form. In addition, the terms "comprise" and/or "include" used in the specification are intended to indicate the presence of features, steps, operations, devices, components, and/or a combination thereof.

Unless otherwise specified, the relative arrangement of components and numerical expressions and numerical values in steps in the embodiments are not intended to limit the scope of the present application. At the same time, it should be understood that, the words used in the specification are words of description rather than limitation. The techniques, methods and equipment known to those skilled in the art may not be discussed in detail, but can be regarded as a part of the disclosure as claimed under certain cases. Any specific value disclosed in an embodiment is merely illustrative and is not as a limitation, and thus can be modified in other embodiments. It should be noted that similar numbers and letters indicate similar items in the accompanying drawings. Therefore, once an item is defined in an accompanying drawing, and there is no need to further define it in the subsequent accompanying drawings.

The embodiments disclosed in the present application are merely preferred embodiments. Any changes, modifications and replacements made by those skilled in the art without departing from the spirit of the invention are defined by the scope of the appended claims and equivalents thereof.

What is claimed is:

1. A computer-implemented method for detecting a dioxin (DXN) emission concentration in a municipal solid waste incineration (MSWI) process based on multi-level feature selection, comprising the steps of:

1. dividing a grate furnace-based municipal solid waste incineration (MSWI) process into a plurality of sub-processes based on an incineration process; wherein the plurality of sub-processes comprise an incineration treatment sub-process, a boiler operation sub-process, a flue gas treatment sub-process, a steam electric power generation sub-process, a stack emission sub-process and a common resource supply sub-process;

2. obtaining a correlation coefficient value and a mutual information value between each of original input features of the sub-processes and the DXN emission concentration; and obtaining a comprehensive evaluation value of candidate input features according to the obtained correlation coefficient value and the obtained mutual information value, thereby completing the selection of first-level features of all of the sub-processes;

3. selecting and statistically processing the first-level features by adopting a feature selection algorithm based on genetic algorithm-based partial least squares (GAPLS) and according to redundancy between different features, thereby completing the selection of second-level features of all of the sub-processes;

4. performing a third-level feature selection according to the first-level features and statistical results of the second-level features within a preset threshold range, thereby completing the selection of third-level features of all of the sub-processes; and 5. establishing a partial least squares (PLS) algorithm-based DXN detection model according to model prediction performance and the third-level features; and detecting the DXN emission concentration by the obtained PLS algorithm-based DXN detection model, wherein the step of establishing the PLS algorithm-based DXN detection model comprises a microprocessor performing the steps of:

increasing values of a third-level feature selection threshold $\theta_{DXN}^{3rd}$ between $\theta_{DXN}^{downlimit}$ and $\theta_{DXN}^{uplimit}$ one by one, so as to establish a plurality of first temporary PLS algorithm-based DXN detection models, wherein $\theta_{DXN}^{downlimit}$ is a lower limit of the threshold $\theta_{DXN}^{3rd}$, and $\theta_{DXN}^{uplimit}$ is a upper limit of the threshold $\theta_{DXN}^{3rd}$;

selecting a second temporary PLS algorithm-based DXN detection model from the plurality of first temporary PLS algorithm-based DXN detection models, wherein the second temporary PLS algorithm-based DXN detection model has a minimum value of root mean square error (RMSE); and checking the input features of the DXN emission concentration detection model to determine whether the input features comprise concentrations of CO, HCl, $O_2$ and $NO_x$ emitted from a chimney, and removing features in the common resource supply sub-process; if the input features do not include concentrations of CO, HCl, $O_2$ and $NO_x$, additionally selecting the third-level features to obtain selected three-level features $X_{3rd}^{sel}$, thereby varying a number of features that are selected and establishing the PLS algorithm-based DXN detection model.

2. The method of claim 1, further comprising:
arranging the first-level features in series after the step of obtaining the first-level features of all of the sub-processes so as to obtain the first-level features based on a single feature correlation.

3. The method of claim 2, wherein the DXN detection model comprises input data and output data;
wherein the input data is expressed as $X \in R^{N \times P}$ and comprises N samples as row data and P variables as column data; the input data is derived from the sub-processes of the MSWI process; monitoring data of an i-th sub-process is obtained by using a programmable logic controller (PLC) device or a distributed control system (DCS) device installed on site and is expressed as $X_i \in R^{N \times P_i}$; and $X_i \in R^{N \times P_i}$ is input data from the i-th sub-process and satisfies Equations (1) and (2);

$$X = [X_1, L, X_i, L, X_I] = \{X_i\}_{i=1}^{I} \tag{1}$$

$$P = P_1 + L + P_i + L + P_I = \Sigma_{i=1}^{I} P_i \tag{2}$$

wherein I represents the number of the sub-processes, and $P_i$ represents the number of input features in the i-th sub-process;

$X_i$ is expressed as:

$$X_i = \left[ \{(x_n^1)_i\}_{n=1}^{N}, \ldots, \{(x_n^{p_i})_i\}_{n=1}^{N}, \ldots, \{(x_n^{P_i})_i\}_{n=1}^{N} \right] \tag{3}$$
$$= \left[ (x^1)_i, \ldots, (x^{p_i})_i, \ldots, (x^{P_i})_i \right]$$
$$= \{(x^{p_i})_i\}_{p_i=1}^{P_i}$$

wherein $(x^{p_i})_i$ represents a $p_i$-th input feature of the i-th sub-process; and $x^{p_i} = \{x_n^{p_i}\}_{n=1}^{N}$ represents a column vector; and wherein the output data is expressed as $y = \{y_n\}_{n=1}^{N} \in R^{N \times 1}$, and comprises N samples; and $\hat{y}$ represents a predicted value.

4. The method of claim 3, wherein the step of obtaining the correlation coefficient value comprises:

1.1) calculating an original correlation coefficient value between each of the original input features and the DXN emission concentration, wherein an original correlation coefficient value between a p-th input feature $(x^{p_i})_i = \{(x_n^{p_i})_i\}_{n=1}^{N}$ of the i-th sub-process and the DXN emission concentration is calculated according to $$\left( \xi_{corr\_ori}^{p_i} \right)_i = \frac{\sum_{n=1}^{N} \left[ ((x_n^{p_i})_i - \bar{x}_{p_i})(y_n - \bar{y}) \right]}{\sqrt{\sum_{n=1}^{N} ((x_n^{p_i})_i - \bar{x}_{p_i})^2} \sqrt{\sum_{n=1}^{N} (y_n - \bar{y})^2}} \tag{4}$$

wherein $\bar{x}_{p_i}$ represents an average value of the p-th input feature of the i-th sub-process; and $\bar{y}1$ represents an average value of N modeling samples of the DXN emission concentration;

1.2) preprocessing the original correlation coefficient value $(\xi_{corr\_ori}^{p_i})_i$ as follows:

$$(\xi_{corr}^{p_i}) = |(\xi_{corr\_ori}^{p_i})_i| \tag{5}$$

wherein |•| represents an absolute value;

1.3) repeating steps (1.1)-(1.2) until correlation coefficient values of all of the original input features are obtained; and recording the obtained correlation coefficient values as $\{\xi_{corr}^{p_i}\}_{p_i=1}^{P_i}$;

1.4) setting a weight factor of the i-th sub-process as $f_i^{corr}$; calculating a threshold $\theta_i^{corr}$ configured to select correlation coefficient-based input features according to $$\theta_i^{corr} = f_i^{corr} \cdot \frac{1}{p_i} \sum_{p_i=1}^{P_i} (\xi_{corr}^{p_i})_i \tag{6}$$

wherein a maximum value $(f_i^{corr})_{max}$ and a minimum value $(f_i^{corr})_{min}$ of $f_i^{corr}$ are calculated according to Equation (7):

$$\begin{cases} (f_i^{corr})_{max} \dfrac{\max((\xi_{corr}^1)_i, \ldots, (\xi_{corr}^{p_i})_i, \ldots, (\xi_{corr}^{P_i})_i)}{\dfrac{1}{p_i}\sum_{p_i=1}^{P_i}(\xi_{corr}^{p_i})_i} \\ (f_i^{corr})_{min} = \dfrac{\min((\xi_{corr}^1)_i, \ldots, (\xi_{corr}^{p_i})_i, \ldots, (\xi_{corr}^{P_i})_i)}{\dfrac{1}{p_i}\sum_{p_i=1}^{P_i}(\xi_{corr}^{p_i})_i} \end{cases} \quad (7)$$

wherein max(•) is a function for finding a maximum value; and min(•) is a function for finding a minimum value;

1.5) selecting the p-th input feature of the i-th sub-process according to rules as follows:

$$\alpha_i^{p_i} = \begin{cases} 1, & \text{if } (\xi_{corr}^{p_i})_i \geq \theta_i^{corr} \\ 0, & \text{else } (\xi_{corr}^{p_i})_i < \theta_i^{corr} \end{cases} \quad (8)$$

wherein $\theta_i^{corr}$ is taken as a threshold;

1.6) selecting a feature $(x^{p_i})_i$ in $\alpha_i^{p_i}=1$ as a correlation coefficient-selected candidate feature; and recording the correlation coefficient-selected candidate feature as $$\left(x^{(p_i)_{corr}^{sel}}\right)_i;$$

1.7) performing steps (1.1)-(1.6) for all of the original input features of the i-th sub-process; and recording the selected candidate features as:

$$(X_{corr}^{sel})_i = \left[(x^1)_i, \ldots, \left(x^{(p_i)_{corr}^{sel}}\right)_i, \ldots, \left(x^{(P_i)_{corr}^{sel}}\right)_i\right] \quad (9)$$

wherein $(P_i)_{corr}^{sel}$ represents the number of correlation coefficient-selected process variables of the i-th sub-process; and $(X_{corr}^{sel})_i$ represents a correlation coefficient-selected candidate feature set selected from the input features of the i-th sub-process; and 1.8) repeating steps (1.1)-(1.7) for all the sub-processes; and recording correlation coefficient measurement-selected features as $\{(X_{corr}^{sel})_i\}_{i=1}^I$.

5. The method of claim 4, wherein the step of obtaining the mutual information value comprises:

2.1) calculating the mutual information value between each of the original input features and the DXN emission concentration, wherein the mutual information value between the p-th input feature $(x^{p_i})_i$ of the i-th sub-process and the DXN emission concentration is calculated according to $$(\xi_{mi}^{p_i})_1 = \sum_{n=1}^{N}\sum_{n=1}^{N}\left\{p_{rob}((x_n^{p_i})_i, y_n)\log\left(\frac{p_{ob}((x_n^{p_i})_i, y_n)}{p_{rob}((x_n^{p_i})_i)p_{rob}(y_n)}\right)\right\} \quad (10)$$

wherein $p_{rob}((x_n^{p_i})_i, y_n)$ represents a joint probability density; and $p_{rob}((x_n^{p_i})_i)$ and $p_{rob}(y_n)$ each represent a marginal probability density;

2.2) repeating step (2.1) until mutual information values of all of the original input features are obtained; and recording the obtained mutual information values as $\{\xi_{mi}^{p_i}\}_{p_i=1}^{P_i}$;

2.3) setting a weight factor of the i-th sub-process as $f_i^{mi}$, and calculating a threshold $\theta_i^{mi}$ configured to select the input features based on the mutual information value according to $$\theta_i^{mi} = f_i^{mi} \cdot \frac{1}{p_i}\sum_{p_i=1}^{P_i}(\xi_{mi}^{p_i})_i \quad (11)$$

wherein a maximum value $(f_i^{mi})_{max}$ and a minimum value $(f_i^{mi})_{min}$ of $f_i^{mi}$ are calculated according to $$\begin{cases} (f_i^{mi})_{max} \dfrac{\max((\xi_{mi}^1)_i, \ldots, (\xi_{mi}^{p_i})_i, \ldots, (\xi_{mi}^{P_i})_i)}{\dfrac{1}{p_i}\sum_{p_i=1}^{P_i}(\xi_{mi}^{p_i})_i} \\ (f_i^{mi})_{min} = \dfrac{\min((\xi_{mi}^1)_i, \ldots, (\xi_{mi}^{p_i})_i, \ldots, (\xi_{mi}^{P_i})_i)}{\dfrac{1}{p_i}\sum_{p_i=1}^{P_i}(\xi_{mi}^{p_i})_i} \end{cases} \quad (12)$$

wherein max(•) is a function for finding a maximum value; and min(•) is a function for finding a minimum value;

2.4) selecting the p-th input feature of the i-th sub-process according to rules as follows:

$$\beta_i^{p_i} = \begin{cases} 1, & \text{if } (\xi_{mi}^{p_i})_i \geq \theta_i^{mi} \\ 0, & \text{else } (\xi_{mi}^{p_i})_i < \theta_i^{mi} \end{cases} \quad (13)$$

wherein $\theta_i^{mi}$ is taken as a threshold;

2.5) selecting a feature $(x^{p_i})_i$ of $\beta_i^{p_i}=1$ as a mutual information value-selected candidate feature; recording the mutual information value-selected candidate feature as $$\left(x^{(p_i)_{mi}^{sel}}\right)_i;$$

2.6) performing steps (2.1)-(2.5) for all of the input features of the i-th sub-process; and recording the selected candidate features as:

$$(X_{mi}^{sel})_i = \left[(x^1)_i, \ldots, \left(x^{(p_i)_{mi}^{sel}}\right)_i, \ldots, \left(x^{(P_i)_{mi}^{sel}}\right)_i\right] \quad (14)$$

wherein $(P_i)_{mi}^{sel}$ represents the number of mutual information value-selected features in the i-th sub-process; and $(X_{mi}^{sel})_i$ represents a candidate feature set selected based on a mutual information value measurement from the input features of the i-th sub-process; and 2.7) repeating steps (2.1)-(2.6) for all the sub-processes; and recording mutual information value measurement-selected features as $\{(X_{mi}^{sel})_i\}_{i=1}^I$.

6. The method of claim 5, wherein the step of obtaining the comprehensive evaluation value comprises:

3.1) for the i-th sub-process, taking the intersection of the mutual information-selected features $(X_{mi}^{sel})_i$ and the correlation coefficient-selected features $(X_{corr}^{sel})_i$ according to Equation (15), thereby obtaining a comprehensive evaluation value-selected candidate feature set, $$(X_{corr\_mi}^{sel})_i = (X_{mi}^{sel})_i \cap (X_{corr}^{sel})_i = \left[(x^1)_i, \ldots, \left(x^{(p_i)_{corr\_mi}^{sel}}\right)_i, \ldots, \left(x^{(P_i)_{corr\_mi}^{sel}}\right)_i\right] \quad (15)$$

wherein | represents the intersection;

$$x_i^{(p_i)_{corr\_mi}^{sel}}$$

represents a $(p_i)_{corr\_mi}^{sel}$-th candidate feature of the i-th sub-process; and a correlation coefficient value of the $(p_i)_{corr\_mi}^{sel}$-th candidate feature is $$\left(\xi_{corr}^{(p_i)_{corr\_mi}^{sel}}\right)_i;$$

and a mutual information value of the $(p_i)_{corr\_mi}^{sel}$-th candidate feature is $$\left(\xi_{mi}^{(p_i)_{corr\_mi}^{sel}}\right)_i;$$

3.2) performing normalization according to Equations (16) and (17) so as to eliminate size differences of the correlation coefficient value and mutual information value of the different input features;

$$\left(\zeta_{corr\_norm}^{(p_i)_{corr\_mi}^{sel}}\right)_i = \frac{\left(\xi_{corr}^{(p_i)_{corr\_mi}^{sel}}\right)_i}{\frac{1}{(P_i)_{corr\_mi}^{sel}}\sum_{(p_i)_{corr\_mi}^{sel}=1}^{(P_i)_{corr\_mi}^{sel}}\left(\xi_{corr}^{(p_i)_{corr\_mi}^{sel}}\right)_i} \quad (16)$$

$$\left(\zeta_{mi\_norm}^{(p_i)_{corr\_mi}^{sel}}\right)_i = \frac{\left(\xi_{mi}^{(p_i)_{corr\_mi}^{sel}}\right)_i}{\frac{1}{(P_i)_{corr\_mi}^{sel}}\sum_{(p_i)_{corr\_mi}^{sel}=1}^{(P_i)_{corr\_mi}^{sel}}\left(\xi_{mi}^{(p_i)_{corr\_mi}^{sel}}\right)_i} \quad (17)$$

wherein $$\left(\zeta_{corr\_norm}^{p_{corr\_mi}^{sel}}\right)_i$$

represents a standardized correlation coefficient value of the $p_{corr\_mi}^{sel}$-th candidate feature of the i-th sub-process; and $$\left(\zeta_{mi\_norm}^{p_{corr\_mi}^{sel}}\right)_i$$

represents a standardized mutual information value of the $p_{corr\_mi}^{sel}$-th candidate feature of the i-th sub-process;

3.3) defining the comprehensive evaluation value of the candidate input features as $$\zeta_i^{(p_i)_{corr\_mi}^{sel}},$$

expressing $$\zeta_i^{(p_i)_{corr\_mi}^{sel}}$$

as $$\zeta_{corr\_mi}^{(p_i)_{corr\_mi}^{sel}} = k_i^{corr} \cdot \zeta_{corr\_norm}^{(p_i)_{corr\_mi}^{sel}} + k_i^{mi} \cdot \zeta_{mi\_norm}^{(p_i)_{corr\_mi}^{sel}} \quad (18)$$

wherein $k_i^{corr}$ and $k_i^{mi}$ each represent a proportional coefficient; and $k_i^{corr} + k_i^{mi} = 1$; and 3.4) repeating steps (3.1)-(3.3) until comprehensive evaluation values of all of the candidate input features are obtained; and recording the obtained comprehensive evaluation values as $$\left\{\zeta_{corr\_mi}^{(p_i)_{corr\_mi}^{sel}}\right\}_{(p_i)_{corr\_mi}^{sel}=1}^{(P_i)_{corr\_mi}^{sel}}.$$

7. The method of claim 6, wherein $k_i^{corr}$ is equal to 0.5; and $k_i^{mi}$ is equal to 0.5.

8. The method of claim 6, wherein the step of obtaining the comprehensive evaluation value further comprises:

4.1) setting a weight factor of the i-th sub-process as $f_i^{corr\_mi}$; calculating a threshold $\theta_i^{1stsel}$ configured to select the input features based on the comprehensive evaluation value according to $$\theta_i^{1stsel} = f_i^{corr\_mi} \cdot \frac{1}{(P_i)_{corr\_mi}^{sel}}\sum_{(p_i)_{corr\_mi}^{sel}=1}^{(P_i)_{corr\_mi}^{sel}}\left(\zeta_{corr\_mi}^{(p_i)_{corr\_mi}^{sel}}\right)_i \quad (19)$$

wherein a maximum value $(f_i^{corr\_mi})_{max}$ and a minimum value $(f_i^{corr\_mi})_{min}$ of $f_i^{corr\_mi}$ are calculated according to $$\begin{cases} (f_i^{corr\_mi})_{max} = \dfrac{\max\left((\zeta_{corr\_mi}^{1})_i, \ldots, (\zeta_{corr\_mi}^{(p_i)_{corr\_mi}^{sel}})_i, \ldots, (\zeta_{corr\_mi}^{(P_i)_{corr\_mi}^{sel}})_i\right)}{\frac{1}{(P_i)_{corr\_mi}^{sel}}\sum_{(p_i)_{corr\_mi}^{sel}=1}^{(P_i)_{corr\_mi}^{sel}}\left(\zeta_{corr\_mi}^{(p_i)_{corr\_mi}^{sel}}\right)_i} \\[2ex] (f_i^{corr\_mi})_{min} = \dfrac{\min\left((\zeta_{corr\_mi}^{1})_i, \ldots, (\zeta_{corr\_mi}^{(p_i)_{corr\_mi}^{sel}})_i, \ldots, (\zeta_{corr\_mi}^{(P_i)_{corr\_mi}^{sel}})_i\right)}{\frac{1}{(P_i)_{corr\_mi}^{sel}}\sum_{(p_i)_{corr\_mi}^{sel}=1}^{(P_i)_{corr\_mi}^{sel}}\left(\zeta_{corr\_mi}^{(p_i)_{corr\_mi}^{sel}}\right)_i} \end{cases} \quad (20)$$

4.2) selecting a $(p_i)_{corr\_mi}^{sel}$-th candidate input feature of the i-th sub-process according to rules as follows:

$$\gamma^{(p_i)_{corr\_mi}^{sel}} = \begin{cases} 1, & \text{if } \zeta_{corr\_mi}^{(p_i)_{sel}^{sel}} \geq \theta_i^{1stsel} \\ 0, & \text{else } \zeta_{corr\_mi}^{(p_i)_{sel}^{sel}} < \theta_i^{1stsel} \end{cases} \quad (21)$$

wherein $\theta_i^{1stsel}$ is taken as a threshold;

4.3) performing steps (4.1)-(4.2) for all the original candidate input features; selecting variables of $$\gamma^{(p_i)_{corr\_mi}^{sel}} = 1$$

as comprehensive evaluation value-selected input features; and expressing the variables as:

$$(X_{1st}^{sel})_i = \left[(x^1)_i, \ldots, (x^{p_i^{sel}})_i, \ldots, (x^{p_i^{sel}})_i\right] \quad (22)$$

wherein $(X_{1st}^{sel})_i$ represents first-level features of the i-th sub-process selected using a comprehensive evaluation value measurement from the candidate feature set selected by a correlation coefficient method and a mutual information method; and 4.4) repeating steps (4.1)-(4.3) until the first-level features of all the sub-processes is obtained.

9. The method of claim 8, wherein the step of arranging the first-level features in series comprises:
arranging the first-level features in series to obtain the first-level features $X_{1st}^{sel}$ based on the single feature correlation;

$$X_{1st}^{sel} = \left[(X_{1st}^{sel})_1, \ldots, (X_{1st}^{sel})_i, \ldots, (X_{1st}^{sel})_I\right] = \left[x^{1_{1st}^{sel}}, \ldots, x^{p_{1st}^{sel}}, \ldots, x^{P_{1st}^{sel}}\right] \quad (23)$$

wherein $$x^{p_{1st}^{sel}}$$

represents a $p_{1st}^{sel}$-th feature in a first-level feature selection set;

$$P_{1st}^{sel} = \sum_{i=1}^{I} P_i^{sel}$$

represents the number of all of the first-level features; and $X_{1st}^{sel}$ represents single feature correlation-based first-level feature obtained by serially combining the first-level features of all of the sub-processes.

10. The method of claim 8, wherein a strategy of second-level feature selection comprises:
inputting the first-level features $X_{1st}^{sel}$; running the GAPLS algorithm times;
outputting the second-level features $(X_{2nd}^{sel})_j$ and then outputting the number of times that the respective first-level input features are selected; and statistically processing the second-level features that are selected $J_{sel}$ times, wherein when a GAPLS model prediction error is smaller than a prediction error average obtained by running the GAPLS algorithm J times, a second-level feature is selected;
recording the number of times that a $p_{1st}^{sel}$-th feature is selected as $$f_{num}^{p_{1st}^{sel}};$$

accordingly, recording all $P_{1st}^{sel}$-th features of the first-level features as $$\left\{f_{num}^{p_{1st}^{sel}}\right\}_{p_{1st}^{sel}=1}^{P_{1st}^{sel}};$$

wherein J is the number of times that the GAPLS algorithm runs; $J_{sel}$ is the number of GAPLS models prediction errors of which are smaller than a prediction error average; and $(X_{2nd}^{sel})_j$ represents multiple feature redundancy-based second-level features selected by jth run of the GAPLS algorithm.

11. The method of claim 10, wherein the step of the second-level feature selection comprises:
5.1) setting the number of times that the GAPLS algorithm runs as J; setting GAPLS algorithm parameters; initializing a population size, maximum genetic algebra, mutation probability, a crossover method and a number of latent variables of the PLS algorithm; and setting j=1 and starting the selection of the second-level features;
5.2) determining whether the GAPLS algorithm runs J times; if yes, proceeding to step (5.11); if no, proceeding to step (5.3);
5.3) performing binary encoding for features, wherein a length of a chromosome is the number of input features; 1 implies that a feature is selected; and 0 implies that no feature is selected;
5.4) performing random initialization on population;
5.5) evaluating the fitness of the population; and calculating a root mean square error of cross-validation (RMSECV) using a leave-one-out cross-validation method;
5.6) determining whether a termination condition of the maximum genetic algebra is reached, if no, proceeding to step (5.7); if yes, proceeding to step (5.9);
5.7) performing genetic operations comprising selection, crossover and variation, wherein the selection is performed through an elite substitution strategy, that is, individuals with poor fitness are replaced with individuals with good fitness; the crossover is performed through single point crossover; and the genetic variation is performed through single point mutation;
5.8) obtaining a new population and proceeding to step (5.5);
5.9) obtaining an optimal individual after running the GAPLS algorithm times; and performing decoding to obtain selected second-level features and recording the selected second-level features as $(X_{2nd}^{sel})_j$;
5.10) setting j=j+1; and proceeding to step (5.2);
5.11) calculating an average value of root mean square errors (RMSE) of a prediction model obtained by running the GAPLS algorithm J times; recording the number of the root mean square errors of the GAPLS model that are larger than the average value as $J_{sel}$;

processing the second-level features that are selected $J_{sel}$ times by counting the number of times that the $P_{1st}{}^{sel}$-th feature in the first-level features is selected, $$\left\{\left(x_{2nd}^{sel}\right)_j\right\}_{j=1}^{J_{sel}} \Rightarrow \left\{f_{num}^{1_{st}^{sel}}, \ldots, f_{num}^{p_{1st}^{sel}}, \ldots, f_{num}^{P_{1st}^{sel}}\right\} = \left\{f_{num}^{p_{1st}^{sel}}\right\}_{p_{1st}^{sel}=1}^{P_{1st}^{sel}}, \quad (24)$$

$$1 \le f_{num}^{p_{1st}^{sel}} \le J_{sel}$$

wherein $$f_{num}^{p_{1st}^{sel}}$$

is the number of times that the $p_{1st}{}^{sel}$-th feature in the first-level features is selected.

12. The method of claim 11, wherein the population size is 20; the maximum genetic algebra is 40; a maximum number of latent variables of the PLS algorithm is 6; and the mutation probability is 0.005.

13. The method of claim 11, wherein the step of the third-level feature selection comprises:
according to the number of times $$\left\{f_{num}^{p_{1st}^{sel}}\right\}_{p_{1st}^{sel}=1}^{P_{1st}^{sel}}$$

that all the $p_{1st}{}^{sel}$-th features in the first-level features are selected, setting a scale factor as $f_{DXN}{}^{RMSE}$; determining the lower limit of the threshold $\theta_{DXN}{}^{3rd}$ configured to select the third-level features as $\theta_{DXN}{}^{downlimit}$; calculating $\theta_{DXN}{}^{downlimit}$ according to:

$$\theta_{DXN}^{downlimit} = \text{floor}\left(f_{DXN}^{RMSE} \cdot \frac{1}{P_{1st}^{sel}} \sum_{p_{1st}^{sel}=1}^{P_{1st}^{sel}} f_{num}^{p_{1st}^{sel}}\right) \quad (25)$$

wherein floor(•) represents a function that returns integers;
calculating a maximum value $(f_{DXN}{}^{RMSE})_{max}$ and a minimum value $(f_{DXN}{}^{RMSE})_{min}$ of $f_{DXN}{}^{RMSE}$ according to $$\begin{cases} \left(f_{DXN}^{RMSE}\right)_{max} = \dfrac{\max\left(f_{num}^{1_{st}^{sel}}, \ldots, f_{num}^{p_{1st}^{sel}}, \ldots, f_{num}^{P_{1st}^{sel}}\right)}{\dfrac{1}{P_{1st}^{sel}} \sum_{p_{1st}^{sel}=1}^{P_{1st}^{sel}} f_{num}^{p_{1st}^{sel}}} \\ \left(f_{DXN}^{RMSE}\right)_{min} = \dfrac{\min\left(f_{num}^{1_{st}^{sel}}, \ldots, f_{num}^{p_{1st}^{sel}}, \ldots, f_{num}^{P_{1st}^{sel}}\right)}{\dfrac{1}{P_{1st}^{sel}} \sum_{p_{1st}^{sel}=1}^{P_{1st}^{sel}} f_{num}^{p_{1st}^{sel}}} \end{cases} \quad (26)$$

finding a maximum value of the number of times that all the $p_{1st}{}^{sel}$-th features in the first-level features are selected based on the upper limit $\theta_{DXN}{}^{uplimit}$ of the threshold configured to select the third-level features, $$\theta_{DXN}^{uplimit} = \max\left(f_{num}^{1_{st}^{sel}}, \ldots, f_{num}^{p_{1st}^{sel}}, \ldots, f_{num}^{P_{1st}^{sel}}\right) \quad (27)$$

recording the threshold $\theta_{DXN}{}^{3rd}$ between $\theta_{DXN}{}^{downlimit}$ and $\theta_{DXN}{}^{uplimit}$; and performing the third-level feature selection according to $$\mu^p = \begin{cases} 1, & \text{if } f_{num}^{p_{1st}^{sel}} \ge \theta_{DXN}^{3rd} \\ 0, & \text{else } f_{num}^{p_{1st}^{sel}} < \theta_{DXN}^{3rd} \end{cases} \quad (28)$$

wherein $$f_{num}^{p_{1st}^{sel}}$$

represents the number of times that the $p_{1st}{}^{sel}$-th feature in the first-level features is selected by running the GAPLS algorithm J times; $\mu^p$ represents a threshold selection criterion for selecting the third-level features;

sequentially storing feature variables of $\mu^p=1$ in $X_{3rd}{}^{sel\_temp}$ and calculating the RMSE, wherein $X_{3rd}{}^{sel\_temp}$ serves as input variables in the establishment of the PLS algorithm-based DXN detection model; and $X_{3rd}{}^{sel}$ represents the third-level features selected from $X_{1st}{}^{sel}$ based on a feature selection threshold $\theta_{3rd}$ and prior knowledge.

14. The method of claim 1, wherein variables of the PLS algorithm-based DXN detection model have 287 dimensions.

15. The method of claim 1, wherein weight factors $f_i{}^{corr}$, $f_i{}^{mi}$ and $f_i{}^{corr\_mi}$ of feature selection of the correlation coefficient value and the mutual information value of the first-level features are 0.8.

16. The method of claim 1, wherein there are 132 feature variables selected by the comprehensive evaluation value; for the selected 132 process variables based on the single feature correlation, an optimal process variable combination is determined using the GAPLS algorithm so as to remove redundant features.

\* \* \* \* \*